(12) United States Patent
Gaillard et al.

(10) Patent No.: US 8,613,929 B2
(45) Date of Patent: *Dec. 24, 2013

(54) METHODS AND COMPOSITIONS FOR TARGETING AGENTS INTO AND ACROSS THE BLOOD-BRAIN BARRIER AND OTHER ENDOTHELIAL CELL MICROVASCULAR BARRIERS

(75) Inventors: Pieter J. Gaillard, Valkenburg (NL);
Albertus G. De Boer, Leiderdorp (NL);
Arjen Brink, Amsterdam (NL)

(73) Assignee: TO-BBB Holding B.V., Valkenburg (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/188,458

(22) Filed: Jul. 21, 2011

(65) Prior Publication Data

US 2011/0274749 A1    Nov. 10, 2011

Related U.S. Application Data

(63) Continuation of application No. 10/544,991, filed as application No. PCT/NL2004/000092 on Feb. 10, 2004, now Pat. No. 8,026,209.

(60) Provisional application No. 60/446,270, filed on Feb. 11, 2003, provisional application No. 60/491,522, filed on Aug. 1, 2003.

(30) Foreign Application Priority Data

Feb. 10, 2003    (EP) ..................................... 03075390

(51) Int. Cl.
*A61K 39/40*    (2006.01)
*A61K 39/44*    (2006.01)
*A61K 47/42*    (2006.01)
*A61K 31/727*    (2006.01)
*A61K 9/127*    (2006.01)
*A61P 25/00*    (2006.01)

(52) U.S. Cl.
USPC .................. 424/178.1; 424/181.1; 424/182.1; 424/1.49; 514/1.2; 514/17.5; 514/17.7; 514/17.8; 514/20.8; 514/56; 514/575; 514/450; 977/808; 977/801; 977/773; 977/714

(58) Field of Classification Search
None
See application file for complete search history.

(56) References Cited

U.S. PATENT DOCUMENTS

2009/0269361 A1 * 10/2009 Shone et al. ............... 424/183.1

FOREIGN PATENT DOCUMENTS

WO    WO 9822092 A1 *   5/1998
WO    WO 0192333 A2 *  12/2001

OTHER PUBLICATIONS

Dehouck B et al. A new function for the LDL receptor: transcytosis of LDL across the blood-brain barrier. J Cell Biol. 1997; 138:877-889.*
Raab G and Kagsbrun M. Heparin-binding EGF-like growth factor. Biochim et Biophys Acta, 1997; 1333:F179-F199.*
Scherrmann JM. Drug delivery to brain via the blood-brain barrier. Vascular Pharmacol. 2002; 38:349-354.*
Takahashi et al. Extension of juxtamembrain domain of diphtheria toxin receptor arrests translocation of diphtheria toxin fragment A into cytosol. Biochem

METHODS AND COMPOSITIONS FOR TARGETING AGENTS INTO AND ACROSS THE BLOOD-BRAIN BARRIER AND OTHER ENDOTHELIAL CELL MICROVASCULAR BARRIERS

BACKGROUND OF THE INVENTION

1. Field of the Invention

The invention relates to novel nucleic acids and polypeptides encoded thereby, whose expression is modulated in brain microvascular endothelial cells undergoing early dynamic inflammation-induced changes in blood-brain bather functionality. These polypeptides are designated herein as "lipopolysaccharide-sensitive" polypeptides (LPSS polypeptides). The invention further relates to methods useful for controlling blood-brain barrier properties in mammals in need of such biological effects. This includes the diagnosis and treatment of disturbances in the blood-brain/retina barrier, brain (including the eye) disorders, as well as peripheral vascular disorders. Additionally, the present invention further relates to the use of anti-LPSS polypeptide antibodies or ligands as diagnostic probes, as blood-brain barrier targeting agents or as therapeutic agents as well as the use of ligands or modulators of expression, activation or bioactivity of LPSS polypeptides as diagnostic probes, therapeutic agents or drug delivery enhancers.

2. Description of the Background Art

In order to function properly, neurons require a tightly regulated extracellular milieu. This essential, well-defined microenvironment is locally maintained by nursing brain cells called astrocytes (or astroglia). To cope with the considerable and variable dissimilarity between the composition of the blood and the extracellular compartment of the brain, the central nervous system (CNS) is also shielded from the general blood circulation by a number of blood-CNS barriers, i.e. the blood-brain barrier, blood-cerebral spinal fluid (CSF) barrier, pial vessel-CSF barrier, the ependyma and glia limitans, and also the blood-retina barrier, blood-nerve barrier, blood-spinal cord barrier. The blood-brain barrier (BBB) is considered as the most important blood-CNS barrier, because it covers a 1000 times larger surface area when compared to the other blood-CNS barriers. The BBB is characterized by a unique tight endothelial cell layer that covers capillary blood vessels in the CNS. Again, astrocytes are the principal inducers of BBB properties in these endothelial cells, by projecting 'glial foot' on the capillaries.

In particular, the BBB regulates the trafficking of ions ($Na^+$, $K^+$, $Ca^{2+}$), water, nutrients, metabolites, neurotransmitters (glutamic acid, tryptophan), plasma proteins (albumin, fibrinogen, immunoglobulins), cells from the immune system and also xenobiotics (drugs) in and out of the brain. The capillary endothelium in the brain has special properties when compared to peripheral capillaries. It has narrow tight-junctions, no fenestrae, low pinocytotic activity and a continuous basement membrane. The narrow tight-junctions result in a high electrical resistance of 1500-2000 Ohm·$cm^2$. In addition, the endothelial cells have a negative surface charge that repulses negatively charged compounds. They have many mitochondria and enzymes to break down compounds and various selective transport systems to actively transport nutrients and other compounds into and out of the brain. Under healthy conditions, the BBB not only regulates the entry of drugs or endogenous compounds into the brain, but also cellular infiltration is lower compared to peripheral organs. The normal endothelial cell layer provides a thrombo-resistant surface that prevents platelet and leukocyte adhesion and activation of any coagulation system. The highly specialized brain microvascular endothelial cells form a tight barrier which isolates the brain from immune surveillance, and allow only a few mononuclear cells (such as activated T-cells) to migrate into the CNS. The low expression of major histocompatibility complex antigens, the low number of antigen-presenting cells in the healthy CNS, and the fact that the CNS is not properly drained by a fully developed lymphatic vasculature, make the brain an "immuno-secluded" site.

The present understanding of the anatomical basis of the BBB is that it functions as a dynamically regulated organ, influenced by peripheral (e.g., cortisol, adrenaline) and local (e.g., cytokines, chemokines) hormones. In addition to astrocytes, several other cells like pericytes, neurons and cells of the immune system, influence its properties. Next to that, the endothelium is involved in other processes like coagulation, control of vasotonus, antigen-presentation and the control of the basement membrane by e.g., growth factors. Particularly, under pathological conditions like brain and cerebral inflammation, angiogenesis in brain tumors, the activated endothelium plays an important role.

In general, the BBB can be regarded as an organ that serves to protect the homeostasis of the brain. Not surprisingly, dysfunction of the BBB plays a central role in the vast majority of brain disorders. Some examples are:

i. Cerebral vasogenic edema is the result of disease (inflammation) induced leakage of plasma proteins and water from the blood into brain tissue. This is the principal cause of death and disabilities in disorders like stroke, cerebral infections, head trauma, brain tumors and multiple sclerosis. The edema causes the brain to swell within the rigid environment of the scull. The resulting elevation in intracranial pressure may subsequently lead to herniation of the brain followed by failure of essential brain functions like respiration and, if left untreated, results in severe disabilities, coma and even death.

ii. In multiple sclerosis, activated autoreactive T cells cross the activated BBB. Within the CNS, these T cells induce an inflammatory response targeted against myelin, which also causes a disruption of the BBB. Autoantibodies and complement factors now cross the disrupted BBB, which leads to the process of demyelination. Now, myelin fragments also leak back into the periphery through the disrupted BBB, where it activates more autoreactive T cells and increases the production of more autoantibodies.

iii. Failure to secure the delicate ion and neurotransmitter balances within the extracellular fluid leads to impaired neuronal signaling and therefore to impaired cognitive functioning, neuropsychiatric disorders or epileptic seizures.

iv. Impaired clearance of toxic proteins across the BBB into the blood stream has recently been linked to the pathogenesis of neurodegenerative disorders like Alzheimer's disease and prion diseases like Creutzfeldt-Jakob disease and BSE. Pathological accumulation of such proteins leads to neuronal cell death and subsequently to impaired cognitive functioning.

Healing a dysfunctional BBB thus opens new avenues for the treatment of brain disorders. Brain disorders are the principal cause of morbidity and disabilities in the western world. The identification and characterization of novel LPSS polypeptides, whose gene expression is modulated in brain microvascular endothelial cells undergoing early dynamic inflammation-induced changes in blood-brain bather functionality, will prove useful to meet these needs.

In addition to the desirable drugs with a BBB-healing capacity for the treatment of brain disorders, a proper functioning BBB is also essential to block or reduce the entry into the brain of lymphocytes, which mediate an immune response. The same holds for the entry into the brain of metastatic cancer cells. The identification and characterization of novel LPSS polypeptides, whose gene expression is modulated in brain microvascular endothelial cells undergoing early dynamic inflammation-induced changes in blood-brain barrier functionality, will prove useful to meet these needs.

The BBB, however, also limits the delivery of xenobiotics (such as drugs and diagnostic agents) to the brain, which complicates classical drug therapy (i.e. targeted against neurons) of brain disorders. It is therefore also desirable to either manipulate the permeability of the BBB in order to deliver blood-borne, membrane-impermeant drugs to the brain by reversibly opening the BBB, or to selectively target drugs to the brain via endogenous BBB transport systems. The same holds for drug delivery across the blood-testis barrier and the blood-placenta barrier. The identification and characterization of novel LPSS polypeptides, whose gene expression is modulated in brain microvascular endothelial cells undergoing early dynamic inflammation-induced changes in blood-brain barrier functionality, will also prove useful to meet these needs.

It is also desirable to manipulate BBB properties in microvessels of other organs than the brain or eye affected in vascular disorders. Introducing BBB properties in peripheral microvessels will be beneficial in conditions involving (micro)angiopathies, pathological angiogenesis, failure of blood-testis barrier or blood-placenta barrier, and conditions such as pulmonary edema, shock caused by bacterial endotoxins, hyperfibrinolysis and anaphylactic shock. The identification and characterization of novel LPSS polypeptides, whose gene expression is modulated in brain microvascular endothelial cells undergoing early dynamic inflammation-induced changes in blood-brain barrier functionality, will also prove useful to meet these needs.

It has been known for a long time that brain astrocytes induce BBB properties in brain capillary endothelial cells (BCEC) by the projection perivascular end feet (Arthur et al., 1987, Brain Res. 433: 155-159; Janzer and Raff, 1987, Nature 325: 253-257). It is also known for a long time that this induction is brought about by soluble factor(s), since astrocyte conditioned medium (ACM) can reproduce some of the inductive effects (Tio et al., 1990, Eur. J. Morphol. 28(2-4): 289-300). Several candidate molecules have been identified, capable of mimicking aspects of ACM-mediated barrier induction in BCEC; these include TGFβ, GDNF, bFGF, IL-6 and steroids. Others have found that the factor is not a protein or peptide and that it contains an iron-nitric oxide adduct (Federici et al., 1995, J. Neurochem. 64(3): 1008-1015; Regina et al., 2001, Biochim Biophys. Acta 1540(3): 233-242). So one can conclude that despite the effort of several research groups, the responsible astrocyte-derived factor has not been identified yet.

In previous experiments, we found that primary isolated BCEC, exposed to ACM, retained many of the essential BBB properties in culture (Gaillard et al., 2001, *Eur J Pharm Sci.* 12:215-22). By introducing primary cultured brain astrocytes at the bottom of the cell culture well, the transendothelial electrical resistance (TEER) across BCEC monolayers cultured on filter inserts above was increased to about 150% of BCEC monolayers cultured in ACM alone. Moreover, when culturing the astrocytes on the bottom side of the filter insert, thus in close proximity of the BCEC, TEER multiplied by a factor 3-8. In addition, the paracellular transport of sodium fluorescein (FLU, mol. weight 376 Da) and FITC-labeled dextran (FD4, MW 4 kDa) decreased to about 50% of BCEC cultured in ACM alone. In conclusion, the proximity of astrocytes from the BCEC determined the magnitude of the effect, although they did not make physical contact with the BCEC (Gaillard et al., supra).

TEER is a sensitive measure to quantify the permeability of small ions through the tight junctions between BCEC. TEER thus represents the functionality of tight junctions, which are considered the major hallmark of the BBB. The absolute value of TEER is mainly dependent on the amount and complexity of tight junctions between the cells. Likewise, this is also the limiting factor for the paracellular transport of large and hydrophilic compounds.

In additional studies, we found that astrocytes cultured on the bottom side of the filter insert:

(1) maintained (or re-induced) the expression of P-glycoprotein (Pgp, a drug efflux pump involved in multidrug resistance) on BCEC after the first passage (Gaillard et al., 2000, *Pharm. Res.* 17:1198-1205);

(2) decreased the sensitivity for vinblastine induced BBB disruption (a Pgp functionality assay) (Gaillard et al., 2000, supra);

(3) induced active transport of Pgp substrates from the basolateral (CNS) side to the apical (blood) side of a filter, while this was not observed in BCEC monolayers, despite the fact that Pgp was expressed in BCEC monolayers (Gaillard et al., 2000, supra);

(4) mediated a protective response to LPS-induced BCEC disruption (Gaillard, P., 2000a, Ph.D. Thesis, Leiden University, p 81-97). None of these effects were induced by ACM alone. Apparently, the physical and proximate presence of astrocytes on the bottom side of the filter inserts is superior in inducing BBB properties in BCEC when compared to ACM alone.

There exists thus a need for additional products, methods and assays that provide a means to control BBB properties or identify and modulate cellular responses to early dynamic inflammation induced changes in BBB functionality and tissue response to such changes. Such products, methods and assays will provide benefit in numerous medical conditions and procedures, such as those mentioned above.

DESCRIPTION OF THE INVENTION

Definitions

An "alteration of the activity or steady state level of a polypeptide" herein means any detectable change in the biological activity exerted by the polypeptide or in the steady state level of the protein as compared the normal activity or steady-state in a healthy individual.

An "agonist" is herein defined as any molecule that mimics a biological activity, preferably the biological activity of a polypeptide, a receptor or its ligand. An antagonist is any molecule that partially or fully blocks, inhibits or neutralizes such a biological activity.

The term "treatment" of vascular disorders refers to, inter alia, reducing or alleviating one or more symptoms in an individual, preventing one or more symptoms from worsening or progressing, promoting recovery or improving prognosis, and/or preventing disease in an individual who is free therefrom as well as slowing or reducing progression of existing disease. For a given individual, improvement in a symptom, its worsening, regression, or progression may be determined by an objective or subjective measure. Efficacy of treatment may be measured as an improvement in morbidity or mortality (e.g., lengthening of survival curve, for a selected population).

Figure 2:
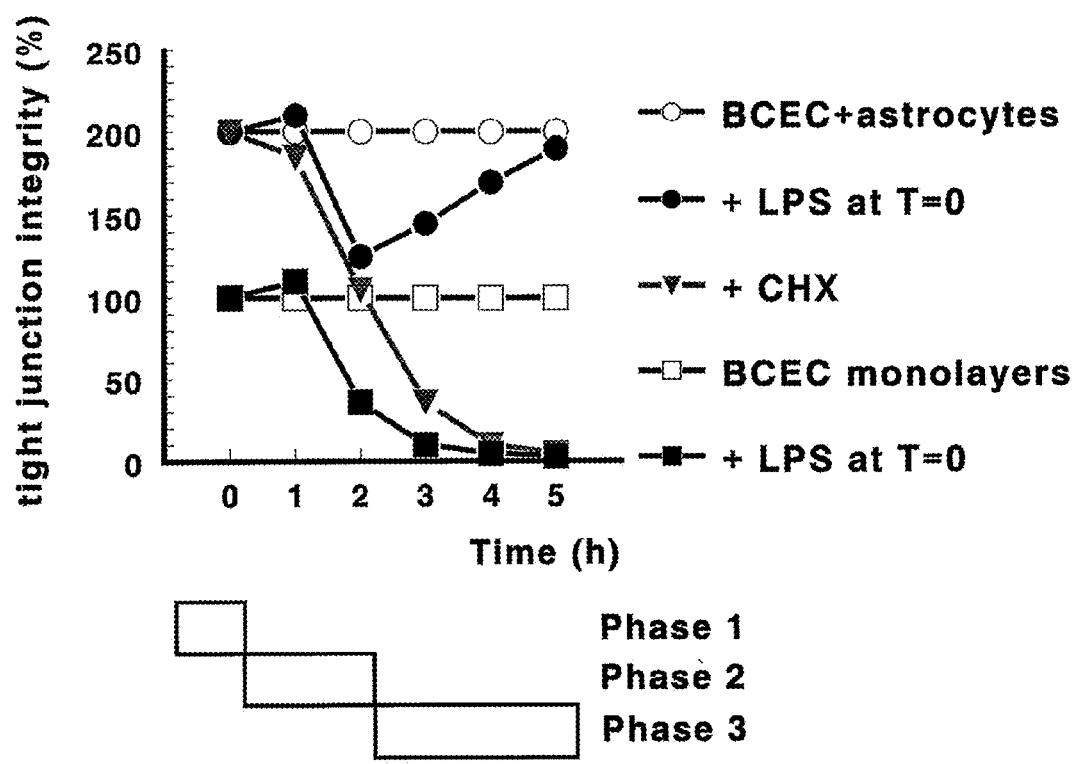
FIG. 2 is a schematically detailed representation of the event that occurs at the BBB in vitro after exposure to lipopolysaccharide (LPS). BCEC were cultured as monolayers in 50% ACM or co-cultured with astrocytes. Astrocytes increased in vitro BBB performance (phase 1). Disease-induction by LPS, disrupted BCEC monolayers (phase 2), while BCEC+ astrocyte co-cultures were able to recover (phase 3). This recovery process involves de novo protein synthesis, since cycloheximide (CHX) was able to completely inhibit the recovery phase.

Increased permeability of the endothelial/vascular barrier makes it more leaky (i.e., less tight, more permeable). Decreased permeability of the endothelial/vascular barrier makes it more tight (i.e., less leaky, less permeable). Treating a vascular disorders thus means decreasing vascular permeability, whereas increasing drug delivery thus requires increased vascular permeability. LPSS polypeptides of the invention which are upregulated in BCEC from BCEC-astrocyte cocultures are involved in increased vascular permeability. LPSS polypeptides of the invention which are downregulated in BCEC from BCEC-astrocyte cocultures are involved in increased vascular permeability. LPSS polypeptides of the invention which are differentially up- or downregulated between BCEC monolayers and BCEC-astrocyte cocultures are involved in the ability to recover from the inflammatory stimulus (FIG. 2).

Modulation of Endothelial Permeability

In a first aspect the invention relates to a method for modulating the permeability of endothelial cells. The method comprises altering in the endothelial cells the activity or the steady-state level of a LPSS polypeptide having an amino acid sequence with at least 90% identity with an amino acid sequence as depicted in SEQ ID NOs:1-25. Sequence identities or similarities are herein defined as described below.

The endothelial cells are preferably vascular endothelial cells, more preferably microvascular endothelial cells. Most preferably the endothelial cells are microvascular endothelial cells that constitute or are part of one of the blood-central nervous system (CNS) bathers, such as the blood-brain bather, blood-retina barrier, blood-nerve barrier, blood-spinal cord barrier, of which brain microvascular endothelial cells are most preferred.

Such endothelial barrier cells may be characterized in situ, ex situ (i.e., in isolated capillaries) or in vitro by e.g., specific endothelial cell markers, specific barrier markers, but also by barrier functional assays. More specifically, endothelial cells may be characterized by their morphology in situ, i.e. a tube-like structure of with a diameter of about 10-20 micrometers, formed by single (or no more than three) continuously connected endothelial cells, surrounded by a continuous basal lamina, in which perivascular pericytes reside and astrocyte endfeet are projected upon. Both in and ex situ, as well as in vitro, barrier-like endothelial cells are between 1 and 5 micrometers thick, have many mitochondria, are connected by tight junctions, have no intercellular clefts, no fenestrations and very few pinocytotic vesicles, as can be observed by e.g., electron microscopy. In vitro, capillary structures may be characterized by their morphology in culture i.e., a tube-like structure with a diameter of about 10-20 micrometers, between 50 and 200 micrometers long. In vitro, endothelial cells may be characterized by their morphology in culture i.e., cobblestone shape (when growing in a cluster, e.g., out from a capillary) and spindle shape (when confluent), with a centered oval nucleus, as can be observed by e.g., phase-contrast microscopy. They may also be characterized by using a panel of general endothelial cell specific markers and functions e.g., expression of endothelial specific cluster of differentiation (CD) antigens (VCAM (CD106), CD31, EN-4, ICAMs, E-Selectin, PECAM, RBA), cadherins, integrins, actin, vimentin, factor VIII related antigen (vWF), collagen I and IV, fibronectin, matrix metalloproteinases, tissue inhibitor of metalloproteinases; non-thrombogenicity; low leukocyte adherence; release of vasoactive compounds (nitric oxide, endothelin-1 and prostacyclins); uptake of DiI-labeled-acetylated low density lipoprotein (DiI-Ac-LDL); lectin binding; presence of angiotensin converting enzyme, alkaline phosphatase, monoamine oxidase and anionic sites. In addition, typical barrier markers and functions may be used, like visualization of tight junctions or tight junction-related proteins (ZO-1) and restricted paracellular transport of reference compounds (such as e.g., Evans blue (binds to albumin), mannitol, sucrose, fluorescein, dextrans, albumin, AIB); absence of vesicular transport; absence of non-barrier markers like PAL-E; expression of gamma-glutamyl-transpeptidase (γ-GTP); expression and functionality of P-glycoprotein (Pgp), multidrug resistance proteins 1-7, glucose transporters, nucleoside transporters, organic anion transporters, large and neutral amino acid transporters; transferrin receptors, insulin-growth factor receptors, scavenger receptors; marginal F-actin localization and expression of many mitochondria, although none of these are specific for endothelial cells. (Functional) expression of these markers may be determined by e.g., molecular biological, biochemical, (immuno)-histo(cyto)chemical techniques as well as by functional assays using known substrates, ligands and/or inhibitors. These markers have been described and reviewed in international scientific journals (de Boer et al., 1999, *Eur J Pharm Sci.* 8):1-4; Hofman et al., 2001, *Invest Ophthalmol Vis Sci.* 42:895-901; Schlingemann et al., 1997, *Ophthalmic Res.* 29:130-8; Schlingemann et al., 1999, *Diabetologia.* 42:596-602; Vorbrodt et al., 1986, *Brain Res.* 394:69-79; Dai et al., 2002, *Brain Res.* 954:311-316).

The permeability of the endothelial cells is herein understood to mean the measure of the ease with which a compound (may that be ions (e.g., $Na^+$, $K^+$, $Ca^{2+}$), water, nutrients (e.g., glucose, amino acids), metabolites, neurotransmitters (e.g., glutamic acid, tryptophan), hormones, peptides, plasma proteins (e.g., albumin, fibrinogen, immunoglobulins, cytokines, growth factors), cells and xenobiotics (e.g., drugs, diagnostic markers)) can diffuse across, or be (actively) transported into or across, an endothelial cell layer in the luminal to abluminal direction or visa versa. Changes in permeability of the endothelial cells can also be the result of endothelial biotransformation of a given compound (may that be nutrients (e.g., glucose, amino acids), metabolites, neurotransmitters (e.g., glutamic acid, tryptophan), hormones, peptides, plasma proteins (e.g., albumin, fibrinogen, immunoglobulins, cytokines, growth factors), cells and xenobiotics (e.g., drugs, diagnostic markers)). The modulation of the permeability includes both increases and decreases in permeability. The permeability may conveniently be determined in vitro by determining the transendothelial electrical resistance (TEER) as described in the Examples. TEER is a sensitive measure to quantify the permeability of ions through the tight junctions between cells. In the method of the invention, a modulation of the permeability of the endothelial cells preferably is a modulation that results in a change of the TEER of at least 20, 50, 100, 300 or 1000% (Gaillard et al., 2000b, *Eur J Pharm Sci.* 12:95-102). Other methods for determining the permeability include e.g., the demonstration of changes in (functional) expression of the endothelial/barrier markers described above involved in permeability control by e.g., molecular biological, biochemical, (immuno)-histo(cyto)chemical techniques or by functional assays using known substrates, ligands and/or inhibitors of transporter systems. More specifically, changes in permeability may be demonstrated by loss of tight junction expression, appearance of intercellular clefts, fenestrations and/or number and localization of pinocytotic vesicles, as can be observed by e.g., electron microscopy (Hofman et al., supra). Changes in expression levels of the endothelial cell markers involved in endothelial permeability like ZO-1, PAL-E, RBA, F-actin, factor VIII related antigen (vWF), γ-GTP, Pgp, glucose transporters, PECAM, integrins, cadherin-5, transferrin receptors, lectin-binding sites or alkaline phosphatase, are all indicative for changes in endothelial permeability (Gaillard et al., 2001, supra; de Boer et al., 1999, supra; Schlingemann et al., 1997, supra; Schlingemann et al., 1999, supra; Tio et al., 1990, supra; Vorbrodt et al., 1986, supra; Dai et al., 2002, supra). Functional assays for restricted paracellular transport of reference compounds (e.g., mannitol, sucrose, fluorescein, dextrans, albumin), polar and active and inhibitable (with e.g., verapamil, PSC-833, temperature) transport of Pgp-substrates (rhodamine 123, vinblastine, etc.) or transferrin across endothelial cell layers are indicative for changes in endothelial permeability (Gaillard et al., 2000, 2001, supra).

In vivo the permeability of the endothelial cells may be determined by the demonstration of changes in (functional) expression of the endothelial/barrier markers that are involved in permeability control as described above for the in vitro situation (by e.g., molecular biological, biochemical, (immuno)-histo(cyto)chemical techniques or by functional assays using known substrates, ligands and/or inhibitors of transporter systems). In addition, extravasation of endogenous (e.g., fibrinogen, IgG) or (fluorescence- or radiolabeled) exogenous (e.g., Evans blue (binds to albumin), mannitol, sucrose, fluorescein, dextrans, albumin, AIB) reference compounds may be determined by (immuno)-histo(cyto) chemical techniques or by several in vivo sampling methods, like brain uptake index (BUI, Oldendorf, 1970 *Brain Res.* 24:372-6), brain efflux index (BEI, Kakee et al., 1996 *J Pharmacol Exp Therap.* 277:1550-9), in situ perfusion (Takasato et al., 1984 *Am J. Physiol.* 247(3 Pt 2):H484-93), single or multiple pass brain perfusion (Brodie et al., 1960, *J Pharmacol Exp Ther.* 130:519-28), CSF sampling (unit impulse response, van Bree et al., 1989. *J. Pharmacokin. Biopharm.* 17:441-62), positron emission tomography (PET, Hendrikse et al., 1998, *Br J. Pharmacol.* 124:1413-18), magnetic resonance techniques (MRI, MRS, Jenkins et al., 1999, *Ann NY Acad. Sci.* 893:214-42), quantitative autoradiography (QAR, Smith, 1989 In *Implications of the Blood-Brain Barrier and its Manipulation, vol. 1: Basic science aspects.* New York: Plenum Publ. Corp., E. A. Neuwelt, (ed.) pp 85-118), and intracerebral microdialysis (de Lange et al., 2000, *Adv Drug Deliv Rev.* 45: 125-48).

In the method of the invention, preferably the activity or steady-state level of the LPSS polypeptide may be altered at the level of the polypeptide itself, e.g., by providing the LPSS polypeptide to the endothelial cells from an exogenous source, or by adding an antagonist or inhibitor of the LPSS polypeptide to the endothelial cells, such as e.g., an antibody against the LPSS polypeptide. For provision of the LPSS polypeptide from an exogenous source the LPSS polypeptide may conveniently be produced by expression of a nucleic acid encoding the LPSS polypeptide in suitable host cells as described below. An antibody against the LPSS polypeptide may be obtained as described below.

Alternatively, the activity or steady-state level of the LPSS polypeptide may be altered by regulating the expression level of a nucleotide sequence encoding the polypeptide. Preferably, the expression level of a nucleotide sequence is regulated in the endothelial cells. The expression level of the LPSS polypeptide may be up-regulated by introduction of an expression vector into the endothelial cells, whereby the expression vector comprises a nucleotide sequence encoding the LPSS polypeptide, and whereby the nucleotide sequence is under control of a promoter capable of driving expression of the nucleotide sequence in the endothelial cells. The expression level of the LPSS polypeptide may also be up-regulated by introduction of an expression vector into the endothelial cells, whereby the expression vector comprises a nucleotide sequence encoding a factor capable of trans-activation of the endogenous nucleotide sequence encoding the LPSS polypeptide.

Alternatively, the expression level of the LPSS polypeptide may be down regulated by providing an antisense molecule to the cells, whereby the antisense molecule is capable of inhibiting the expression of the nucleotide sequence encoding the LPSS polypeptide. The antisense molecule may be provided as such or it may be provided by introducing an expression vector into the endothelial cells, whereby the expression vector comprises an antisense nucleotide sequence that is capable of inhibiting the expression of the nucleotide sequence encoding the LPSS polypeptide, and whereby the antisense nucleotide sequence is under control of a promoter capable of driving expression of the antisense nucleotide sequence in the endothelial cells. The expression level of the LPSS polypeptide may also be down-regulated by introducing an expression vector into the endothelial cells, whereby the expression vector comprises a nucleotide sequence encoding a factor capable of trans-repression of the endogenous nucleotide sequence encoding the LPSS polypeptide.

Generally, the activity or steady state level of LPSS polypeptides may thus be modified by:

1. Increasing gene expression, e.g., by providing:
   (a) an expression or gene therapy vector in which a nucleotide sequence coding for a LPSS polypeptide is operably linked to a promoter;
   (b) an expression or gene therapy vector in which a nucleotide sequence coding for a LPSS polypeptide receptor is operably linked to a promoter;
   (c) an expression or gene therapy vector in which a nucleotide sequence coding for an agonist of a LPSS polypeptide receptor is operably linked to a promoter LPSS;
   (d) an expression or gene therapy vector in which a nucleotide sequence coding for an antagonist of a LPSS polypeptide receptor is operably linked to a promoter LPSS.
2. Decreasing gene expression by providing any functional RNA molecule as e.g., recently reviewed by Famulok et al. (2002, *Trends Biotechnol.*, 20:462-6) including, e.g.,
   (a) an antisense nucleic acid molecule against a nucleotide sequence coding for a LPSS polypeptide;
   (b) an antisense nucleic acid molecule against a nucleotide sequence coding for a LPSS polypeptide receptor;
   (c) an antisense nucleic acid molecule against a nucleotide sequence coding for a LPSS polypeptide receptor agonist;
   (d) an antisense nucleic acid molecule against a nucleotide sequence coding for a LPSS polypeptide receptor antagonist;
   (e) an expression or gene therapy vector in which an antisense nucleic acid sequence against a nucleotide sequence coding for a LPSS polypeptide is operably linked to a promoter;
   (f) an expression or gene therapy vector in which an antisense nucleic acid sequence against a nucleotide sequence coding for a LPSS polypeptide receptor is operably linked to a promoter;
   (g) an expression or gene therapy vector in which an antisense nucleic acid sequence against a nucleotide sequence coding for a LPSS polypeptide receptor agonist is operably linked to a promoter;
   (h) an expression or gene therapy vector in which an antisense nucleic acid sequence against a nucleotide sequence coding for a LPSS polypeptide receptor antagonist is operably linked to a promoter.
3. Agonists, including e.g.:
   (a) a full or partial agonist of a LPSS polypeptide, such as, e.g.,
      (i) a natural ligand;
      (ii) a LPSS polypeptide or fragment thereof;
      (iii) peptidomimetics;
      (iv) an agonistic antibody or antibody fragment;
      (v) a small molecule, or another drug;
   (b) a full or partial agonist of a LPSS polypeptide receptor, such as, e.g.,
      (i) a natural ligand;
      (ii) a LPSS polypeptide or fragment thereof;
      (iii) peptidomimetics;
      (iv) an agonistic antibody or antibody fragment;
      (v) a small molecule, or another drug.
2. Antagonist including, e.g.,
   (a) a full or partial antagonists of a LPSS polypeptide, such as, e.g.,
      (i) a natural antagonist;
      (ii) a LPSS polypeptide fragment;
      (iii) peptidomimetics;
      (iv) an antagonistic or neutralizing antibody or antibody fragment;
      (v) a small molecule, or another drug;
   (b) a partial or inverse agonist of a LPSS polypeptide receptor, such as, e.g.,
      (i) a natural ligand;
      (ii) a LPSS polypeptide fragment;
      (iii) peptidomimetics;
      (iv) an antibody or antibody fragment;
      (v) a small molecule, or another drug.
   (c) a full or partial antagonists of a LPSS polypeptide receptor
      (i) a natural antagonist of a LPSS polypeptide receptor;
      (ii) a LPSS polypeptide fragment;
      (iii) peptidomimetics;
      (iv) an antagonistic or neutralizing antibody or antibody fragment;
      (v) a small molecule, or another drug.

Thus, in the method of the invention, the permeability of the endothelial cells is preferably decreased by increasing the activity or the steady-state level of a LPSS polypeptide having an amino acid sequence with at least 90% identity with an amino acid sequence selected from the group consisting of the amino acid sequences depicted in SEQ ID NOs:2, 3, 4, 6, 7, 8, 9, 10, 11, 19, 20, 23, 24 and 25. More preferably, the permeability is decreased by increasing the activity or the steady-state level of a LPSS polypeptide selected from the groups consisting of downregulated secreted factors (SEQ ID NOs: 2, 3, 4 and 23), downregulated signal transduction pathways (SEQ ID NO:6, 7, 8, 9, 10 and 11), differentially upregulated signal transduction pathways (SEQ ID NO:19), downregulated receptors and adhesion molecules (SEQ ID NO:20), and differentially upregulated metabolic enzymes (SEQ ID NOs:23-25). The activity or the steady-state level of the LPSS polypeptide may be increased by any of the means described above, e.g., by introducing an expression vector into the endothelial cells, whereby the expression vector comprises a nucleotide sequence encoding the LPSS polypeptide, and whereby the nucleotide sequence is under control of a promoter capable of driving expression of the nucleotide sequence in the endothelial cells.

Alternatively, in the method of the invention, the permeability of the endothelial cells may be decreased by decreasing the activity or the steady-state level of a LPSS polypeptide having an amino acid sequence with at least 90% identity with an amino acid sequence selected from the group consisting of the amino acid sequences depicted in SEQ ID NOs:1, 5, 12, 13, 14, 15, 16, 17, 18, 21 and 22. More preferably, the permeability is decreased by decreasing the activity or the steady-state level of a LPSS polypeptide selected from the groups consisting of upregulated secreted factors (SEQ ID NOs:1, 13, 14 and 22), upregulated signal transduction pathways (SEQ ID NOs:5, 12, 15, 16 and 17), differentially downregulated signal transduction pathways (SEQ ID NO:18), and upregulated receptors and adhesion molecules (SEQ ID NOs: 21 and 22). The activity or the steady-state level of the LPSS polypeptide may be decreased by any of the means described above, e.g., the activity or the steady-state level of the LPSS polypeptide may be decreased by introducing an expression vector into the endothelial cells, whereby the expression vector comprises an antisense nucleotide sequence that is capable of inhibiting the expression of the nucleotide sequence encoding the LPSS polypeptide, and whereby the antisense nucleotide sequence is under control of a promoter capable of driving expression of the antisense nucleotide sequence in the endothelial cells.

In the method of the invention, the permeability of the endothelial cells may be increased by increasing the activity or the steady-state level of a LPSS polypeptide having an amino acid sequence with at least 90% identity with an amino acid sequence selected from the group consisting of the amino acid sequences depicted in SEQ ID NOs:1, 5, 12, 13, 14, 15, 16, 17, 18, 21 and 22. More preferably, the permeability is decreased by decreasing the activity or the steady-state level of a LPSS polypeptide selected from the groups consisting of upregulated secreted factors (SEQ ID NOs:1, 13, 14 and 22), upregulated signal transduction pathways (SEQ ID NOs:5, 12, 15, 16 and 17), differentially downregulated signal transduction pathways (SEQ ID NO:18), and upregulated receptors and adhesion molecules (SEQ ID NOs:21 and 22). The activity or the steady-state level of the LPSS polypeptide may be increased by any of the means described above, e.g., by introducing an expression vector into the endothelial cells, whereby the expression vector comprises a nucleotide sequence encoding the LPSS polypeptide, and whereby the nucleotide sequence is under control of a promoter capable of driving expression of the nucleotide sequence in the endothelial cells.

Alternatively, in the method of the invention, the permeability of the endothelial cells may be increased by decreasing the activity or the steady-state level of a LPSS polypeptide having an amino acid sequence with at least 90% identity with an amino acid sequence selected from the group consisting of the amino acid sequences depicted in SEQ ID NOs:2, 3, 4, 6, 7, 8, 9, 10, 11, 19, 20, 23, 24 and 25. More preferably, the permeability is decreased by increasing the activity or the steady-state level of a LPSS polypeptide selected from the groups consisting of downregulated secreted factors (SEQ ID NOs:2, 3, 4 and 23), downregulated signal transduction pathways (SEQ ID NO:6, 7, 8, 9, 10 and 11), differentially upregulated signal transduction pathways (SEQ ID NO:19), downregulated receptors and adhesion molecules (SEQ ID NO:20), and differentially upregulated metabolic enzymes (SEQ ID NOs:23-25). The activity or the steady-state level of the LPSS polypeptide may be decreased by any of the means described above, e.g., the activity or the steady-state level of the LPSS polypeptide may be decreased by introducing an expression vector into the endothelial cells, whereby the expression vector comprises an antisense nucleotide sequence that is capable of inhibiting the expression of the nucleotide sequence encoding the LPSS polypeptide, and whereby the antisense nucleotide sequence is under control of a promoter capable of driving expression of the antisense nucleotide sequence in the endothelial cells.

Treatment or Prevention of Microvascular Permeability-Modifying Disorders

In another aspect, the invention relates to a method for treating or preventing a microvascular permeability-modifying disorder in a subject. The method comprises pharmacologically altering the activity or the steady-state level in the subject's microvascular endothelial cells, of a LPSS polypeptide having an amino acid sequence with at least 90% identity with an amino acid sequence as depicted in SEQ ID NOs:1-25. Preferably, the alteration is sufficient to reduce the symptoms of the microvascular permeability-modifying disorder. The method preferably comprises administering to the subject in a therapeutically effective amount, a pharmaceutical composition comprising a LPSS polypeptide having an amino acid sequence with at least 90% identity with an amino acid sequence as depicted in SEQ ID NOs:1-25, or a nucleic acid molecule comprising a nucleotide sequence encoding the LPSS polypeptide or another entity that is effective in modifying the activity or steady state level of a LPSS polypeptide as listed herein above. Preferably, in the method the LPSS polypeptide is a polypeptide having an amino acid sequence with at least 90% identity with an amino acid sequence selected from the group consisting of the amino acid sequences depicted in SEQ ID NOs:2, 3, 4, 6, 7, 8, 9, 10, 11, 19, 20, 23, 24 and 25. More preferably, the permeability is decreased by increasing the activity or the steady-state level of a LPSS polypeptide selected from the groups consisting of downregulated secreted factors (SEQ ID NOs:2, 3, 4 and 23), downregulated signal transduction pathways (SEQ ID NO:6, 7, 8, 9, 10 and 11), differentially upregulated signal transduction pathways (SEQ ID NO:19), downregulated receptors and adhesion molecules (SEQ ID NO:20), and differentially upregulated metabolic enzymes (SEQ ID NOs:23-25). The nucleic acid molecule preferably is a gene therapy vector, in which the nucleotide sequence is under control of a promoter capable of driving expression of the nucleotide sequence in endothelial cells, preferably microvascular endothelial cells.

Alternatively, the method of treatment is a method comprising the step of administering to the subject in a therapeutically effective amount, a pharmaceutical composition comprising an antagonist of a LPSS polypeptide having an amino acid sequence with at least 90% identity with an amino acid sequence selected from the group consisting of the amino acid sequences depicted in SEQ ID NOs:1, 5, 12, 13, 14, 15, 16, 17, 18, 21 and 22, whereby preferably the antagonist is an antibody against the LPSS polypeptide. More preferably the amino acid sequence is selected from the groups consisting of upregulated secreted factors (SEQ ID NOs:1, 13, 14 and 22), upregulated signal transduction pathways (SEQ ID NOs:5, 12, 15, 16 and 17), differentially downregulated signal transduction pathways (SEQ ID NO:18), and upregulated receptors and adhesion molecules (SEQ ID NOs:21 and 22). The same effect may be achieved in a method comprising the step of administering to the subject in a therapeutically effective amount, a pharmaceutical composition comprising a gene therapy vector. The gene therapy vector preferably comprises an antisense nucleotide sequence that is capable of inhibiting the expression of the nucleotide sequence encoding a LPSS polypeptide having an amino acid sequence with at least 90% identity with an amino acid sequence selected from the group consisting of the amino acid sequences depicted in SEQ ID NOs:1, 5, 12, 13, 14, 15, 16, 17, 18, 21 and 22, and whereby the antisense nucleotide sequence is under control of a promoter capable of driving expression of the antisense nucleotide sequence in endothelial cells, preferably microvascular endothelial cells. More preferably the amino acid sequence is selected from the groups consisting of upregulated secreted factors (SEQ ID NOs:1, 13, 14 and 22), upregulated signal transduction pathways (SEQ ID NOs:5, 12, 15, 16 and 17), differentially down-regulated signal transduction pathways (SEQ ID NO:18), and upregulated receptors and adhesion molecules (SEQ ID NOs:21 and 22).

In the method of treatment of the invention, the microvascular permeability disorder preferably is selected from the group consisting of neurodegenerative disorders, such as cerebrovascular accidents (CVA), Alzheimer's disease (AD), vascular-related dementia, Creutzfeldt-Jakob disease (CJD), bovine spongiform encephalopathy (BSE), Parkinson's disease (PD), brain trauma, multiple sclerosis (MS), amyotrophic lateral sclerosis (ALS), Huntington's chorea; peripheral disorders with a CNS component, such as septic shock, hepatic encephalopathy, (diabetic) hypertension, diabetic microangiopathy, sleeping sickness, Whipple disease, Duchenne muscular dystrophy (DMD), aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, Gaucher disease, globoid cell leukodystrophy, Krabbe disease, glycogen storage disease II, Pompe disease, GM1-gangliosidosis types 1/11/11I, GM2- gangliosidosis type I, Tay Sachs disease, GM2-gangliosidosis type II, Sandhoff disease, GM2-gangliosidosis, α-mannosidosis types 1/11, mannosidosis, metachromatic leukodystrophy, mucolipidosis type I, sialidosis types 1/11 mucolipidosis types 11/III 1-cell disease, mucolipidosis type IIIC pseudo-Hurler polydystrophy, mucopolysaccharidosis type I, mucopolysaccharidosis type II, Hunter syndrome, mucopolysaccharidosis type IIIA, Sanfilippo syndrome, mucopolysaccharidosis type IIIB, mucopolysaccharidosis type IIIC, mucopolysaccharidosis type IIID, mucopolysaccharidosis type IVA, Morquio syndrome, mucopolysaccharidosis type IVB Morquio syndrome, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, Niemann-Pick disease, Niemann-Pick disease types A/B, C1, or C2, pycnodysostosis, Schindler disease, Schindler disease types VII, and sialic acid storage disease, pre-eclampsia; neuropsychiatric disorders, such as depression, autism, anxiety attention deficit hyperactivity disorder (ADHD), neuropsychiatric systemic lupus erythematosus, bipolar disorder, schizophrenia and other psychoses; other CNS disorders, such as brain tumors, epilepsy, migraine, narcolepsy, insomnia, chronic fatigue syndrome, mountain sickness, encephalitis, meningitis, AIDS-related dementia; and angiogenesis-related disorders, such as vascular tumors, proliferative vitreoretinopathy, rheumatoid arthritis, Crohn's disease, atherosclerosis, ovarian hyperstimulation, psoriasis, endometriosis associated with neovascularization, restenosis subsequent to balloon angioplasty, scar tissue overproduction, peripheral vascular disease, hypertension, inflammatory vasculitides, Reynaud's disease, Reynaud's phenomenon, aneurysms, arterial restenosis, thrombophlebitis, lymphangitis, lymphedema, wound healing and tissue repair, ischemia reperfusion injury, angina, myocardial infarctions, chronic heart conditions, heart failure such as congestive heart failure, age-related macular degeneration, and osteoporosis.

In a further aspect, the invention relates to a method for reversibly increasing the microvascular permeability in a subject. This method comprises the step of administering to the subject, a pharmaceutical composition comprising a LPSS polypeptide having an amino acid sequence with at least 90% identity with an amino acid sequence as depicted in SEQ ID NOs:1-25, or a nucleic acid molecule comprising a nucleotide sequence encoding the LPSS polypeptide, or another entity that is effective in modifying the activity or steady state level of a LPSS polypeptide as listed herein above, in an amount effective to increase the microvascular permeability. Preferably, the LPSS polypeptide is a polypeptide having an amino acid sequence with at least 90% identity with an amino acid sequence selected from the group consisting of the amino acid sequences depicted in SEQ ID NOs:1, 5, 12, 13, 14, 15, 16, 17, 18, 21 and 22. More preferably the amino acid sequence is selected from the groups consisting of upregulated secreted factors (SEQ ID NOs:1, 13, 14 and 22), upregulated signal transduction pathways (SEQ ID NOs:5, 12, 15, 16 and 17), differentially downregulated signal transduction pathways (SEQ ID NO:18), and upregulated receptors and adhesion molecules (SEQ ID NOs:21 and 22). Preferably the nucleic acid molecule is a gene therapy vector, in which the nucleotide sequence is under control of a promoter capable of driving expression of the nucleotide sequence in endothelial cells, preferably microvascular endothelial cells. In this method, the reversibility of the increase in permeability of the microvascular permeability is preferably achieved by using a gene therapy vector that is capable of only transient expression of the nucleotide sequence (see below), and/or, the promoter capable of driving expression of the nucleotide sequence in endothelial cells, preferably is an inducible promoter. More preferably, the inducible promoter is a promoter that may be induced by the administration of small organic or inorganic compounds (see below).

Alternatively, method for reversibly increasing the microvascular permeability in a subject may also be a method comprising the step of administering to the subject in a therapeutically effective amount, a pharmaceutical composition comprising an antagonist of a LPSS polypeptide having an amino acid sequence with at least 90% identity with an amino acid sequence selected from the group consisting of the amino acid sequences depicted in SEQ ID NOs:2, 3, 4, 6, 7, 8, 9, 10, 11, 19, 20, 23, 24 and 25, whereby the antagonist preferably is an antibody against the LPSS polypeptide. More preferably, the amino acid sequence is selected from the groups consisting of downregulated secreted factors (SEQ ID NOs:2, 3, 4 and 23), downregulated signal transduction pathways (SEQ ID NO:6, 7, 8, 9, 10 and 11), differentially upregulated signal transduction pathways (SEQ ID NO:19), downregulated receptors and adhesion molecules (SEQ ID NO:20), and differentially upregulated metabolic enzymes (SEQ ID NOs:23-25). Similarly, the method may also comprise the step of administering to the subject in a therapeutically effective amount, a pharmaceutical composition comprising a gene therapy vector, whereby the gene therapy vector comprises an antisense nucleotide sequence that is capable of inhibiting the expression of the nucleotide sequence encoding a LPSS polypeptide having an amino acid sequence with at least 90% identity with an amino acid sequence selected from the group consisting of the amino acid sequences depicted in SEQ ID NOs:2, 3, 4, 6, 7, 8, 9, 10, 11, 19, 20, 23, 24 and 25, and whereby the antisense nucleotide sequence is under control of a promoter capable of driving expression of the antisense nucleotide sequence in endothelial cells, preferably microvascular endothelial cells. More preferably, the amino acid sequence is selected from the groups consisting of downregulated secreted factors (SEQ ID NOs:2, 3, 4 and 23), downregulated signal transduction pathways (SEQ ID NOs:6, 7, 8, 9, 10 and 11), differentially upregulated signal transduction pathways (SEQ ID NO:19), down-regulated receptors and adhesion molecules (SEQ ID NO:20), and differentially upregulated metabolic enzymes (SEQ ID NOs:23-25).

The methods for reversibly increasing the microvascular permeability in a subject may advantageously be applied when one wants to deliver blood-borne, membrane-impermeant drugs to the brain. The drug may be any pharmaceutically, veterinarily or diagnostically useful compound or composition of compounds, which is normally impermeant to the blood-brain or other physiological barrier or at least insufficiently permeant. The pharmacological nature of the drug is otherwise unimportant. The invention is therefore useful in the delivery of a wide range of drugs across physiological barriers such as the blood-brain barrier. However, it is anticipated that among the primary candidates for delivery by means of this aspect of the invention will be: anti-tumor compounds, such as methotrexate, adriamycin, cisplatin and the other antineoplastic agents or cytotoxic drugs that are defined herein below (see e.g., pages 24-27); growth factors, such as NGF, RDNF and CNTF, which are used to treat neurodegenerative disease; imaging agents, especially those that are antibody based; and neurotransmitter antagonists or agonists which do not penetrate the blood-brain barrier (such as certain NMDA receptor blockers)

For most countries other than the USA, in a further aspect the invention relates to various uses of the compounds of the invention for the manufacture of a medicament for treating or preventing a microvascular permeability-modifying disorder. For example, in one such aspect the invention relates to the use of a LPSS polypeptide having an amino acid sequence with at least 90% identity with an amino acid sequence as depicted in SEQ ID NOs:1-25, or a nucleic acid molecule comprising a nucleotide sequence encoding the LPSS polypeptide, or another entity that is effective in modifying the activity or steady state level of a LPSS polypeptide as listed herein above, for the manufacture of a composition for treating or preventing a microvascular permeability-modifying disorder. Preferably, the LPSS polypeptide is a polypeptide having an amino acid sequence with at least 90% identity with an amino acid sequence selected from the group consisting of the amino acid sequences depicted in SEQ ID NOs:2, 3, 4, 6, 7, 8, 9, 10, 11, 19, 20, 23, 24 and 25. More preferably, the amino acid sequence is selected from the groups consisting of downregulated secreted factors (SEQ ID NOs:2, 3, 4 and 23), downregulated signal transduction pathways (SEQ ID NO:6, 7, 8, 9, 10 and 11), differentially upregulated signal transduction pathways (SEQ ID NO:19), down-regulated receptors and adhesion molecules (SEQ ID NO:20), and differentially upregulated metabolic enzymes (SEQ ID NOs:23-25). The nucleic acid molecule preferably is a gene therapy vector comprising the nucleotide sequence, whereby the nucleotide sequence is under control of a promoter capable of driving expression of the nucleotide sequence in endothelial cells. An antagonist of a LPSS polypeptide having an amino acid sequence with at least 90% identity with an amino acid sequence selected from the group consisting of the amino acid sequences depicted in SEQ ID NOs:1, 5, 12, 13, 14, 15, 16, 17, 18, 21 and 22, may also be used for the manufacture of a composition for treating or preventing a microvascular permeability-modifying disorder, whereby the antagonist preferably is an antibody against the LPSS polypeptide. More preferably the amino acid sequence is selected from the groups consisting of upregulated secreted factors (SEQ ID NOs:1, 13, 14 and 22), upregulated signal transduction pathways (SEQ ID NOs:5, 12, 15, 16 and 17), differentially downregulated signal transduction pathways (SEQ ID NO:18), and upregulated receptors and adhesion molecules (SEQ ID NOs: 21 and 22).

Alternatively, a gene therapy vector comprising an antisense nucleotide sequence that is capable of inhibiting the expression of the nucleotide sequence encoding a LPSS polypeptide having an amino acid sequence with at least 90% identity with an amino acid sequence selected from the group consisting of the amino acid sequences depicted in SEQ ID NOs:1, 5, 12, 13, 14, 15, 16, 17, 18, 21 and 22, and whereby the antisense nucleotide sequence is under control of a promoter capable of driving expression of the antisense nucleotide sequence in endothelial cells, preferably microvascular endothelial cells, may be used for the manufacture of a composition for treating or preventing a microvascular permeability-modifying disorder. More preferably the amino acid sequence is selected from the groups consisting of upregulated secreted factors (SEQ ID NOs:1, 13, 14 and 22), upregulated signal transduction pathways (SEQ ID NOs:5, 12, 15, 16 and 17), differentially downregulated signal transduction pathways (SEQ ID NO:18), and upregulated receptors and adhesion molecules (SEQ ID NOs:21 and 22).

In the above uses of the compounds of the invention for the manufacture of a medicament for treating a microvascular permeability-modifying disorder, the disorder preferably is a microvascular permeability-modifying disorder as described above.

Similarly, for most countries other than the USA, in a yet further aspect the invention relates to various uses of the compounds of the invention for the manufacture of a medicament or composition for reversibly increasing the microvascular permeability in a subject. Preferably the compound is a LPSS polypeptide having an amino acid sequence with at least 90% identity with an amino acid sequence as depicted in SEQ ID NOs:1-25, or a nucleic acid molecule comprising a nucleotide sequence encoding the LPSS polypeptide or another entity that is effective in modifying the activity or steady state level of a LPSS polypeptide as listed herein above. Preferably, the LPSS polypeptide is a polypeptide having an amino acid sequence with at least 90% identity with an amino acid sequence selected from the group consisting of the amino acid sequences depicted in SEQ ID NOs:1, 5, 12, 13, 14, 15, 16, 17, 18, 21 and 22. More preferably the amino acid sequence is selected from the groups consisting of upregulated secreted factors (SEQ ID NOs:1, 13, 14 and 22), upregulated signal transduction pathways (SEQ ID NOs:5, 12, 15, 16 and 17), differentially downregulated signal transduction pathways (SEQ ID NO:18), and upregulated receptors and adhesion molecules (SEQ ID NOs:21 and 22). The nucleic acid molecule preferably is a gene therapy vector, in which the nucleotide sequence encoding the LPSS polypeptide is under control of a promoter capable of driving expression of the nucleotide sequence in endothelial cells, preferably microvascular endothelial cells.

Alternatively, an antagonist of a LPSS polypeptide having an amino acid sequence with at least 90% identity with an amino acid sequence selected from the group consisting of the amino acid sequences depicted in SEQ ID NOs:2, 3, 4, 6, 7, 8, 9, 10, 11, 19, 20, 23, 24 and 25, may be used for the manufacture of a composition for reversibly increasing the microvascular permeability in a subject, whereby preferably the antagonist is an antibody against the LPSS polypeptide. More preferably, the amino acid sequence is selected from the groups consisting of downregulated secreted factors (SEQ ID NOs:2, 3, 4 and 23), downregulated signal transduction pathways (SEQ ID NO:6, 7, 8, 9, 10 and 11), differentially upregulated signal transduction pathways (SEQ ID NO:19), downregulated receptors and adhesion molecules (SEQ ID NO:20), and differentially upregulated metabolic enzymes (SEQ ID NOs:23-25). Or a gene therapy vector comprising an antisense nucleotide sequence that is capable of inhibiting the expression of the nucleotide sequence encoding a LPSS polypeptide having an amino acid sequence with at least 90% identity with an amino acid sequence selected from the group consisting of the amino acid sequences depicted in SEQ ID NOs:2, 3, 4, 6, 7, 8, 9, 10, 11, 19, 20, 23, 24 and 25, and whereby the antisense nucleotide sequence is under control of a promoter capable of driving expression of the antisense nucleotide sequence in endothelial cells, preferably microvascular endothelial cells, may be used for the manufacture of a composition for reversibly increasing the microvascular permeability in a subject. More preferably, the amino acid sequence is selected from the groups consisting of downregulated secreted factors (SEQ ID NOs:2, 3, 4 and 23), downregulated signal transduction pathways (SEQ ID NO:6, 7, 8, 9, 10 and 11), differentially upregulated signal transduction pathways (SEQ ID NO:19), downregulated receptors and adhesion molecules (SEQ ID NO:20), and differentially upregulated metabolic enzymes (SEQ ID NOs:23-25). Preferably the gene therapy vector is a vector for transient expression (see below) and/or the promoter preferably is an inducible promoter. More preferably, the inducible promoter is a promoter that may be induced by the administration of small organic or inorganic compounds (see below).

Targeting to the Microvascular Endothelial Barrier

In yet another aspect, the invention involves a method of treating or diagnosing a CNS or microvascular disorder by administering a therapeutic or diagnostic agent, e.g., a neuroactive agent, by targeting that agent, or its pharmaceutically acceptable carrier, to a LPSS polypeptide having an amino acid sequence with at least 90% identity with an amino acid sequence as depicted in SEQ ID NOs:1-25, to a patient suffering from or at risk for developing the CNS or microvascular disorder. Preferably, the neuroactive agent or its carrier is targeted to an upregulated LPSS polypeptide having an amino acid sequence with at least 90% identity with an amino acid sequence as depicted in SEQ ID NOs:1, 5, 12, 13, 14, 15, 16, 17, 18, 19, 21-25. More preferably, the amino acid sequence is selected from the groups consisting of the amino acid sequences of upregulated secreted factors (SEQ ID NOs:1, 13, 14 and 22), upregulated signal transduction pathways (SEQ ID NOs:5, 12, 15, 16, 17 and 19), upregulated receptors and adhesion molecules (SEQ ID NOs:21 and 22), and upregulated metabolic enzymes (SEQ ID NOs:23-25). Still more preferably an upregulated LPSS polypeptide having an amino acid sequence with at least 90% identity with an amino acid sequence as depicted in SEQ ID NOs:21 or 22.

The targeting agent can be an antibody to a LPSS polypeptide, a protein, a peptide, a LPSS polypeptide agonist, a LPSS polypeptide antagonist, a peptidomimetic, a small molecule, or another compound that specifically binds to a LPSS polypeptide. As used herein, the term "specific binding" means binding that is measurably different from a non-specific interaction. Specific binding can be measured, for example, by determining binding of a molecule compared to binding of a control molecule, which generally is a molecule of similar structure that does not have binding activity, for example, a peptide of similar size that lacks a specific binding sequence. Specific binding is present if the molecule has measurably higher affinity for the LPSS polypeptide than the control molecule. Specificity of binding can be determined, for example, by competition with a control molecule that is known to bind to a target. The term "specific binding," as used herein, includes both low and high affinity specific binding. Specific binding can be exhibited, e.g., by a low affinity targeting agent having a Kd of at least about $10^{-4}$ M. E.g., if a LPSS polypeptide has more than one binding site for a targeting agent, a targeting agent having low affinity can be useful for targeting the microvascular endothelium. Specific binding also can be exhibited by a high affinity targeting agents, e.g., a targeting agent having a Kd of at least about of $10^{-7}$M, at least about $10^{-8}$M, at least about $10^{-9}$M, at least about $10^{-10}$M, or can have a Kd of at least about $10^{-11}$M or $10^{-12}$M or greater. Both low and high affinity-targeting agents are useful for targeting the microvascular endothelium.

The targeting agent is preferably conjugated to the therapeutic agent or its pharmaceutically acceptable carrier. A "conjugate" is herein defined as consisting of two entities that are covalently coupled together. In the context of the present invention the first entity will usually be a targeting agent as herein defined above, whereas the second entity may be a therapeutic or diagnostic moiety, such as a molecule or structure, for use in the treatment or diagnosis of a CNS or microvascular disorder. Such therapeutic or diagnostic moieties may e.g., be anti-tumor compounds, such as antineoplastic agents or cytotoxic drugs, such as alkylating agents, e.g., Mechlorethamine hydrochloride (Nitrogen Mustard, Mustargen, HN2), Cyclophosphamide (Cytovan®, Endoxana®), Ifosfamide (IFEX®), Chlorambucil (Leukeran®), Melphalan (Phenylalanine Mustard, L-sarcolysin, Alkeran®, L-PAM), Busulfan (Myleran®), Thiotepa (Triethylenethiophosphoramide), Carmustine (BiCNU, BCNU), Lomustine (CeeNU, CCNU), Streptozocin (Zanosar®) and the like; plant alkaloids, e.g., Vincristine (Oncovin®), Vinblastine (Velban®, Velbe®), Paclitaxel (Taxol®), and the like; antimetabolites, e.g., methotrexate (MTX), Mercaptopurine (Purinethol®, 6-MP), Thioguanine (6-TG), Fluorouracil (5-FU), Cytarabine (Cytosar-U®®, Ara-C), Azacitidine (Mylosar®, 5-AZA) and the like; antibiotics, e.g., Dactinomycin (Actinomycin D, Cosmegen®), Doxorubicin (Adriamycin®), Daunorubicin (Daunomycin®, Cerubidine®), Idarubicin (Idamycin®), Bleomycin (Blenoxane®), Picamycin (Mithramycin®, Mithracin®), Mitomycin (Mutamycin®) and the like, and other anticellular proliferative agents, e.g., Hydroxyurea (Hydrea®), Procarbazine (Mutalane®), Dacarbazine (DTIC-Dome®), cisplatin (Platinol®), Carboplatin (Paraplatin®), Asparaginase (Elspar®), Etoposide (VePesid®, VP-16-213), Amsarcrine (AMSA, m-AMSA), Mitotane (Lysodren®), Mitoxantrone (Novatrone®), and the like; gefitinib (ZD1839 or Iressa®) and imatinib mesylate (Gleevec® or Glivec®); anti-cancer biopharmaceutical drugs including antibodies (Rituxan® or rituximab; Herceptin® or trastuzumab; Zevalin® or ibritumomab tiuxetan (radiolabeled); Erbitux® or cetuximab; Avastin™ or bevacizumab or rhuMAb-VEGF) and cytokines (Intron® or α-interferon; Proleukin® IL-2 or aldesleukin) to treat primary brain tumors or brain metastasis of somatic tumors; anti-inflammatory drugs including antibodies (Enbrel® or etanercept; Remicade® or infliximab; Simulect® or basiliximab; Zenapax® or daclizumab; Kineret® or anakinra; Xolair® or omalizumab; Humira® or adalimumab; Antegren® or natalizumab; RhuFab™ or ranibizumab; Raptiva™ or efalizumab) and cytokines such as interferon-α, interferon-beta (Avonex® or interferon beta-1a; Betaseron®/Betaferon® or interferon β-1b; Rebif® or interferon-beta-1a), interferon-γ, interleukin 1 (IL-1), interleukin 2 (IL-2), interleukin 3 (IL-3), interleukin 4 (IL-4), interleukin 5 (IL-5), interleukin 6 (IL-6), TNF, granulocyte macrophage colony stimulating factor (GM-CSF: Leukine® or sargramostim), granulocyte colony stimulating factor (G-CSF: Neupogen® or filgrastim), macrophage colony stimulating factor (M-CSF), platelet-derived growth factor (PDGF); to treat e.g., neuroinflammation related to neurodegenerative disorders; neurotrophic factors (e.g., NGF or nerve growth factor; BDNF or brain-derived neurotrophic factor; NT3 or neurotrophin-3; NT4 or neurotrophin-4; NT5 or neurotrophin-5; RDGF or retina-derived growth factor; CNTF or ciliary neurotrophic factor; activin; bFGF or basic fibroblast growth factor; aFGF or acidic fibroblast growth factor; GDNF or glial cell line-derived neurotrophic factor or neublastin or artemin or enovin, presephin, neurturin; CTGF or connective tissue growth factor; EGF or epithelial growth factor); erythropoietins (EPO) (Procrit®/Eprex® or erythropoietin alfa; Epogen® or erythropoietin; NeoRecormon® or erythropoietin β; Aranesp® or darbepoietin alfa); growth hormone or somatotropin (Humatrope®; Protropin®/Nutropin®; Serostim®; Saizen®); anti-NogoA Mab (IN-1); NogoA antagonist of Nogo66 inhibitor (NEP1-40), to treat e.g., neurodegenerative disorders; enzymes (e.g., Cerezyme® or glucocerebrosidase; Aldurazyme™ or laronidase; Aryplase™ or arylsulfatase B; 12S or iduronate-2-sulfatase; α-L-iduronidase; N-acetylgalactosamine 4-sulfatase; phenylase; aspartylglucosaminidase; acid lipase; cysteine transporter; Lamp-2; a galactosidase A; acid ceramidase; α-L-fucosidase; ss-hexosaminidase A; GM2-activator deficiency; α-D-mannosidase; ss-D-mannosidase; arylsulfatase A; saposin B; neuraminidase; α-N-acetylglucosaminidase phosphotransferase; phosphotransferase 7-subunit; heparan-N-sulfatase; α-N-acetylglucosaminidase; acetyl-CoA: N-acetyltransferase; N-acetylglucosamine 6-sulfatase; galactose 6-sulfatase; 0-galactosidase; hyaluronoglucosaminidase; multiple sulfatases; palmitoyl protein thioesterase; tripeptidyl peptidase I; acid sphingomyelinase; cholesterol trafficking; cathepsin K; α-galactosidase B; sialic acid transporter; SOD or Cu/Zn superoxide dismutase) to treat e.g., (neurological symptoms related to) lysosomal storage diseases or other neurodegenerative disorders; brain-acting hormones and neurotransmitters such as somatostatin, oxytocin, vasopressin, guaranine, VIP, adrenocorticotropic hormone (ACTH), cholecystokinin (CCK), substance-P, bombesin, motilin, glicentin, glucagon, glucagon-like peptide (GLP-1); and neuropeptides and derivatives thereof such as peptide YY (PYY), neuropeptide Y (NPY), pancreatic polypeptide (PP), neurokinin A, neurokinin B, endorphin, enkephalin, neurotensin, neuromedin K, neuromedin L, calcitonin related peptide (CGRP), endothelin, ANP ("atrial natriuretic peptide"), BNP ("brain natriuretic peptide"), CNP (C-type natriuretic peptide"), and PACAP ("pituitary adenylate cyclase activating peptide"); imaging agents, especially those that are antibody based; neurotransmitter antagonists or agonists which do not penetrate the blood-brain barrier (such as certain NMDA receptor blockers); antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; beta.-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4diaminopyrimidines, nitrofurans, quinolones and analogs thereof, sulfonamides, sulfones; antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazole, e.g., fluconazole, itraconazole, terconazole; anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.; antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinine, quinine, quinocide, quinine, dibasic sodium arsenate; antiprotozoal agents, such as: acranil, timidazole, ipronidazole, ethylstibamine, pentamidine, acetarsone, aminitrozole, anisomycin, nifuratel, timidazole, benzidazole, suramin, and the like; genes (including expression vectors and/or promoters, preferably the GFAP- and/or γ-GTP promoters) encoding for polypeptides (preferably for Neprilysin and the proteins, peptides, enzymes, cytokines, interleukins, hormones and growth factors described herein above) or antisense DNA for polypeptides; and antisense probes (nucleic acids or peptide nucleic acids). In addition to direct conjugation between the therapeutic or diagnostic moieties and the targeting agent, such therapeutic or diagnostic moieties may be encapsulated within nanocontainers, such as nanoparticles, liposomes or nanogels, where the targeting agent is preferably covalently coupled to such a nanocontainer. Such conjugation to the nanocontainer may be either directly or via any of the well-known polymeric conjugation agents such as sphingomyelin, polyethylene glycol (PEG) or other organic polymers, and either with a single targeting agent or in combination with any of the well-known blood-brain barrier targeting moieties against the insulin, transferrin, IGF, leptin, LRP (1B) or LDL receptor on the blood-brain barrier and brain cell membrane. Details of producing such pharmaceutical compositions comprising targeted (PEG) liposomes are described in U.S. Pat. No. 6,372,250.

A large variety of methods for conjugation of targeting agents with therapeutic or diagnostic moieties are known in the art. Such methods are e.g., described in Hermanson (1996, *Bioconjugate Techniques*, Academic Press; U.S. Pat. No. 6,180,084 and U.S. Pat. No. 6,264,914, and include, e.g., methods used to link haptens to carriers proteins as routinely used in applied immunology (see Harlow and Lane, 1988, *Antibodies: A Laboratory Manual*, Cold Spring Harbor Laboratory Press, Cold Spring Harbor, N.Y.). It is recognized that, in some cases, a targeting agent or a therapeutic or diagnostic moiety may lose efficacy or functionality upon conjugation depending, e.g., on the conjugation procedure or the chemical group utilized therein. However, given the large variety of methods for conjugation the skilled person is able to find a conjugation method that does not or least affects the efficacy or functionality of the entities to be conjugated.

Suitable methods for conjugation of a targeting agent with a therapeutic or diagnostic moiety include e.g., carbodiimide conjugation (Bauminger and Wilchek, 1980, *Meth. Enzymol.* 70: 151-9). Alternatively, a moiety can be coupled to a targeting agent as described by Nagy et al., *Proc. Natl. Acad. Sci. USA* 93:7269-73 (1996); and Nagy et al., *Proc. Natl. Acad. Sci. USA* 95:1794-99 (1998), each of which is incorporated herein by reference. Another method for conjugating that may suitable be used are e.g., sodium periodate oxidation followed by reductive alkylation of appropriate reactants and glutaraldehyde crosslinking.

A particularly advantageous method of conjugation may be applied when both the targeting agent and the therapeutic moiety are (poly)peptides. In such instances the two entities may be synthesized as a single (poly)peptide chain comprising the amino acid sequences of both the targeting agent and the therapeutic peptide. When the sum of the amino acid sequences of the targeting agent and the therapeutic peptide does not exceed 50, 80 or 100 amino acids the conjugate may be synthesized by solid phase peptide synthesis as herein described above. Alternatively, when the sum of the amino acid sequences is larger the single (poly)peptide chain comprising the targeting agent and the therapeutic peptide may be produced by recombinant expression techniques as outlined herein below. In such instances e.g., the two nucleic acid sequences encoding each the targeting agent and the therapeutic peptide may be operably linked in frame to form a single open reading frame. The nucleic acid sequence containing the single open reading frame may then be inserted in a suitable expression vector for expression in a suitable host from which the conjugate may then be recovered and optionally further purified as herein described below. In these methods, targeting peptides may be placed on either or both ends of the therapeutic peptide, or may be inserted within the amino acid sequence of the therapeutic peptide in one or more positions that do not disturb the function or efficacy of the respective peptides. Using routine methods the skilled person can establish the optimal position of the targeting peptide(s) with respect to the therapeutic peptide.

Diagnosis of Microvascular Permeability

In a further aspect the invention relates to methods for diagnosing the status of the microvascular permeability in a subject. Such a method preferably comprises the steps of: (a) determining the expression level of a nucleic acid sequence encoding a LPSS polypeptide having an amino acid sequence with at least 90% identity with an amino acid sequence as depicted in SEQ ID NOs:1-25 in the subject's microvascular endothelium; and, (b) comparing the expression level of the nucleic acid sequence with a reference value for expression level of the nucleic acid sequence, the reference value preferably being the average value for the expression level in the microvascular endothelium of healthy individuals. The expression level of the nucleic acid sequence may be determined indirectly by quantifying the amount of the LPSS polypeptide encoded by the nucleic acid sequence. In a preferred method, the expression level of more than one nucleic acid sequences are compared. When more than one nucleic acid sequence is analyzed this may conveniently be done using microarrays comprising complementary nucleic acids as described below and in the Examples. The expression level may be determined ex vivo in a sample obtained from the subject. The method preferably is a method for diagnosing a microvascular permeability disorder or for diagnosing a susceptibility to a microvascular permeability disorder, whereby the microvascular permeability may be as described above. The method may also be used to assess the efficacy of a treatment for restoration of the microvascular permeability.

Screening for Substances Capable of Modulating Endothelial Permeability

In yet another aspect the invention relates to methods for identification of substances capable of modulating the permeability of microvascular endothelial cells. The method preferably comprises the steps of: (a) providing a test cell population capable of expressing one or more nucleic acid sequences encoding a LPSS polypeptide having an amino acid sequence with at least 90% identity with an amino acid sequence as depicted in SEQ ID NOs:1-25; (b) contacting the test cell population with a composition comprising a substance to be tested; (c) determining the expression level of a nucleic acid sequence encoding a LPSS polypeptide having an amino acid sequence with at least 90% identity with an amino acid sequence as depicted in SEQ ID NOs:1-25, in the test cell population contacted with the substance; (d) comparing the expression of the nucleic acid sequence with the expression level of the nucleic acid sequence in a test cell population that is not contacted with the substance; and, (e) identifying a substance that produces a difference n expression level of the nucleic acid sequence, between the test cell population that is contacted with the substance and the test cell population that is not contacted with the substance. In the method the expression level of the nucleic acid sequence may be determined indirectly by quantifying the amount of the LPSS polypeptide encoded by the nucleic acid sequence. The expression level of more than one nucleic acid sequence may be compared. In a preferred method, the test cell population comprises endothelial cells, preferably vascular endothelial cells, more preferably microvascular endothelial cells, most preferably brain microvascular endothelial cells. The cells in the test cell population are preferably mammalian cells, preferably human cells. Preferably in the method, the test cell population that is contacted with the substance and the test cell population that is not contacted with the substance are derived from one cell population, preferably from one cell line, more preferably from one cell. In a further preferred method, the test cell population is co-cultured with a helper cell population, whereby the test cell population is cultured on one side of the filter and the helper cell population is cultured on the other side of the filter, and whereby the helper cell population preferably comprises astrocytes.

Preferred LPSS Polypeptides for Use in the Methods of the Invention

We disclose herein specifically differentially expressed polypeptides that are involved in decreased vascular permeability. We therefore refer to these polypeptides as "lipopolysaccharide-sensitive" polypeptides or LPSS polypeptides. LPSS polypeptides are involved in several different types of mechanisms involved in the control of blood-brain barrier functionality. These include secreted factors, signal transduction pathways, receptors and adhesion molecules, and metabolic enzymes. LPSS polypeptides and these mechanisms are discussed in greater detail below. If known or applicable, for each LPSS polypeptide the following information is given:

encoding amino acid sequence for the LPSS polypeptide (sequence listing);

receptor, receptor agonist, receptor antagonist;

agonist LPSS polypeptide or fragment(s);

full or partial LPSS polypeptide receptor agonist(s);

agonistic peptidomimetic(s);

agonistic antibodies or antibody fragment(s);

agonistic small molecules, or other drugs;

antagonistic LPSS polypeptide fragment(s);

antagonistic peptidomimetic(s);

antagonistic small molecules, or other drugs;

antagonistic or neutralizing antibodies or antibody fragment(s);

partial or inverse LPSS polypeptide receptor agonists;

full or partial LPSS polypeptide receptor antagonists.

The skilled person will appreciate that each of these entities may be applied in the methods of the invention as herein described.

Secreted Polypeptides

Extracellularly secreted or operational LPSS polypeptides (like hormones, enzymes, growth factors, cytokines, chemokines, binding proteins, etc.) are preferably used for specific modulation or monitoring of the permeability of the blood-brain barrier in the embodiments of the present invention. We have identified several of such novel specifically differentially expressed polypeptides, including pre-B-cell colony-enhancing factor, bone morphogenic protein 4, latent transforming growth factor beta binding protein 2, tumor necrosis factor α-induced protein 6, heparin-binding epidermal growth factor-like growth factor (diphtheria toxin receptor) and phospholipase A2, group VII. These are discussed in greater detail below, except for diphtheria toxin receptor (SEQ ID NO:22) and phospholipase A2, group VII (SEQ ID NO:23), which are discussed in different sections (Receptors and adhesion molecules and Metabolic enzymes, respectively).

TABLE 1

"Lipopolysaccharide-sensitive (LPSS)" genes, their SEQ ID NO.'s, LPS effect (up, down, differentially expressed (dif+ or dif−)), their accession no.'s (RefSeq), gene symbols and description (or gene name).

| LPSS NO. | SEQ ID NO. | LPS effect | ACCESSION NO. | GENE SYMBOL | DESCRIPTION |
|---|---|---|---|---|---|
| 01 | 1 | Up | NM_005746 | PBEF | pre-B-cell colony-enhancing factor |
| 02 | 2 | Down | NM_001202 | BMP4 | bone morphogenetic protein 4 |
|  | 3 |  | NM_130850 |  |  |
|  | 4 |  | NM_130851 |  |  |
| 03 | 5 | Up | NM_006910 | RBBP6 | retinoblastoma-binding protein 6 |
| 04 | 6 | Down | NM_172171 | CAMK2G | calcium/calmodulin-dependent protein kinase (CaM kinase) II gamma, isoform 1-6 |
|  | 7 |  | NM_172169 |  |  |
|  | 8 |  | NM_172170 |  |  |
|  | 9 |  | NM_001222 |  |  |
|  | 10 |  | NM_172172 |  |  |
|  | 11 |  | NM_172173 |  |  |
| 05 | 12 | Up | NM_023009 | MACMARCKS | macrophage myristoylated alanine-rich C kinase substrate |
| 06 | 13 | Up | NM_000428 | LTBP2 | latent transforming growth factor beta binding protein 2 |
| 07 | 14 | Up | NM_007115 | TNFAIP6 | tumor necrosis factor, α-induced protein 6 |
| 08 | 15 | Up | NM_014470 | RHO6 | GTP-binding protein RHO6 |
| 09 | 16 | Up | NM_002597 | PDC | phosducin isoform phosducin-like protein |
|  | 17 |  | NM_022576 |  | phosducin isoform phosducin-like orphan 1 |
| 10 | 18 | Dif− | NM_004343 | CALR | calreticulin precursor |
| 11 | 19 | Dif+ | NM_025195 | C8FW | G-protein-coupled receptor induced protein |
| 12 | 20 | Down | NM_003467 | CXCR4 | chemokine (C—X—C motif) receptor 4 |
| 13 | 21 | Up | NM_000163 | GHR | growth hormone receptor |
| 14 | 22 | Up | NM_001945 | DTR | diphtheria toxin receptor (heparin-binding epidermal growth factor-like growth factor) |
| 15 | 23 | Dif+ | NM_005084 | PLA2G7 | phospholipase A2, group VII (platelet-activating factor acetylhydrolase, plasma) |
| 16 | 24 | Dif+ | NM_002970 | SAT | spermidine/spermine N1-acetyltransferase |
| 17 | 25 | Dif+ | NM_003358 | UGCG | ceramide glucosyltransferase |

TABLE 2

LPS responses (average globally scaled intensity values ± standard deviation) of LPSS genes.

| | Control average | stdev | LPS average | stdev | fold-change | direction ($p < 0.05$) |
|---|---|---|---|---|---|---|
| LPSS01 PBEF GeneChip: U133 Code: 217739_s_at pre-B-cell colony-enhancing factor ||||||| 
| BCEC | 1915 | 1 | 3924 | 697 | 2.0 | Up |
| BCEC + astro | 1573 | 551 | 3681 | 266 | 2.3 | Up |
| significant difference between BCEC and BCEC + astro ($p < 0.05$): |  |  |  |  | No |  |
| LPSS02 BMP4 GeneChip: U95 Code: 40333_at bone morphogenetic protein 4 |||||||
| BCEC | 10555 | 3042 | 10605 | 6713 | 1.0 |  |
| BCEC + astro | 16804 | 3820 | 7718 | 3261 | 2.2 | Down |
| significant difference between BCEC and BCEC + astro ($p < 0.05$): |  |  |  |  | No |  |
| LPSS03 RBBP6 GeneChip: U95 Code: 38266_at retinoblastoma binding protein 6 |||||||
| BCEC | 454 | 333 | 593 | 274 | 1.3 |  |
| BCEC + astro | 278 | 128 | 645 | 98 | 2.3 | Up |
| significant difference between BCEC and BCEC + astro ($p < 0.05$): |  |  |  |  | No |  |
| LPSS04 CAMK2G GeneChip: U95 Code: 39388_at calcium/calmodulin-dependent protein kinase (CaM kinase) II gamma |||||||
| BCEC | 4559 | 434 | 4054 | 488 | 1.1 |  |
| BCEC + astro | 7283 | 248 | 3573 | 99 | 2.0 | Down |
| significant difference between BCEC and BCEC + astro ($p < 0.05$): |  |  |  |  | No |  |
| LPSS05 MACMARCKS GeneChip: U133 Code: 200644_at macrophage myristoylated alanine-rich C kinase substrate |||||||
| BCEC | 7701 | 1522 | 15737 | 2884 | 2.0 | Up |
| BCEC + astro | 9719 | 2945 | 19977 | 5523 | 2.1 | Up |
| significant difference between BCEC and BCEC + astro ($p < 0.05$): |  |  |  |  | No |  |

TABLE 2-continued

LPS responses (average globally scaled intensity values ± standard deviation) of LPSS genes.

| | Control average | stdev | LPS average | stdev | fold-change | direction (p < 0.05) |
|---|---|---|---|---|---|---|
| LPSS06 LTBP2 GeneChip: U133 Code: 204682_at latent transforming growth factor beta binding protein 2 | | | | | | |
| BCEC | 1359 | 462 | 1692 | 600 | 1.2 | |
| BCEC + astro | 938 | 409 | 1996 | 125 | 2.1 | Up |
| significant difference between BCEC and BCEC + astro (p < 0.05): | | | | | No | |
| LPSS07 TNFAIP6 GeneChip: U133 Code: 206025_s_at tumor necrosis factor, α-induced protein 6 | | | | | | |
| BCEC | 1306 | 937 | 5156 | 678 | 3.9 | Up |
| BCEC + astro | 879 | 267 | 5057 | 824 | 5.8 | Up |
| significant difference between BCEC and BCEC + astro (p < 0.05): | | | | | No | |
| LPSS08 RHO6 GeneChip: U133 Code: 210056_at GTP-binding protein RHO6 | | | | | | |
| BCEC | 567 | 396 | 3874 | 2460 | 6.8 | Up |
| BCEC + astro | 567 | 515 | 4120 | 1270 | 7.3 | Up |
| significant difference between BCEC and BCEC + astro (p < 0.05): | | | | | No | |
| LPSS08 RHO6 GeneChip: U95 Code: 37785_at GTP-binding protein RHO6 | | | | | | |
| BCEC | 2174 | 306 | 20970 | 12054 | 9.6 | Up |
| BCEC + astro | 1761 | 143 | 23624 | 9452 | 13.4 | Up |
| significant difference between BCEC and BCEC + astro (p < 0.05): | | | | | No | |
| LPSS09 PDC GeneChip: U133 Code: 211496_s_at phosducin isoform phosducin-like protein/orphan 1 | | | | | | |
| BCEC | 539 | 348 | 445 | 275 | 0.8 | |
| BCEC + astro | 289 | 153 | 617 | 143 | 2.1 | Up |
| significant difference between BCEC and BCEC + astro (p < 0.05): | | | | | No | |
| LPSS10 CALR GeneChip: U133 Code: 214316_x_at calreticulin precursor | | | | | | |
| BCEC | 1711 | 491 | 2329 | 924 | 0.7 | |
| BCEC + astro | 2561 | 596 | 970 | 319 | 2.6 | Down |
| significant difference between BCEC and BCEC + astro (p < 0.05): | | | | | Yes | Down |
| LPSS11 C8FW GeneChip: U133 Code: 202241_at G-protein-coupled receptor induced protein | | | | | | |
| BCEC | 1484 | 319 | 2275 | 118 | 1.5 | |
| BCEC + astro | 1290 | 234 | 3065 | 503 | 2.4 | Up |
| significant difference between BCEC and BCEC + astro (p < 0.05): | | | | | Yes | Up |
| LPSS12 CXCR4 GeneChip: U133 Code: 209201_x_at chemokine (C-X-C motif) receptor 4 | | | | | | |
| BCEC | 30942 | 24861 | 10231 | 4598 | 3.0 | |
| BCEC + astro | 34342 | 9281 | 7925 | 1058 | 4.3 | Down |
| significant difference between BCEC and BCEC + astro (p < 0.05): | | | | | No | |
| LPSS12 CXCR4 GeneChip: U133 Code: 211919_s_at chemokine (C-X-C motif) receptor 4 | | | | | | |
| BCEC | 15810 | 12178 | 7424 | 2626 | 2.1 | |
| BCEC + astro | 16792 | 3969 | 6350 | 1470 | 2.6 | Down |
| significant difference between BCEC and BCEC + astro (p < 0.05): | | | | | No | |
| LPSS13 GHR GeneChip: U95 Code: 160030_at growth hormone receptor | | | | | | |
| BCEC | 324 | 177 | 553 | 73 | 1.7 | |
| BCEC + astro | 290 | 225 | 658 | 86 | 2.3 | Up |
| significant difference between BCEC and BCEC + astro (p < 0.05): | | | | | No | |
| LPSS14 DTR GeneChip: U133 Code: 203821_at diphtheria toxin receptor (heparin-binding epidermal growth factor-like growth factor) | | | | | | |
| BCEC | 3631 | 918 | 7200 | 1638 | 2.0 | |
| BCEC + astro | 1562 | 986 | 8230 | 2756 | 5.3 | Up |
| significant difference between BCEC and BCEC + astro (p < 0.05): | | | | | No | |
| LPSS15 PLA2G7 GeneChip: U133 Code: 206214_at phospholipase A2, group VII (platelet-activating factor acetylhydrolase, plasma) | | | | | | |
| BCEC | 508 | 76 | 467 | 190 | 0.9 | |
| BCEC + astro | 370 | 104 | 882 | 88 | 2.4 | Up |
| significant difference between BCEC and BCEC + astro (p < 0.05): | | | | | Yes | Up |

TABLE 2-continued

LPS responses (average globally scaled intensity values ± standard deviation) of LPSS genes.

| | Control average | stdev | LPS average | stdev | fold-change | direction ($p < 0.05$) |
|---|---|---|---|---|---|---|
| LPSS16 SAT GeneChip: U133 Code: 210592_s_at spermidine/spermine N1-acetyltransferase | | | | | | |
| BCEC | 5572 | 2364 | 7717 | 205 | 1.4 | |
| BCEC + astro | 3253 | 614 | 8839 | 580 | 2.7 | Up |
| significant difference between BCEC and BCEC + astro ($p < 0.05$): | | | | | Yes | Up |
| LPSS17 UGCG GeneChip: U95 Code: 40215_at ceramide glucosyltransferase | | | | | | |
| BCEC | 1582 | 318 | 3366 | 382 | 2.1 | Up |
| BCEC + astro | 1862 | 146 | 5173 | 1676 | 2.8 | Up |
| significant difference between BCEC and BCEC + astro ($p < 0.05$): | | | | | Yes | Up |

The PBEF gene (SEQ ID NO:1; LPSS01), encoding pre-B-cell colony-enhancing factor, is upregulated in BCEC after an exposure for 2 hours to LPS in both BCEC monolayers and BCEC-astrocyte cocultures (Table 1 and Table 2). Upregulated LPSS polypeptides are involved in increased vascular permeability. Pre-B-cell colony-enhancing factor is a cytokine that acts on early B-lineage precursor cells. It increases the pre-B-cell colony formation activity of stem cell factor (MGF) and interleukin 7 (IL7). The surprising finding that the PBEF gene, or pre-B-cell colony-enhancing factor, was modified by LPS in the cells that constitute the blood-brain barrier has not been reported earlier and offers new opportunities to modify or monitor blood-brain barrier functionality. Therefore, any agent that changes the biological activity of the PBEF gene product (pre-B-cell colony-enhancing factor) is useful to specifically modulate the permeability of the blood-brain barrier in the embodiments of the present invention. Pre-B-cell colony-enhancing factor activity may be conveniently decreased by antisense inhibition of the PBEF gene, while pre-B-cell colony-enhancing factor activity may be conveniently increased by introduction of the PBEF gene into the cell or by exposure of the endothelial cells to exogenous pre-B-cell colony-enhancing factor. In addition, Ognjanovic et al. (2001, *J Mol. Endocrinol.* 26: 107-17) developed useful antibodies against pre-B-cell colony-enhancing factor, which may be used for diagnostic or treatment purposes. Changes in expression of this gene may be used for diagnostic purposes of vascular permeability status in the embodiments of the present invention. For this purpose both nucleic acids complementary to the PBEF gene as well as antibodies against the PBEF protein may be applied.

The BMP4 gene (SEQ ID NOs:2, 3 and 4; LPSS02), encoding bone morphogenic protein 4, is downregulated in BCEC after an exposure for 2 hours to LPS in BCEC-astrocyte cocultures (Table 1 and Table 2). Downregulated LPSS polypeptides are involved in increased vascular permeability. Bone morphogenic protein 4 (or bone morphogenetic protein 2B (BMP2B or BMP2B1), or ZYME) is a member of the bone morphogenetic protein family which is part of the transforming growth factor-beta superfamily. The superfamily includes large families of growth and differentiation factors. Bone morphogenetic proteins were originally identified by an ability of demineralized bone extract to induce endochondral osteogenesis in vivo in an extraskeletal site. This particular family member plays an important role in the onset of endochondral bone formation in humans, and a reduction in expression has been associated with a variety of bone diseases, including the heritable disorder Fibrodysplasia Ossificans Progressiva. Alternative splicing in the 5' untranslated region of this gene has been described and three variants are described, all encoding an identical protein. The surprising finding that the expression of the BMP4 gene, or bone morphogenic protein 4, was modified by LPS in the cells that constitute the blood-brain barrier has not been reported earlier and offers new opportunities to modify or monitor blood-brain barrier functionality. Therefore, any agent that changes the biological activity of the BMP4 gene product (bone morphogenic protein 4) is useful to specifically modulate the permeability of the blood-brain barrier in the embodiments of the present invention. Bone morphogenic protein 4 activity may be conveniently decreased by antisense inhibition of the BMP4 gene or by exposure of the endothelial cells to the bone morphogenic protein 4 inhibitors noggin or chordin, while bone morphogenic protein 4 activity may be conveniently increased by introduction of the BMP4 gene into the cell or by exposure of the endothelial cells to exogenous bone morphogenic protein 4. In addition, R&D Systems Europe Ltd., UK offers useful antibodies against bone morphogenic protein 4, which may be used for diagnostic or treatment purposes. Changes in expression of this gene may be used for diagnostic purposes of vascular permeability status in the embodiments of the present invention. For this purpose both nucleic acids complementary to the BMP4 gene as well as antibodies against the BMP4 protein may be applied.

The LTBP2 gene (SEQ ID NO:13; LPSS06), encoding latent transforming growth factor beta binding protein 2, is upregulated in BCEC after an exposure for 2 hours to LPS in BCEC-astrocyte cocultures (Table 1 and Table 2). Upregulated LPSS polypeptides are involved in increased vascular permeability. Latent transforming growth factor beta binding protein 2 (formerly known as LTBP3) is involved in binding of tgf-beta in the extracellular-matrix. It serves as an important mechanism to regulate tgf-beta function. Mutations in LTBP2 have been identified in two instances of atypical Marfan Syndrome. The surprising finding that the expression of the LTBP2 gene, or latent transforming growth factor beta binding protein 2, was modified by LPS in the cells that constitute the blood-brain barrier has not been reported earlier and offers new opportunities to modify or monitor blood-brain barrier functionality. Therefore, any agent that changes the biological activity of the LTBP2 gene product (latent transforming growth factor beta binding protein 2) is useful to specifically modulate the permeability of the blood-brain barrier in the embodiments of the present invention. Latent transforming growth factor beta binding protein 2 activity may be conveniently decreased by antisense inhibition of the LTBP2 gene, while latent transforming growth factor beta binding protein 2 activity may be conveniently increased by introduction of the LTBP2 gene into the cell or by exposure of the endothelial cells to exogenous latent transforming growth factor beta binding protein 2. In addition, Elastin Products Company, Inc. (Missouri, USA) offers useful antibodies against latent transforming growth factor beta binding protein 2, which may be used for diagnostic or treatment purposes. Changes in expression of this gene may be used for diagnostic purposes of vascular permeability status in the embodiments of the present invention. For this purpose both nucleic acids complementary to the LTBP2 gene as well as antibodies against the LTBP2 protein may be applied.

The TNFAIP6 gene (SEQ ID NO:14; LPS S07), encoding tumor necrosis factor α-induced protein 6, is upregulated in BCEC after an exposure for 2 hours to LPS in both BCEC monolayers and BCEC-astrocyte cocultures (Table 1 and Table 2). Upregulated LPSS polypeptides are involved in increased vascular permeability. Tumor necrosis factor α-induced protein 6 (or tumor necrosis factor-stimulated gene-6 protein or TSG6, or hyaluronate-binding protein, or tumor necrosis factor-inducible protein 6, or tumor necrosis factor α-inducible protein 6) is a secretory protein that contains a hyaluronan-binding domain, and thus is a member of the hyaluronan-binding protein family. The hyaluronan-binding domain is known to be involved in extracellular matrix stability and cell migration. This protein has been shown to form a stable complex with inter-α-inhibitor (I α I), and thus enhance the serine protease inhibitory activity of I α I, which is important in the protease network associated with inflammation. The expression of this gene can be induced by tumor necrosis factor α, interleukin-1 and LPS in normal fibroblasts, peripheral blood mononuclear cells, synovial cells, and chondrocytes. The expression can also be induced by mechanical stimuli in vascular smooth muscle cells, and is found to be correlated with proteoglycan synthesis and aggregation. TNFAIP6 is similar to the adhesion receptor CD44. The surprising finding that the TNFAIP6 gene, or tumor necrosis factor α-induced protein 6, was modified by LPS in the cells that constitute the blood-brain barrier has not been reported earlier and offers new opportunities to modify or monitor blood-brain barrier functionality. Therefore, any agent that changes the biological activity of the TNFAIP6 gene product (tumor necrosis factor α-induced protein 6) is useful to specifically modulate the permeability of the blood-brain barrier in the embodiments of the present invention. Tumor necrosis factor α-induced protein 6 activity may be conveniently decreased by antisense inhibition of the TNFAIP6 gene or by the use of antibodies against the TNFAIP6 protein, while tumor necrosis factor α-induced protein 6 activity may be conveniently increased by introduction of the TNFAIP6 gene into the cell or by exposure of the endothelial cells to exogenous tumor necrosis factor α-induced protein 6. Changes in expression of this gene may be used for diagnostic purposes of vascular permeability status in the embodiments of the present invention. For this purpose both nucleic acids complementary to the TNFAIP6 gene as well as antibodies against the TNFAIP6 protein may be applied.

Signal Transduction Pathways

Polypeptides involved in intracellular signal transduction pathways are preferably used to specifically modulate the permeability of the blood-brain barrier in the embodiments of the present invention. We have identified several novel of such specifically differentially expressed polypeptides, including retinoblastoma-binding protein 6, calcium/calmodulin-dependent protein kinase (CaM kinase) II gamma, macrophage myristoylated alanine-rich C kinase substrate, GTP-binding protein RHO6, phosducin isoform phosducin-like protein/orphan 1, calreticulin precursor and a G-protein-coupled receptor induced protein. These are discussed in greater detail below.

The RBBP6 gene (SEQ ID NO:5; LPSS03), encoding retinoblastoma-binding protein 6, is upregulated in BCEC after an exposure for 2 hours to LPS in BCEC-astrocyte cocultures (Table 1 and Table 2). Upregulated LPSS polypeptides are involved in increased vascular permeability. Retinoblastoma-binding protein 6 (or RBQ-1 or DKFZp761B2423) is a ubiquitously expressed nuclear protein. It is found among several proteins that bind directly to retinoblastoma protein which regulates cell proliferation. It interacts preferentially with under-phosphorylated retinoblastoma protein. The surprising finding that the expression of the RBBP6 gene, or retinoblastoma-binding protein 6, was modified by LPS in the cells that constitute the blood-brain barrier has not been reported earlier and offers new opportunities to modify or monitor blood-brain barrier functionality. Therefore, any agent that changes the biological activity of the RBBP6 gene product (retinoblastoma-binding protein 6) is useful to specifically modulate the permeability of the blood-brain barrier in the embodiments of the present invention. Retinoblastoma-binding protein 6 activity may be conveniently decreased by antisense inhibition of the RBBP6 gene or by the use of antibodies against the RBBP6 protein, while retinoblastoma-binding protein 6 activity may be conveniently increased by introduction of the RBBP6 gene into the cell or by exposure of the endothelial cells to exogenous retinoblastoma-binding protein 6. Changes in expression of this gene may be used for diagnostic purposes of vascular permeability status in the embodiments of the present invention. For this purpose both nucleic acids complementary to the RBBP6 gene as well as antibodies against the RBBP6 protein may be applied.

The CAMK2G gene (SEQ ID NOs:6, 7, 8, 9, 10 and 11; LPSS04), encoding calcium/calmodulin-dependent protein kinase (CaM kinase) II gamma, is downregulated in BCEC after an exposure for 2 hours to LPS in BCEC-astrocyte cocultures (Table 1 and Table 2). Downregulated LPSS polypeptides are involved in increased vascular permeability. Calcium/calmodulin-dependent protein kinase (CaM kinase) II gamma (or CAMK, CAMKG, CAMK-II, MGC26678) belongs to the Serine/Threonine protein kinase family, and to the Ca(2+)/calmodulin-dependent protein kinase subfamily. Calcium signaling is crucial for several aspects of plasticity at glutamatergic synapses. In mammalian cells the enzyme is composed of four different chains: α, beta, gamma, and delta. The product of this gene is a gamma chain. Six alternatively spliced variants that encode six different isoforms have been characterized to date. Additional alternative splice variants that encode different isoforms have been described, but their full-length nature has not been determined. The surprising finding that the expression of the CAMK2G gene, or calcium/calmodulin-dependent protein kinase (CaM kinase) II gamma, was modified by LPS in the cells that constitute the blood-brain barrier has not been reported earlier and offers new opportunities to modify or monitor blood-brain barrier functionality. Therefore, any agent that changes the biological activity of the CAMK2G gene product (calcium/calmodulin-dependent protein kinase (CaM kinase) II gamma) is useful to specifically modulate the permeability of the blood-brain barrier in the embodiments of the present invention. Calcium/calmodulin-dependent protein kinase (CaM kinase) II gamma activity may be conveniently decreased by antisense inhibition of the CAMK2G gene or by the use of antibodies against the CAMK2G protein, while calcium/calmodulin-dependent protein kinase (CaM kinase) II gamma activity may be conveniently increased by introduction of the CAMK2G gene into the cell or by exposure of the endothelial cells to exogenous calcium/calmodulin-dependent protein kinase (CaM kinase) II gamma. Changes in expression of this gene may be used for diagnostic purposes of vascular permeability status in the embodiments of the present invention. For this purpose both nucleic acids complementary to the CAMK2G gene as well as antibodies against the CAMK2G protein may be applied. In addition, Bui et al. (2000, Cell 100(4): 457-67) generated transgenic mice expressing CaMKIIγB* (T287D), a partially calcium-independent mutant of CaMKIIγB, which may be useful to specifically investigate the blood-brain barrier in the embodiments of the present invention.

The MACMARCKS gene (SEQ ID NO:12; LPSS05), encoding macrophage myristoylated alanine-rich C kinase substrate, is upregulated in BCEC after an exposure for 2 hours to LPS in both BCEC monolayers and BCEC-astrocyte cocultures (Table 1 and Table 2). Upregulated LPSS polypeptides are involved in increased vascular permeability. Macrophage myristoylated alanine-rich C kinase substrate (also known as F52, or MARCKS-like protein or MLP or MLP1, or MARCKS-related protein, MRP) functions in coupling the calmodulin signal transduction and protein kinase C systems. It is involved in central nervous system development. The surprising finding that the MACMARCKS gene, or macrophage myristoylated alanine-rich C kinase substrate, was modified by LPS in the cells that constitute the blood-brain barrier has not been reported earlier and offers new opportunities to modify or monitor blood-brain barrier functionality. Therefore, any agent that changes the biological activity of the MACMARCKS gene product (macrophage myristoylated alanine-rich C kinase substrate) is useful to specifically modulate the permeability of the blood-brain barrier in the embodiments of the present invention. Macrophage myristoylated alanine-rich C kinase substrate activity may be conveniently decreased by antisense inhibition of the MACMARCKS gene or by antibodies against the MACMARCKS protein, while macrophage myristoylated alanine-rich C kinase substrate activity may be conveniently increased by introduction of the MACMARCKS gene into the cell or by exposure of the endothelial cells to exogenous macrophage myristoylated alanine-rich C kinase substrate. Changes in expression of this gene may be used for diagnostic purposes of vascular permeability status in the embodiments of the present invention. For this purpose both nucleic acids complementary to the MACMARCKS gene as well as antibodies against the MACMARCKS protein may be applied. In addition, Wu et al. (1996, Proc Natl Acad Sci USA, 93(5): 2110-2115) generated F52-deficient mice, which may be useful to specifically investigate the blood-brain barrier in the embodiments of the present invention.

The RHO6 gene (SEQ ID NO:15; LPSS08), encoding GTP-binding protein RHO6, is upregulated in BCEC after an exposure for 2 hours to LPS in both BCEC monolayers and BCEC-astrocyte cocultures (Table 1 and Table 2). Upregulated LPSS polypeptides are involved in increased vascular permeability. GTP-binding protein RHO6 (or round1, RND1) is involved in the regulation of the actin cytoskeleton and cell adhesion. RHO6 is highly similar to ARHE (or RND3, or Rho8, or RhoE). The surprising finding that the RHO6 gene, or GTP-binding protein RHO6, was modified by LPS in the cells that constitute the blood-brain bather has not been reported earlier and offers new opportunities to modify or monitor blood-brain barrier functionality. Therefore, any agent that changes the biological activity of the RHO6 gene product (GTP-binding protein RHO6) is useful to specifically modulate the permeability of the blood-brain barrier in the embodiments of the present invention. GTP-binding protein RHO6 activity may be conveniently decreased by antisense inhibition of the RHO6 gene or by antibodies against the RHO6 protein, while GTP-binding protein RHO6 activity may be conveniently increased by introduction of the RHO6 gene into the cell or by exposure of the endothelial cells to exogenous GTP-binding protein RHO6. Changes in expression of this gene may be used for diagnostic purposes of vascular permeability status in the embodiments of the present invention. For this purpose both nucleic acids complementary to the RHO6 gene as well as antibodies against the RHO6 protein may be applied.

The PDC gene (SEQ ID NOs:16 and 17; LPSS09), encoding phosducin isoform phosducin-like protein/orphan 1, is upregulated in BCEC after an exposure for 2 hours to LPS in BCEC-astrocyte cocultures (Table 1 and Table 2). Upregulated LPSS polypeptides are involved in increased vascular permeability. Phosducin (also known as phosducin-like protein or PhLP1, or phosducin, pineal gland, or G beta gamma binding protein, or 33 kDA phototransducing protein, or PHD, or MEKA) is located in the outer and inner segments of the rod cells in the retina. Phosducin may participate in the regulation of visual phototransduction or in the integration of photoreceptor metabolism. Phosducin modulates the phototransduction cascade by interacting with the beta and gamma subunits of the retinal G-protein transducin. Two alternatively spliced transcript variants have been described. One of the isoforms encoded by the variants, the phosducin-like orphan protein, does not bind the G protein. The phosducin protein and its isoform are also present in other tissues where they may participate in signal transduction pathways. The gene encoding this protein is a potential candidate gene for retinitis pigmentosa and Usher syndrome type II. The surprising finding that the expression of the PDC gene, or phosducin isoform phosducin-like protein/orphan 1, was modified by LPS in the cells that constitute the blood-brain barrier has not been reported earlier and offers new opportunities to modify or monitor blood-brain bather functionality. Therefore, any agent that changes the biological activity of the PDC gene product (phosducin isoform phosducin-like protein/orphan 1) is useful to specifically modulate the permeability of the blood-brain barrier in the embodiments of the present invention. Phosducin isoform phosducin-like protein/orphan 1 activity may be conveniently decreased by antisense inhibition of the PDC gene or by using antibodies against the PDC protein, while phosducin isoform phosducin-like protein/orphan 1 activity may be conveniently increased by introduction of the PDC gene into the cell or by exposure of the endothelial cells to exogenous phosducin isoform phosducin-like protein/orphan 1. Changes in expression of this gene may be used for diagnostic purposes of vascular permeability status in the embodiments of the present invention. For this purpose both nucleic acids complementary to the PDC gene as well as antibodies against the PDC protein may be applied.

The CALR gene (SEQ ID NO:18; LPSS10), encoding calreticulin precursor, is differentially downregulated in BCEC after an exposure for 2 hours to LPS in BCEC-astrocyte cocultures (Table 1 and Table 2). Differentially downregulated LPSS polypeptides between BCEC monolayers and BCEC-astrocyte cocultures are involved in the ability to recover from the LPS stimulation (FIG. 2). Calreticulin (or autoantigen Ro, or Sicca syndrome antigen A or SSA, or cC1qR) is a multifunctional protein that acts as a major Ca(2+)-binding (storage) protein in the lumen of the endoplasmic reticulum. It is also found in the nucleus, suggesting that it may have a role in transcription regulation. Calreticulin binds to the synthetic peptide KLGFFKR, which is almost identical to an amino acid sequence in the DNA-binding domain of the superfamily of nuclear receptors. Calreticulin binds to antibodies in certain sera of systemic lupus and Sjögren's patients which contain anti-Ro/SSA antibodies, it is highly conserved among species, and it is located in the endoplasmic and sarcoplasmic reticulum where it may bind calcium. The amino terminus of calreticulin interacts with the DNA-binding domain of the glucocorticoid receptor and prevents the receptor from binding to its specific glucocorticoid response element. Calreticulin can inhibit the binding of androgen receptor to its hormone-responsive DNA element and can inhibit androgen receptor and retinoic acid receptor transcriptional activities in vivo, as well as retinoic acid-induced neuronal differentiation. Thus, calreticulin can act as an important modulator of the regulation of gene transcription by nuclear hormone receptors. Systemic lupus erythematosus is associated with increased autoantibody titers against calreticulin but calreticulin is not a Ro/SS-A antigen. Earlier papers referred to calreticulin as an Ro/SS-A antigen but this was later disproven. Increased autoantibody titer against human calreticulin is found in infants with complete congenital heart block of both the IgG and IgM classes. The surprising finding that the expression of the CALR gene, or calreticulin precursor, was modified by LPS in the cells that constitute the blood-brain barrier has not been reported earlier and offers new opportunities to modify or monitor blood-brain barrier functionality. Therefore, any agent that changes the biological activity of the CALR gene product (calreticulin precursor) is useful to specifically modulate the permeability of the blood-brain barrier in the embodiments of the present invention. Calreticulin precursor activity may be conveniently decreased by antisense inhibition of the CALR gene or by using antibodies against the CALR protein, while calreticulin precursor activity may be conveniently increased by introduction of the CALR gene into the cell or by exposure of the endothelial cells to exogenous calreticulin precursor. Changes in expression of this gene may be used for diagnostic purposes of vascular permeability status in the embodiments of the present invention. For this purpose both nucleic acids complementary to the CALR gene as well as antibodies against the CALR protein may be applied.

The C8FW gene (SEQ ID NO:19; LPSS11), encoding G-protein-coupled receptor induced protein, is differentially upregulated in BCEC after an exposure for 2 hours to LPS in BCEC-astrocyte cocultures (Table 1 and Table 2). Differentially upregulated LPSS polypeptides between BCEC monolayers and BCEC-astrocyte cocultures are involved in the ability to recover from the LPS stimulation (FIG. 2). C8FW (or GIG2) is the interim gene symbol and name for this phosphoprotein which is regulated by mitogenic pathways. This G-protein-coupled receptor induced protein is similar to protein kinases. The surprising finding that the expression of the C8FW gene, or the G-protein-coupled receptor induced protein, was modified by LPS in the cells that constitute the blood-brain barrier has not been reported earlier and offers new opportunities to modify or monitor blood-brain barrier functionality. Therefore, any agent that changes the biological activity of the C8FW gene product (a G-protein-coupled receptor induced protein) is useful to specifically modulate the permeability of the blood-brain barrier in the embodiments of the present invention. The G-protein-coupled receptor induced protein activity may be conveniently decreased by antisense inhibition of the C8FW gene or by using antibodies against the C8FW protein, while the G-protein-coupled receptor induced protein activity may be conveniently increased by introduction of the C8FW gene into the cell or by exogenous exposure of the endothelial cells to the G-protein-coupled receptor induced protein. Changes in expression of this gene may be used for diagnostic purposes of vascular permeability status in the embodiments of the present invention. For this purpose both nucleic acids complementary to the C8FW gene as well as antibodies against the C8FW protein may be applied.

Receptors and Adhesion Molecules

Polypeptides functioning as membrane (signaling or internalizing) receptors or (signaling) adhesion molecules are preferably used to specifically modulate the permeability of the blood-brain barrier in the embodiments of the present invention. We have identified several novel of such specifically differentially expressed polypeptides, including chemokine (C—X—C motif) receptor 4, growth hormone receptor and diphtheria toxin receptor (heparin-binding epidermal growth factor-like growth factor). These are discussed in greater detail below.

The CXCR4 gene (SEQ ID NO:20; LPSS12), encoding chemokine (C—X—C motif) receptor 4, is downregulated in BCEC after an exposure for 2 hours to LPS in BCEC-astrocyte cocultures (Table 1 and Table 2). Downregulated LPSS polypeptides are involved in increased vascular permeability. Chemokine receptor 4 is a G protein-coupled receptor that binds CXC cytokines. It mediates intracellular calcium flux. Chemokine receptor 4 is involved in activation of MAPK, apoptosis, chemotaxis, histogenesis and organogenesis, immune response, inflammatory response, invasive growth, neurogenesis, response to viruses and virulence (it is a coreceptor for HIV-1 entry in cells). Depending on what properties were being studied, this protein has been called neuropeptide Y receptor Y3 (NPY3R); fusin; leukocyte-derived 7-transmembrane-domain receptor (LESTR); seven-transmembrane-segment receptor, spleen; lipopolysaccharide (LPS)-associated protein 3 (LAPS), among various designations (like HM89, NPYR, HSY3RR, NPYY3R, D2S201E). The surprising finding that the expression of the CXCR4 gene, or chemokine receptor 4, was modified by LPS in the cells that constitute the blood-brain barrier has not been reported earlier and offers new opportunities to modify or monitor blood-brain barrier functionality. Therefore, any agent that changes the biological activity of the CXCR4 gene product (chemokine receptor 4) is useful to specifically modulate the permeability of the blood-brain bather in the embodiments of the present invention. Chemokine receptor 4 activity may be conveniently decreased by antisense inhibition of the CXCR4 gene or by chemokine receptor 4 antagonists including antibodies against the CXCR4 protein, while chemokine receptor 4 activity may be conveniently increased by introduction of the CXCR4 gene into the cell or by exposure of the endothelial cells to exogenous chemokine receptor 4 agonists. To date, the following CXCR4 antagonists have been described: peptidic compounds (T22, T134, T140, ALX40-4C, CGP64222), bicyclam derivatives (AMD3100), neutralizing antibodies (12G5, 44717-111), and natural antagonists (HIV-1 tat protein) (Sachpatzidis et al., 2003, *J Biol Chem* 278: 896-907; De Clercq et al., 2001, *Antivir Chem Chemother* 12 Suppl 1:19-31; Tamamura et al., 1998, *Biochem Biophys Res Commun* 253:877-82). To date, the following CXCR4 agonists have been described: peptidic compounds (RSVM, ASLW), and natural agonists (stromal cell-derived factor 1 α and beta (CXCL12) (Sachpatzidis et al., supra). In addition, R&D Systems Europe Ltd., UK offers recombinant human and mouse CXCL12 and useful antibodies against chemokine receptor 4 and its ligand CXCL12, which may be used for diagnostic or treatment purposes.

Changes in expression of this gene may be used for diagnostic purposes of vascular permeability status in the embodiments of the present invention. For this purpose both nucleic acids complementary to the CXCR4 gene as well as antibodies against the CXCR4 protein may be applied.

The GHR gene (SEQ ID NO:21; LPSS13), encoding growth hormone receptor, is upregulated in BCEC after an exposure for 2 hours to LPS in BCEC-astrocyte cocultures (Table 1 and Table 2). Upregulated LPSS polypeptides are involved in increased vascular permeability. Biologically active growth hormone binds its transmembrane receptor (GHR), which dimerizes to activate an intracellular signal transduction pathway leading to synthesis and secretion of insulin-like growth factor I (IGF1). In plasma, IGF1 binds to the soluble IGF1 receptor (IGF1R). At target cells, this complex activates signal-transduction pathways that result in the mitogenic and anabolic responses that lead to growth. GHR is also known as growth hormone binding protein (GHBP), which is derived from the extracellular hormone-binding region of the GHR and GHBP remains bound to growth hormone in the circulation, and serves to stabilize growth hormone in the circulation. The surprising finding that the expression of the GHR gene, or growth hormone receptor, was modified by LPS in the cells that constitute the blood-brain bather has not been reported earlier and offers new opportunities to modify or monitor blood-brain barrier functionality. Therefore, any agent that changes the biological activity of the GHR gene product (growth hormone receptor) is useful to specifically modulate the permeability of the blood-brain barrier in the embodiments of the present invention. Growth hormone receptor activity may be conveniently decreased by antisense inhibition of the GHR gene, by growth hormone receptor antagonists (including high concentrations of growth hormone, which then become antagonistic) or by antibodies against the GHR protein, while growth hormone receptor activity may be conveniently increased by introduction of the GHR gene into the cell or by exposure of the endothelial cells to exogenous growth hormone receptor agonists (like growth hormone). Changes in expression of this gene may be used for diagnostic purposes of vascular permeability status in the embodiments of the present invention. For this purpose both nucleic acids complementary to the GHR gene as well as antibodies against the GHR protein may be applied.

The DTR (or HEGFL) gene (SEQ ID NO:22; LPSS14), encoding diphtheria toxin receptor (or heparin-binding epidermal growth factor-like growth factor), is upregulated in BCEC after an exposure for 2 hours to LPS in BCEC-astrocyte cocultures (Table 1 and Table 2). Upregulated LPSS polypeptides are involved in increased vascular permeability.

Diphtheria toxin receptor (or known as HB-EGF, or heparin-binding EGF-like growth factor precursor, or diphtheria toxin sensitivity, DTS) is the receptor for diphtheria toxin (DT), a potent exotoxin produced by lysogenized strains of *Corynebacterium diphtheriae*. DT, a 58 kDa protein, is a multifunctional protein that kills susceptible mammalian cells. It is composed of two disulfide-linked protein fragments, both of which are required for the intoxication process. The A-fragment catalyzes the ADP-ribosylation of eukaryotic elongation factor 2, thereby inhibiting protein synthesis. The B-fragment is responsible for binding of the toxin to cells and is essential for facilitating the entry of the A-fragment into the cytosol. The existence of specific cell-surface DT receptors was first demonstrated in 1973, and it is now known that DT enters susceptible mammalian cells via receptor-mediated endocytosis. The initial step involves the binding of DT to the DTR, followed by internalization of the toxin:receptor complexes into coated pits and translocation of the A-fragment into the cytosol. In fact, after DT toxin binds to its cellular receptor, it is endocytosed, and while in this endocytic vesicle, it is exposed to an acidic pH environment. The acidic pH induces a structural change in the toxin molecule which provides the driving force for membrane insertion and translocation to the cytosol. Not all mammalian cells are equally sensitive to DT. For example, monkey kidney cells such as Vero cells, are highly sensitive, whereas e.g., human, rabbit, guinea pig and hamster cells are moderately sensitive and mouse and rat cells are resistant. Also chicken cells are sensitive to DT. As exemplified in example 2, DT is toxic to bovine BCEC in (sub)nanomolar range, in a concentration- and time dependent manner, after apical and basolateral exposure.

HB-EGF was originally identified in 1990 as a macrophage-secreted heparin binding growth factor. Like other members of the EGF family, HB-EGF exerts its biological effects by binding to the erb class of EGF receptor (EGF-R) molecules. HB-EGF activates two EGF receptor subtypes, HER1 and HER4 and binds to cell surface HSPG. However, unlike most members of the EGF family including EGF, HB-EGF binds heparin with a high affinity. Heparin appears to potentiate binding of HB-EGF to the signal-transducing EGF-R, and may also modulate the biologic effects of the growth factor on target cells, including cellular migration and proliferation. HB-EGF is mitogenic for fibroblasts, smooth muscle cells and epithelial cells, but not for endothelial cells. In addition, HB-EGF is produced by epithelial cells and acts as an autocrine growth factor for these cells. It is a heat-resistant, cationic protein, with a molecular weight of approximately 22 kDa that elutes from heparin-affinity chromatography columns with 1.0 M NaCl. HB-EGF gene expression is highly upregulated in response to for example oxidative, ischemic, osmotic (high glucose, or hyperosmolarity), electrical and mechanical (shear) stresses and after exposure to cytokines (TNF-α, IL-1beta, TGF-α), LPS, growth factors (EGF, HB-EGF, amphiregulin, bFGF, PDGF), lyso-Phosphatidylcholine, mercuric chloride, phorbol ester, Ca-ionophore, serum, thrombin, endothelin-1, angiotensin II, lipoprotein, platelet activation factor (PAF), α-adrenergic agonists, and transcription factors such as MyoD, Raf, v-Ha-ras. Soluble mature HB-EGF is proteolytically processed from a larger membrane-anchored precursor by matrix metalloproteinases (MMP's, in particular MMP-3) and ADAM's (a disintegrin and metalloprotease family, including ADAM9, ADAM10/Kuzbanian, ADAM12/meltrin-α, and ADAM17/TACE (TNF-α converting enzyme)). This process is called ectodomain shedding and is induced or upregulated by UV-light, IL-1beta, anisomycin, sorbitol, LPS, hydrogen peroxide, phenylephrine, endothelin-1, angiotensin II, insulin-like growth factor-1,12-O-tetradecanoylphorbol-13-acetate (TPA), via activation of protein kinase C delta and subsequent binding to the cytoplasmic domain of ADAM9/MDC9/meltrin-gamma, or by lysophosphatidic acid (LPA), via Ras-Raf-MEK and small GTPase Rac signalling pathways, or by a stress- and inflammatory cytokine-induced p38 MAPK-mediated pathway (Takenobu et al., 2003, *J. Biol. Chem.* 278: 17255-62; Umata et al., 2001, *J. Biol. Chem.* 276: 30475-82; Asakura et al., 2002, *Nature Med*, 8: 35-40). Pro-HB-EGF shedding is inhibited by MMP inhibitors like the hydroxamic acid-based KB-R8301, general MMP inhibitors (including TIMP's) and BB-94 (batimastat) and ADAM12 inhibitor KB-R7785 and the ADAM10 inhibitors XL784 and XL081, or analogues thereof. TPA-induced shedding is inhibited by the PKC inhibitor Ro-31-8220, LPA-induced shedding by the MEK antagonist PD98059, and p38 MAPK-mediated shedding by SB203580 (Takenobu et al., 2003, supra). Still, after the process of proteolytic cleavage from the membrane, a considerable amount of HB-EGF precursor remains uncleaved on the cell surface (Nakamura et al., 1995, *J. Cell Biol.* 129:1691-1705).

HB-EGF has been implicated as a participant in a variety of normal physiological processes such as blastocyst implantation and wound healing, and in pathological processes such as tumor growth, SMC hyperplasia and atherosclerosis. HB-EGF gene expression has been demonstrated in a variety of tissues, including vascular endothelial and smooth muscle cells, inflammatory cells (mostly NK-cells), skeletal and heart muscle, kidney mesangial cells, keratinocytes, small intestine, brain (neurons and glial cells), whole joints, trophoblasts, blastocysts, ovary and uterus, placenta, skin, lymph node, bladder and tumor cells (including glioma).

HB-EGF precursor has recently been found to function as the receptor for diphtheria toxin (Naglich et al., 1992, *Cell* 69: 1051-61). Although HB-EGF precursor is expressed in species including human, monkey, rat and mouse with a similar tissue distribution, rat and mice are resistant to DT because of an amino acid substitution in the sequence that is specifically recognized by DT (the receptor-binding domain for DT on HB-EGF) in humans and monkeys, that reduces binding of DT to rodent HB-EGF (Mitamura et al., 1995, *J. Biol. Chem.* 270:1015-19). Recently, AA141 ($Glu_{141}$) has been shown to be a critical residue for DT-binding and toxin sensitivity (Hooper and Eidels, 1996, *Biochem. Biophys. Res. Commun.* 220: 675-680). Later, Mitamura et al., 1997, *J. Biol. Chem.* 272: 27084-90, discovered two additional critical residues for DT-binding and toxin sensitivity (AA115 ($Phe_{115}$) and AA127 ($Leu_{127}$)). Table 3 shows the sequence of the DT-receptor binding domain (AA106-147) of HB-EGF across different DT-insensitive (mouse, rat) and DT-sensitive (chinese hamster, rabbit, pig, monkey, human and chicken) species.

TABLE 3

Sequence of the DT-receptor binding domain (AA106-147) of HB-EGF in DT-insensitive species (mouse (Ms), rat (Rt)) and DT-sensitive species (chinese hamster (CH), rabbit (Rb), pig (P), monkey (Mk), human (H) and chicken (C))

| | | |
|---|---|---|
| Ms | DPCLR | KYK*DY*CIHGECRY*LQE*RTPSC*K*CLPGYHG*H*RCHGLT |
| Rt | DPCLK | KYK*DY*CIHGECRY*LKELRIPS*C*H*CLPGYHC*Q*RCHGLT |
| CH | DPCLR | KYKDFCIHGECKY*LKDLRAPSC*N*CHPGYHGERCHGLT |
| Rb | DPCLR | KYKDFCIHGECKY*LKELRAPSCI*CHPGYHGERCHGLS |
| P | DPCLR | KYKDFCIHGECKY*V*KELRAPSCI*CHPGYHGERCHGLS |
| Mk | DPCLR | KYKDFCIHGECKY*V*KELRAPSCI*CHPGYHGERCHGLS |
| H | DPCLR | KYKDFCIHGECKY*V*KELRAPSCI*CHPGYHGERCHGLS |
| C | DPCLR | KYKDFCIHGECKY*IRELGAPSCIC*Q*PGYHGERCHGLL |

Residues that differ from human are depicted in italic, and the residues depicted in bold are critical residues for DT-binding and toxin sensitivity (AA115 ($Phe_{115}$), AA127 ($Leu_{127}$) and AA141 ($Glu_{141}$))

Heparin, heparan sulfate and heparan sulfate proteoglycans (HSPG), and other associate proteins like CD9/DRAP27 and α3-beta1-integrin, modulate DTR function by increasing DTR affinity for its ligands (as well as for HB-EGF binding to its receptor (Shishido et al., 1995, *J. Biol. Chem.* 270:29578-85)). Anti-CD9/DRAP27 monoclonal antibodies (IgG1: ALB-6 and TP82, and IgG2a: BU16 and 007, and MAB1206), inhibit the binding and toxicity of DT to human cells (Nakamura et al., 1995, supra; Mitamura et al., 1992, *J. Cell Biol.* 118: 1389-99; Iwamoto et al., 1991, *J. Biol. Chem.* 266: 20463-9).

The finding that the DTR gene (or diphtheria toxin receptor (or heparin-binding epidermal growth factor-like growth factor), was expressed on the cells that constitute the blood-brain barrier (as exemplified in examples 1 and 2) and that the biological activity of DTR was modified by disease stimuli (as exemplified for LPS in examples 1 and 3), heparin binding (as exemplified for exposure to exogenous heparin in example 3), antagonists (as exemplified for CRM197 (a competitive antagonist of DT) in example 2 and soluble HB-EGF (a non-competitive antagonist of DT) in examples 2 and 4), inhibitors of ectodomain shedding (as exemplified by exposure to the matrix metalloproteinase BB-94 (or batimastat) in example 3), or combinations thereof (as exemplified in example 3), offers new opportunities to specifically target drugs to and across the blood-brain barrier and/or to an intracellular compartment, particularly the lysosome. Any agent that changes the biological activity of the DTR gene product (i.e., heparin-binding epidermal growth factor-like growth factor) is useful to specifically modulate the targeting capacity to the blood-brain barrier in the embodiments of the present invention. Any ligand that specifically binds to (the receptor-binding domain of) DTR (like (parts of) DT, (parts of) the B-fragment of DT, (parts of) CRM197 (as exemplified in example 4), or any other ligand) is useful to target drugs to the blood-brain barrier in the embodiments of the present invention.

The general concept of the use of protein toxins (or non-toxic derivatives thereof) as carriers for e.g., peptides and proteins, across membranes and into the cytosol is not new (see for references on this subject the recent review of Sandvig et al. (2002, *Annu. Rev. Cell Dev. Biol.* 18: 1-24). DT, after binding to its receptor HB-EGF, is internalized by a process called receptor-mediated endocytosis. Receptor-mediated endo-/transcytosis is a well-known safe and effective cargo-carrying transport mechanism for the selective targeting of drugs to the brain (Pardridge, 2002, *Nat. Rev. Drug Discov.,* 1:131-9). However, the use of specific ligands for DTR to carry drugs directly across the blood-brain barrier into the CNS by a mechanism involving receptor-mediated endo-/transcytosis, as has been described for e.g., the transferrin receptor, has never been appreciated earlier. In fact, only the non-toxic C fragment of the tetanus toxin protein (TTC or Tet451), and the non-toxic derivative of the tetanus toxin protein (Glu234 substitution by Ala), have been exploited to carry drugs into the CNS, however by a clearly distinctive mechanism of action (as compared to receptor-mediated endo-/transcytosis at the blood-brain bather), involving uptake into peripheral nerve endings followed by retrograde axonal transport to their cell body and trans-synaptic transfer to central neurons (described in U.S. Pat. No. 5,780,024 and in the references cited therein, and Li et al., 2001, *J. Biol. Chem.* 276: 31394-401). Even though constitutive and disease-induced HB-EGF expression in neurons, glial cells and blood vessels in the brain of rats was already described earlier by Mishima et al., 1996, *Neurosci. Lett.* 213: 153-6; Nakagawa et al., 1998, *Dev. Brain Res.* 108: 263-72; Hayase et al., 1998, *Brain Res.* 784:163-78; and Tanaka et al., 1999, *Brain Res.* 827:130-8. None of these authors appreciated the opportunity for the targeted delivery of drugs coupled to ligands of the DTR to (intracellular compartments in) these cells in the brain. This omission is best explained by the fact that rodent HB-EGF is not a receptor for DT. In fact, in rodents the permeability of DT across the microvasculature of brain tumors is equal to or less than the permeability of other large proteins (Wrobel et al., 1990, *J. Neurosurg.* 72:946-50), even though it could effectively kill tumor cells within the brain after passive diffusion (Arguello et al., 1996. Blood 87:4325-32). Therefore these studies only reported on the auto- and juxtacrine growth- and adhesion factor properties of HB-EGF. Even more surprisingly, neither renowned CNS drug delivery experts on receptor-mediated endo-/transcytosis (including Pardridge and Rapoport who published numerous scientific and review papers/books, patents and patent applications on the subject), nor the authors of the most recently published U.S. patent application "Covalent conjugates of biologically-active compounds with amino acids and amino acid derivatives for targeting to physiologically-protected sites," Yatvin et al. (US2003-0087803), in which a comprehensive overview of the available technologies for drug delivery to the brain is given and which is included herein as reference, have appreciated the opportunity for the targeted delivery of drugs coupled to ligands of the DTR to (intracellular compartments in) cells in the brain.

The fact that DT is very toxic to susceptible mammalian cells makes drug targeting to the DTR with its natural ligand DT not preferable. However, the identification of non-toxic parts of DT, including (parts of) the B-fragment of DT, or (parts of) CRM197 (a non-toxic mutant protein of DT), have opened the door to the safe and effective targeting of drugs to the brain via the DTR. CRM197 is most preferred because polysaccharides conjugated to CRM197 have already been safely applied for human use to millions of people (babies, toddlers, adolescents and adults) in vaccination programs (e.g., *Haemophilus influenzae* type b oligosaccharide CRM197 conjugate vaccine (HibTiter™); Pneumococcal 7-valent Conjugate Vaccine (Prevnar™); meningococcal C oligosaccharide conjugate vaccines (Menjugate™ and Meningtec™)). From these indications it is known that the CRM197 protein is a safe and effective T-cell dependent carrier for saccharides. Likewise, CRM66 (cross-reactive 66 kDa protein) is an inactive mutant form of *Pseudomonas aeruginosa* exotoxin A, which specifically binds to the low density lipoprotein (LDL) receptor-related protein (LRP) and LRP 1B, and may be exploited to deliver drugs across the blood-brain barrier in a similar fashion as has been described for p97 (melanotransferrin) by Demeule et al. (2002, *J. Neurochem.* 83:924-33), which binds to the same receptor (WO03/009815).

CRM197 is produced by *Corynebacterium diphtheriae* infected by the nontoxigenic phage (beta197$^{tox-}$) created by nitrosoguanidine mutagenesis of the toxigenic corynephage (β) (Uchida, et al. 1971, *Nature New Biol.* 233:8-11). The CRM197 protein has the same molecular weight as the diphtheria toxin but differs therefrom by a single base change (guanine to adenine) in the structural gene. This single base change causes an amino acid substitution (AA52: glutamic acid for glycine) in the mature protein and eliminates the toxic properties of diphtheria toxin.

Carrier proteins in vaccines were discovered based on the following concept. Vaccination with full (but inactivated) viruses or bacteria is effective but has many disadvantages and side-effects. For this reason, vaccination protocols with only the immunogenic parts (or mimics) of the viruses and bacteria (e.g., (poly)saccharides or capsular proteins) have been developed. However, such vaccines are least effective in the segment of the population most at risk for infections: B cell immunocompromised individuals, the elderly and infants younger than two years old who depend on T cell responses for immune protection. Since such vaccines are poor inducers of T-cell responses, conversion of the immunogenic parts of the viruses and bacteria into immunogens capable of inducing T cell responses is the key to producing adequate protection in this target population. It was discovered that linking the immunogenic parts of the viruses and bacteria to a suitable protein carrier, such as keyhole limpet hemocyanin (KLH), tetanus toxoid (TT), diphtheria toxoid (formalinized DT), bovine serum albumin (BSA), or human serum albumin (HSA), produced such an immunogen, by an nonspecific mechanism of action. In fact, the mechanism of action for diphtheria toxoid-conjugates was herein not linked to the effects mediated by binding to DTR on lymphocytes. To circumvent any remaining toxicity of diphtheria toxoid-conjugates, the diphtheria toxoid was later replaced by the non-toxic mutant of DT, CRM197. The notion that the carrier proteins are used on the basis of a nonspecific mechanism of action is further endorsed by the fact that the efficacy of CRM197-conjugate vaccines is routinely tested in DT-insensitive mice. Gupta et al. (1997, *Vaccine* 15:1341-3) showed that large differences in immunogenicity of CRM197-conjugated vaccines can be demonstrated between DT-insensitive mice and DT-sensitive guinea pigs, indicating that CRM197-conjugated vaccines do indeed make use of specific DTR-mediated cellular uptake in DT-sensitive species.

Neutralizing antibodies against (receptor-binding domain of) DT may be present in serum of the recipient because of earlier exposure to, or vaccination against *Corynebacterium diphtheriae*, (part of) DT (B-fragment) or (part of) CRM197 (or any other (part of) non-toxic DT) which may prevent the specific binding of drugs conjugated to CRM197 (or any other compound that binds specifically to the DT-binding domain) on the DTR, thereby reducing the overall efficacy of the drug delivery system. Such neutralizing antibodies are preferably inactivated prior to the application of the drug delivery system by exposure of the recipient to an effective, minimal amount of free CRM197, or any other compound that binds specifically to the DT-binding domain on the neutralizing antibody (like (part of) DT (B-fragment) or (part of) CRM197 fragments of CRM197, small molecules, peptides, mimetics, anti-idiotypic antibodies, etc.).

In addition, the surprising finding that the expression of the DTR gene, or diphtheria toxin receptor (or heparin-binding epidermal growth factor-like growth factor), was modified by LPS in the cells that constitute the blood-brain bather offers new opportunities to modify or monitor blood-brain barrier functionality. In addition, any agent that changes the biological activity of the DTR gene product (i.e., heparin-binding epidermal growth factor-like growth factor) is useful to specifically modulate the permeability of the blood-brain barrier in the embodiments of the present invention. Diphtheria toxin receptor (heparin-binding epidermal growth factor-like growth factor) activity may be conveniently decreased by antisense inhibition of the DTR gene or by heparin-binding epidermal growth factor-like growth factor antagonists or by antibodies against the DTR protein, while diphtheria toxin receptor (heparin-binding epidermal growth factor-like growth factor) activity may be conveniently increased by introduction of the DTR gene into the cell or by exposure of the endothelial cells to exogenous heparin-binding epidermal growth factor-like growth factor. In addition, R&D Systems Europe Ltd., UK offers recombinant human HB-EGF and useful antibodies against HB-EGF, which may be used for diagnostic or treatment purposes. Changes in expression of this gene may be used for diagnostic purposes of vascular permeability status in the embodiments of the present invention. For this purpose both nucleic acids complementary to the HB-EGF gene as well as antibodies against the HB-EGF protein may be applied.

To greatly enhance the ease of experimentation and availability of relevant animal disease models in order to specifically study the permeability of the blood-brain barrier in the embodiments of the present invention, it is highly preferred that a human-like HB-EGF transgenic or knock-in (KI) mice is generated. Human-like HB-EGF transgenic mice can be genetically engineered by introducing the human DTR gene (encoding HB-EGF) under the control of a constitutively activated (e.g., tumor) promoter or a tissue specific promoter, preferably the GFAP and/or gamma-GTP promoters to obtain brain and/or cerebrovascular expression of the gene. Most preferred, however, is the introduction by homologous recombination in ES cells of a genetically engineered Hegfl gene (encoding the mouse HB-EGF gene under its endogenous promoter(s)) such that the exons 2 and 3 will contain the human sequences for the receptor-binding domain for diphtheria toxin, preferably containing positive and negative selection marker sequences. The coding sequences for the receptor-binding domain for diphtheria toxin are located at the end of exon 2 and the beginning of exon 3. To this end, mouse genomic DNA clones are derived from PAC libraries, preferably the pPAC4 library (129/SvevTACfBr strain). In the targeting vector the original second and third exon are replaced by the human specific sequences for the receptor-binding domain for diphtheria toxin by genetic engineering, creating a diphtheria toxin sensitive receptor-binding domain. Within intron 2 or downstream of exon 3, a PGK-driven neo cassette flanked by LoxP sites are present. Embryonic stem cells (E14) are electroporated and clones selected for homologous recombination by Southern blot analysis using external probes. The presence of the human sequences for the receptor-binding domain for diphtheria toxin are tested by PCR using human specific primers, preferably in addition to subsequent digestion with restriction enzyme, as well as by sequencing analysis of exons 2 and 3. Targeted ES cells are injected into blastocysts to create chimeric animals. $F_1$ agouti progeny are genotyped for transmission of the mutant allele, generating transgenic line human-like HB-EGF+Neo. Heterozygous human-like HB-EGF+Neo mice are bred with mice of the EIIA-Cre strain (Lakso et al., 1996, *Proc. Natl. Acad. Sci. USA.* 93:5860-65) to remove the neo cassette. By these means, germline transmission is obtained and transgenic line human-like HB-EGF KI is established. Mice are further bred with C57BL/6J for five generations. Homozygous human-like HB-EGF KI and wt littermates are used for further analysis (~97% C57BL/6J background). Then, in order to grow a xenogeneic tumor implant in the human-like HB-EGF KI mice, a number of immunodeficient mice are available for use in the invention. These mice, include but are not limited to, nude mice, scid mice and mice deficient in the rag-1 and rag-2 genes. Other animals with diverse types of immunodeficiency as a result of mutations of certain genetic loci can be found in the website immunology.tch.harvard.edu. These mice are crossed with the aforementioned human-like HB-EGF KI mice to produce progenies that are deficient in immune function, but do express the human-like HB-EGF. In addition, no immunogenic response (leading to e.g., neutralizing antibodies) against exogenous carrier proteins, like CRM197, is expected in these mice. Further, the aforementioned human-like HB-EGF KI (original and/or immunodeficient) mice is crossed with any of the knockout of transgenic/KI mice described in the art serving as disease models to produce progenies that both have the disease phenotype and are sensitive to exogenous carrier proteins, like CRM197. Likewise, transgenic rats and pigs can also be generated accordingly.

Sequence Identity

"Sequence identity" is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods, including but not limited to those described in (*Computational Molecular Biology*, Lesk, A M, ed., Oxford University Press, New York, 1988; *Biocomputing: Informatics and Genome Projects*, Smith, D W, ed., Academic Press, New York, 1993; *Computer Analysis of Sequence Data, Part I*, Griffin, A M et al., eds., Humana Press, New Jersey, 1994; *Sequence Analysis in Molecular Biology*, von Heine, G., Academic Press, 1987; *Sequence Analysis Primer*, Gribskov, M et al., eds., M Stockton Press, New York, 1991; and Carillo, H., and Lipman, D., *SIAM J. Applied Math.* 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g., the GCG program package (Devereux, J., et al., *Nucl Acids Res* 12:387 (1984)), BestFit, BLASTP, BLASTN, and FASTA (Altschul, S F et al., *J. Mol. Biol.* 215:403-10 (1990). The BLAST X program is publicly available from NCBI and other sources (BLAST Manual, Altschul, S F, et al., NCBI NLM NIH Bethesda, Md. 20894; Altschul, et al., 1990, supra). The well-known Smith Waterman algorithm may also be used to determine identity.

Preferred parameters for polypeptide sequence comparison include the following: Algorithm: Needleman and Wunsch, *J. Mol. Biol.* 48:443-53 (1970); Comparison matrix: BLOSSUM62 from Hentikoff and Hentikoff, *Proc. Natl. Acad. Sci. USA.* 89:10915-19 (1992); Gap Penalty: 12; and Gap Length Penalty: 4. A program useful with these parameters is publicly available as the "Ogap" program from Genetics Computer Group, in Madison, Wis. The aforementioned parameters are the default parameters for amino acid comparisons (along with no penalty for end gaps).

Preferred parameters for nucleic acid comparison include the following: Algorithm: Needleman and Wunsch, supra); Comparison matrix: matches=+10, mismatch=0; Gap Penalty: 50; Gap Length Penalty: 3. Available as the Gap program from Genetics Computer Group. Given above are the default parameters for nucleic acid comparisons.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; H is to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Methods for Recombinant Production of Polypeptides

Polypeptides for use in the present invention can be prepared using recombinant techniques, in which a nucleotide sequence encoding the polypeptide of interest is expressed in suitable host cells. The present invention thus also concerns the use of a vector comprising a nucleic acid molecule or nucleotide sequence as defined above. Preferably the vector is a replicative vector comprising on origin of replication (or autonomously replication sequence) that ensures multiplication of the vector in a suitable host for the vector. Alternatively the vector is capable of integrating into the host cell's genome, e.g., through homologous recombination or otherwise. A particularly preferred vector is an expression vector wherein a nucleotide sequence encoding a polypeptide as defined above, is operably linked to a promoter capable of directing expression of the coding sequence in a host cell for the vector.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A "tissue specific" promoter is only active in specific types of differentiated cells/tissues.

Expression vectors allow the LPSS polypeptides as defined above to be prepared using recombinant techniques in which a nucleotide sequence encoding the LPSS polypeptide of interest is expressed in suitable cells, e.g., cultured cells or cells of a multicellular organism, such as described in Ausubel et al., "Current Protocols in Molecular Biology", Greene Publishing and Wiley-Interscience, New York (1987) and in Sambrook and Russell (2001, supra); both of which are incorporated herein by reference in their entirety. Also see, Kunkel, 1985, *Proc. Natl. Acad. Sci. USA* 82:488 (describing site directed mutagenesis) and Roberts et al., 1987, *Nature* 328:731-4 or Wells, JA et al., 1985, *Gene* 34:315 (describing cassette mutagenesis).

Typically, nucleic acids encoding the desired polypeptides are used in expression vectors. The phrase "expression vector" generally refers to nucleotide sequences that are capable of effecting expression of a gene in hosts compatible with such sequences. These expression vectors typically include at least suitable promoter sequences and optionally, transcription termination signals. Additional factors necessary or helpful in effecting expression can also be used as described herein. DNA encoding a polypeptide is incorporated into DNA constructs capable of introduction into and expression in an in vitro cell culture. Specifically, DNA constructs are suitable for replication in a prokaryotic host, such as bacteria, e.g., *E. coli*, or can be introduced into a cultured mammalian, plant, insect, e.g., Sf9, yeast, fungi or other eukaryotic cell lines.

DNA constructs prepared for introduction into a particular host typically include a replication system recognized by the host, the intended DNA segment encoding the desired polypeptide, and transcriptional and translational initiation and termination regulatory sequences operably linked to the polypeptide-encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters or linkers inserted in lieu thereof.

The selection of an appropriate promoter sequence generally depends upon the host cell selected for the expression of the DNA segment. Examples of suitable promoter sequences include prokaryotic, and eukaryotic promoters well known in the art (see, e.g., Sambrook and Russell, 2001, supra). The transcriptional regulatory sequences typically include a heterologous enhancer or promoter that is recognized by the host. The selection of an appropriate promoter depends upon the host, but promoters such as the trp, lac and phage promoters, tRNA promoters and glycolytic enzyme promoters are known and available (see, e.g., Sambrook and Russell, 2001, supra). Expression vectors include the replication system and transcriptional and translational regulatory sequences together with the insertion site for the polypeptide encoding segment can be employed. Examples of workable combinations of cell lines and expression vectors are described in Sambrook and Russell (supra) and in Metzger et al. (1988) *Nature* 334: 31-6. For example, suitable expression vectors can be expressed in, yeast, e.g., *S. cerevisiae*, e.g., insect cells, e.g., Sf9 cells, mammalian cells, e.g., CHO cells and bacterial cells, e.g., *E. coli*. The host cells may thus be prokaryotic or eukaryotic host cells. The host cell may be a host cell that is suitable for culture in liquid or on solid media. The host cells are used in a method for producing a LPSS polypeptide as defined above. The method comprises the step of culturing a host cell under conditions conducive to the expression of the polypeptide. Optionally the method may comprise recovery the polypeptide. The polypeptide may e.g., be recovered from the culture medium by standard protein purification techniques, including a variety of chromatography methods known in the art per se.

Alternatively, the host cell is a cell that is part of a multicellular organism such as a transgenic plant or animal, preferably a non-human animal. A transgenic plant comprises in at least a part of its cells a vector as defined above. Methods for generating transgenic plants are e.g., described in U.S. Pat. No. 6,359,196 and in the references cited therein. Such transgenic plants may be used in a method for producing a LPSS polypeptide as defined above, the method comprising the step of recovering a part of a transgenic plant comprising in its cells the vector or a part of a descendant of such transgenic plant, whereby the plant part contains the polypeptide, and, optionally recovery of the polypeptide from the plant part. Such methods are also described in U.S. Pat. No. 6,359, 196 and in the references cited therein. Similarly, the transgenic animal comprises in its somatic and germ cells a vector as defined above. The transgenic animal preferably is a non-human animal. Methods for generating transgenic animals are e.g., described in WO 01/57079 and in the references cited therein. Such transgenic animals may be used in a method for producing a LPSS polypeptide as defined above, the method comprising the step of recovering a body fluid from a transgenic animal comprising the vector or a female descendant thereof, wherein the body fluid contains the polypeptide, and, optionally recovery of the polypeptide from the body fluid. Such methods are also described in WO 01/57079 and in the references cited therein. The body fluid containing the polypeptide preferably is blood or more preferably milk.

Another method for preparing polypeptides is to employ an in vitro transcription/translation system. DNA encoding a polypeptide is cloned into an expression vector as described supra. The expression vector is then transcribed and translated in vitro. The translation product can be used directly or first purified. Polypeptides resulting from in vitro translation typically do not contain the post-translation modifications present on polypeptides synthesized in vivo, although due to the inherent presence of microsomes some post-translational modification may occur. Methods for synthesis of polypeptides by in vitro translation are described by, for example, Berger & Kimmel, *Meth Enzymol.* 152, *Guide to Molecular Cloning Techniques*, Academic Press, San Diego, Calif., 1987.

Gene Therapy

Some aspects of the invention concern the use of expression vectors comprising the nucleotide sequences as defined above, wherein the vector is a vector that is suitable for gene therapy. Vectors that are suitable for gene therapy are described in Anderson 1998, *Nature* 392: 25-30; Walther and Stein, 2000, *Drugs* 60: 249-71; Kay et al., 2001, *Nat. Med.* 7: 33-40; Russell, 2000, *J. Gen. Virol.* 81: 2573-2604; Amado and Chen, 1999, *Science* 285: 674-6; Federico, 1999, *Curr. Opin. Biotechnol.* 10: 448-53; Vigna and Naldini, 2000, *J. Gene Med.* 2: 308-16; Marin et al., 1997, *Mol. Med. Today* 3: 396-403; Peng and Russell, 1999, *Curr. Opin. Biotechnol.* 10: 454-7; Sommerfelt, 1999, *J. Gen. Virol.* 80: 3049-64; Reiser, 2000, *Gene Ther.* 7: 910-3; and references cited therein.

Particularly suitable gene therapy vectors include Adenoviral and Adeno-associated virus (AAV) vectors. These vectors infect a wide number of dividing and non-dividing cell types. In addition adenoviral vectors are capable of high levels of transgene expression. However, because of the episomal nature of the adenoviral and AAV vectors after cell entry, these viral vectors are most suited for therapeutic applications requiring only transient expression of the transgene (Russell, 2000, supra) as indicated above. Preferred adenoviral vectors are modified to reduce the host response as reviewed by Russell (supra).

Generally, gene therapy vectors will be as the expression vectors described above in the sense that they comprise the nucleotide sequence encoding the LPSS polypeptide to be expressed, whereby the nucleotide sequence is operably linked to the appropriate regulatory sequences as indicated above. Such regulatory sequence will at least comprise a promoter sequence. Suitable promoters for expression of the nucleotide sequence encoding the polypeptide from gene therapy vectors include e.g., cytomegalovirus (CMV) intermediate early promoter, viral long terminal repeat promoters (LTRs), such as those from murine moloney leukemia virus (MMLV) Rous sarcoma virus, or HTLV-1, the simian virus 40 (SV40) early promoter and the herpes simplex virus thymidine kinase promoter.

Several inducible promoter systems have been described that may be induced by the administration of small organic or inorganic compounds. Such inducible promoters include those controlled by heavy metals, such as the metallothionine promoter (Brinster et al. 1982 *Nature* 296: 39-42; Mayo et al. 1982 *Cell* 29: 99-108), RU-486 (a progesterone antagonist) (Wang et al. 1994 *Proc. Natl. Acad. Sci. USA* 91: 8180-4), steroids (Mader and White, 1993 *Proc. Natl. Acad. Sci. USA* 90: 5603-7), tetracycline (Gossen and Bujard 1992 *Proc. Natl. Acad. Sci. USA* 89: 5547-51; U.S. Pat. No. 5,464,758; Furth et al. 1994 *Proc. Natl. Acad. Sci. USA* 91: 9302-6; Howe et al. 1995 *J. Biol. Chem.* 270: 14168-74; Resnitzky et al. 1994 *Mol. Cell. Biol.* 14: 1669-79; Shockett et al. 1995 *Proc. Natl. Acad. Sci. USA* 92: 6522-6) and the tTAER system that is based on the multi-chimeric transactivator composed of a tetR polypeptide, as activation domain of VP16, and a ligand binding domain of an estrogen receptor (Yee et al., 2002, U.S. Pat. No. 6,432,705).

The gene therapy vector may optionally comprise a second or one or more further nucleotide sequence coding for a second or further protein. The second or further protein may be a (selectable) marker protein that allows for the identification, selection and/or screening for cells containing the expression construct. Suitable marker proteins for this purpose are e.g., the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) *Molecular Cloning: A Laboratory Manual* ($3^{rd}$ edition), Cold Spring Harbor Laboratory Press, New York.

Alternatively, the second or further nucleotide sequence may encode a protein that provides for fail-safe mechanism that allows to cure a subject from the transgenic cells, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g., the *E. coli* cytosine deaminase gene or one of the thymidine kinase genes from Herpes Simplex Virus, Cytomegalovirus and Varicella-Zoster virus, in which case ganciclovir may be used as prodrug to kill the IL-10 transgenic cells in the subject (see e.g., Clair et al., 1987, *Antimicrob. Agents Chemother.* 31: 844-9).

The gene therapy vectors are preferably formulated in a pharmaceutical composition comprising a suitable pharmaceutical carrier as defined below.

Antibodies

Some aspects of the invention concern the use of an antibody or antibody-fragment that specifically binds to a LPSS polypeptide of the invention as defined above. Methods for generating antibodies or antibody-fragments that specifically bind to a given polypeptide are described in e.g., Harlow and Lane (1988, Antibodies: A Laboratory Manual, Cold Spring Harbor Laboratory Press, Cold Spring Harbor, N.Y.) and WO 91/19818; WO 91/18989; WO 92/01047; WO 92/06204; WO 92/18619; and U.S. Pat. No. 6,420,113 and references cited therein. The term "specific binding," as used herein, includes both low and high affinity specific binding. Specific binding can be exhibited, e.g., by a low affinity antibody or antibody-fragment having a Kd of at least about $10^{-4}$ M. Specific binding also can be exhibited by a high affinity antibody or antibody-fragment, for example, an antibody or antibody-fragment having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater.

Peptidomimetics

Peptide-like molecules (referred to as peptidomimetics) or non-peptide molecules that specifically bind to a LPSS polypeptide or a LPSS polypeptide receptor and that may be applied in any of the methods of the invention as defined herein may be identified using methods known in the art per se, as e.g., described in detail in U.S. Pat. No. 6,180,084 which incorporated herein by reference. Such methods include e.g., screening libraries of peptidomimetics, peptides, DNA or cDNA expression libraries, combinatorial chemistry and, particularly useful, phage display libraries. These libraries may be screened for agonists and antagonists of LPSS polypeptides or receptors thereof by contacting the libraries with substantially purified LPSS polypeptides, LPSS polypeptide receptors, fragments thereof or structural analogues thereof.

Pharmaceutical Compositions

The invention further relates to a pharmaceutical preparation comprising as active ingredient a LPSS polypeptide, an antibody or a gene therapy vector as defined above. The composition preferably at least comprises a pharmaceutically acceptable carrier in addition to the active ingredient.

In some methods, the polypeptide or antibody of the invention as purified from mammalian, insect or microbial cell cultures, from milk of transgenic mammals or other source is administered in purified form together with a pharmaceutical carrier as a pharmaceutical composition. Methods of producing pharmaceutical compositions comprising polypeptides are described in U.S. Pat. Nos. 5,789,543 and 6,207,718. The preferred form depends on the intended mode of administration and therapeutic application.

The pharmaceutical carrier can be any compatible, non-toxic substance suitable to deliver the polypeptides, antibodies or gene therapy vectors to the patient. Sterile water, alcohol, fats, waxes, and inert solids may be used as the carrier. Pharmaceutically acceptable adjuvants, buffering agents, dispersing agents, and the like, may also be incorporated into the pharmaceutical compositions.

The concentration of the LPSS polypeptides or antibodies of the invention in the pharmaceutical composition can vary widely, i.e., from less than about 0.1% by weight, usually being at least about 1% by weight to as much as 20% by weight or more.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The LPSS polypeptides, antibodies or gene therapy vectors are preferably administered parentally. The polypeptide, antibody or vector for preparations for parental administration must be sterile. Sterilization is readily accomplished by filtration through sterile filtration membranes, prior to or following lyophilization and reconstitution. The parental route for administration of the LPSS polypeptide, antibody or vector is in accord with known methods, e.g., injection or infusion by intravenous, intraperitoneal, intramuscular, intraarterial, intralesional, intracranial, intrathecal, transdermal, nasal, buccal, rectal, or vaginal routes. The polypeptide, antibody or vector is administered continuously by infusion or by bolus injection. A typical composition for intravenous infusion could be made up to contain 10 to 50 ml of sterile 0.9% NaCl or 5% glucose optionally supplemented with a 20% albumin solution and 1 to 50 μg of the LPSS polypeptide, antibody or vector. A typical pharmaceutical composition for intramuscular injection would be made up to contain, for example, 1-10 ml of sterile buffered water and 1 to 100 μg of the LPSS polypeptide, antibody or vector of the invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

For therapeutic applications, the pharmaceutical compositions are administered to a patient suffering from a microvascular permeability disorder in an amount sufficient to reduce the severity of symptoms and/or prevent or arrest further development of symptoms. An amount adequate to accomplish this is defined as a "therapeutically-" or "prophylactically-effective dose". Such effective dosages will depend on the severity of the condition and on the general state of the patient's health. In general, a therapeutically- or prophylactically-effective dose preferably is a dose, which restores the microvascular permeability to the average levels found in normal unaffected healthy individuals.

In the present methods, the LPSS polypeptide or antibody is usually administered at a dosage of about 1 μg/kg patient body weight or more per week to a patient. Often dosages are greater than 10 μg/kg per week. Dosage regimes can range from 10 μg/kg per week to at least 1 mg/kg per week. Typically dosage regimes are 10 μg/kg per week, 20 μg/kg per week, 30 μg/kg per week, 40 μg/kg week, 60 μg/kg week, 80 μg/kg per week and 120 μg/kg per week. In preferred regimes 10 μg/kg, 20 μg/kg or 40 μg/kg is administered once, twice or three times weekly. Treatment is preferably administered by parenteral route.

Microarrays

Another aspect of the invention relates to microarrays (or other high throughput screening devices) comprising the nucleic acids, polypeptides or antibodies as defined above. A microarray is a solid support or carrier containing one or more immobilized nucleic acid or polypeptide fragments for analyzing nucleic acid or amino acid sequences or mixtures thereof (see e.g., WO 97/27317, WO 97/22720, WO 97/43450, EP 0 799 897, EP 0 785 280, WO 97/31256, WO 97/27317, WO 98/08083 and Zhu and Snyder, 2001, Curr.

Opin. Chem. Biol. 5: 40-45). Microarrays comprising the nucleic acids may be applied e.g., in methods for analyzing genotypes or expression patterns as indicated above. Microarrays comprising polypeptides may be used for detection of suitable candidates of substrates, ligands or other molecules interacting with the polypeptides. Microarrays comprising antibodies may be used for in methods for analyzing expression patterns of the polypeptides as indicated above.

EXAMPLES

Methods and Materials for Examples 1.1 Cell Culture 1.1.1 Isolation of Bovine Brain Capillaries Brain capillaries were isolated from bovine (calf) brain, obtained at the slaughterhouse from freshly killed animals. The brain was transported to the laboratory in ice-cold phosphate buffered saline (LPSS, 1.1 mM $KH_2PO_4$, 5.6 mM $Na_2HPO_4$ and 150 mM NaCl, pH 7.4). Meninges and white matter were removed and gray matter was collected in Dulbecco's Modified Eagle's Medium (DMEM), supplemented with 10% (v/v) heat inactivated (30 min at 56° C.) fetal calf serum (DMEM+S). The DMEM, formulated with high D-glucose (4.5 g/l), $NaHCO_3$ (3.7 g/l) and HEPES (25 mM), contained extra MEM non-essential amino acids, L-glutamine (2 mM), streptomycin sulfate (0.1 g/l) and penicillin G sodium (100000 U/l). Blood vessel fragments were prepared by manual homogenization using a Wheaton homogenizer and subsequently trapped on 150 µm nylon meshes. The blood vessels were digested in collagenase CLS3 (210 U/ml), trypsin TRL (91 U/ml) and DNAse I (170 U/ml, final concentrations) in DMEM+S for 1 hour at 37° C. and subsequently filtered through a 200 µm nylon mesh. The brain capillary fraction was resuspended in freeze mix (fetal calf serum (FCS) with 10% (v/v) DMSO) and stored at −80° C.

1.1.2 Isolation of Astrocytes

Astrocytes were isolated from newborn Wistar rat pups (Harlan B. V., Zeist, The Netherlands). Isolated cortices were fragmented and incubated with 0.016% (w/v) trypsin-EDTA (final concentration) in DMEM (fully HEPES buffered (50 mM), without $NaHCO_3$) in a shaking water bath (80 rpm, 30 minutes) at 37° C. The suspension was filtered through a 120 and 45 µm nylon mesh, respectively. The cell-suspension was cultured for 3 days in DMEM+S in 250 ml plastic tissue culture flasks (Greiner B. V., Alphen a/d Rijn, The Netherlands) in a humidified incubator (Napco Scientific Company, Tualatin, Oreg., USA) at 37° C. in a mixture of air with 10% $CO_2$. Thereafter, the medium was refreshed every other day. After 7 days of culturing, other cells than astrocytes were removed by shaking the cultures in a shaking water bath (80 rpm) overnight at room temperature. Two days later the cultures were passaged with 0.05% (w/v) trypsin-EDTA in a split ratio of 1:3 to poly-D-lysine coated flasks (overnight stirred 10 µg/ml poly-D-lysine solution, air dried and washed with LPSS (3 times)). When confluent, astrocyte conditioned medium was collected, every other day, for 2-4 weeks, sterile filtered and stored at −20° C. For co-culture purpose, 2 weeks old cultures were passaged and stored in freeze mix in liquid nitrogen.

1.1.3 Differential Seeding of Brain Capillaries and Culture of BCEC

Brain capillaries were seeded in collagen (human placenta type IV, 10 µg/ml solution in 0.1% (v/v) acetic acid for 2 hours and washed with LPSS 3 times) and human plasma fibronectin (10 µg/ml solution in LPSS, 30 minutes) coated 250 ml plastic tissue culture flasks and allowed to adhere for 4 hours in the incubator. Thereafter, the culture medium was replaced with growth medium (DMEM+S with 50% (v/v) astrocyte conditioned medium, supplemented with 125 µg/ml heparin) and the outgrowing cells, predominately BCEC and some pericytes, were cultured at 37° C., 10% $CO_2$.

1.1.4 Preparation of the In Vitro BBB on Filters

The in vitro BBB model was prepared on collagen coated (as above) Transwell polycarbonate filters (surface area: 0.33 $cm^2$, pore-size: 0.4 µm, Corning Costar, Cambridge, Mass., USA). At about 70% confluence (day 4 or 5 after seeding of the brain capillaries), BCEC were passaged with trypsin-EDTA for endothelial cells (500 BAEE units porcine trypsin and 180 µg EDTA per ml) for approximately 1 minute, leaving the majority of pericytes still adhered to the substratum. BCEC and astrocyte co-cultures were prepared with astrocytes seeded on the bottom of the filter at a density of 45000 astrocytes per filter. Astrocytes were allowed to adhere to the bottom of the filter for 8 minutes, 2 or 3 days before BCEC were passaged. BCEC were seeded at a density of 30000 BCEC per filter. BCEC+astrocyte co-cultures were cultured to tight monolayers in DMEM+S supplemented with 125 µg/ml heparin for the first 2 days and in DMEM+S for the last 2 days. BCEC monolayers were cultured accordingly, but with 50% (v/v) astrocyte conditioned medium added to the culture medium.

1.2 Affymetrix Genechip® Gene Expression Analysis 1.2.1 Isolation of Total RNA

In case of BCEC+astrocyte co-cultures, astrocytes were removed prior to BCEC RNA isolation by scraping the basolateral side of the Transwell filters. Total RNA was isolated from BCEC (containing <5% pericytes (Gaillard et al., 2001, supra)) using the RNeasy mini kit (Qiagen, Hilden, Germany). For this, the cell-culture medium was removed and replaced by 40 µl of lysis buffer per Transwell filter. Subsequently, lysates were resuspended and collected from multiple (12-18) Transwell filters, whereupon the manufacturer's recommended procedures for the isolation of total RNA from animal cells was followed. QIA shredders were used to homogenize cell lysates. When necessary, total RNA was concentrated with sodium acetate and ethanol.

1.2.2 Preparation of Labeled RNA

Subsequent protocols for the preparation of biotinylated cRNA from total RNA for Affymetrix GeneChip® gene expression analysis were performed according to the manufacturer's recommendations, as described in the Affymetrix GeneChip® Expression Analysis Manual (Affymetrix, Santa Clara, Calif., USA). Briefly, 6-16 µg of total RNA per sample was used for double-stranded cDNA synthesis using the Gibco BRL Superscript Choice System (Life Technologies, Rockville, Md., USA). A T7-dT24 primer and Superscript II reverse transcriptase (Life Technologies, Rockville, Md., USA) were utilized for first-strand synthesis. The second-strand synthesis involved E. coli DNA polymerase I (Life Technologies, Rockville, Md., USA). The double-stranded cDNA was then purified using phenol/chloroform extraction (utilizing phase lock gels (Eppendorf AG, Hamburg, Germany)) followed by precipitation with ammonium acetate and ethanol. Biotinylated cRNA was synthesized by in vitro transcription from cDNA using the BioArray HighYield RNA Transcript Labeling Kit (Enzo Diagnostics, Farmingdale, N.Y., USA), by incubation at 37° C. for 5 hours. The labeled cRNA was then purified using the RNA cleanup protocol of the RNeasy mini kit (Qiagen, Hilden, Germany). Subsequently, 15-20 µg of labeled cRNA was fragmented by heating at 94° C. for 35 minutes in fragmentation buffer (40 mM Tris-acetate (pH 8.1), 125 mM KOAc, 30 mM MgOAc).

1.2.3 GeneChip® Hybridization

Labeled and fragmented cRNA was hybridized to the HG-U95Av2 and HG-U133A array (Affymetrix, Santa Clara, Calif., USA) under conditions recommended by the manufacturer. cRNA was first hybridized to a Test2 Chip (Affymetrix), to ensure the quality of the preparation. In brief, cRNA was diluted in hybridization mix (1×MES hybridization buffer, 100 µg/ml herring sperm, 50 µg/ml acetylated BSA, control oligonucleotide B2 and eukaryotic hybridization controls) denatured and then hybridized for 16 hours at 45° C. at 60 rpm. Following hybridization, arrays were washed and stained with streptavidin-phycoerythrin using the Affymetrix Genechip® Fluidics Station 400. Fluorescent signals on the arrays were measured using the Hewlett-Packard Affymetrix GeneArray® scanner.

Example 1

Identification of "Lipopolysaccharide-Sensitive" Genes, Differentially Expressed in and Between BCEC-ACM Monolayers and BCEC-Astrocyte Cocultures In earlier experiments (as detailed in Gaillard (2000a, supra), which is included as a reference), we found that astrocytes and inflammatory processes (mimicked by lipopolysaccharide, LPS) display opposing effects in our dynamic co-culture model of the BBB. Briefly, astrocytes increase barrier functionality, whereas LPS decreases it. Moreover, astrocytes bring about a recovery process from LPS which was not observed without the physical presence of astrocytes (i.e., in BCEC-ACM monolayers). Finally, this recovery process was dependent on protein synthesis, which indicates that specific gene transcription is involved. In FIG. 2, this experimental approach is schematically detailed.

Figure 1A:
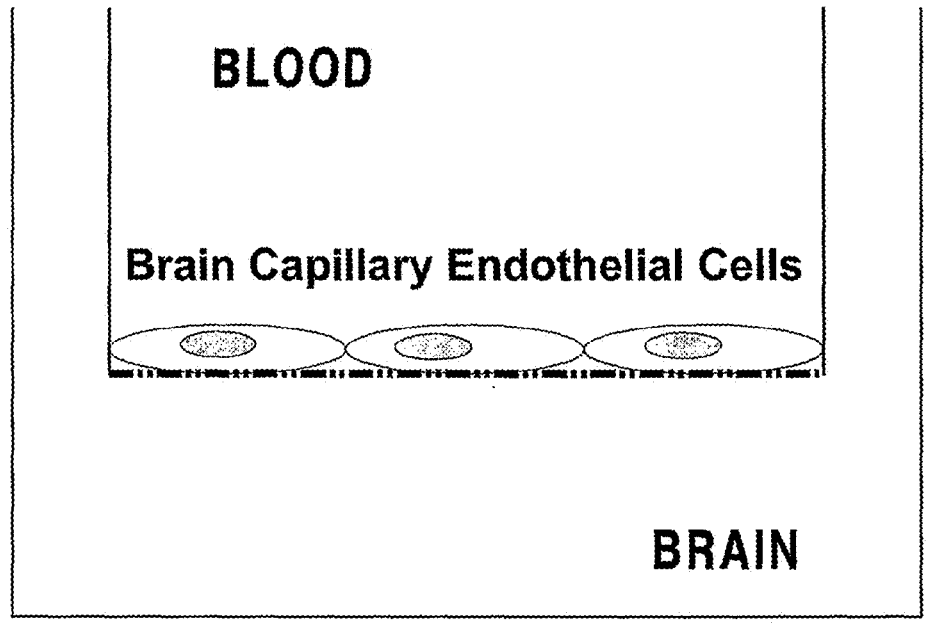
FIG. 1 is a schematically detailed representation of a filter insert with BCEC-ACM monolayers (panel a) and with BCEC-Astrocytes cocultures (panel b).

For the identification of the involved LPSS genes, and their involvement in the recovery process, four different cell culture conditions for our BCEC cultured from primary isolated brain capillaries from calf brain were used (as detailed in Gaillard et al., 2001, supra, which is included as a reference and briefly herein in "1.1 Cell Culture"): 1) BCEC monolayers on filter inserts in 50% ACM (FIG. 1a: BCEC-ACM). 2) BCEC monolayers on filter inserts in 50% ACM, apically exposed to 1 microgram/ml LPS (serotype 055:B5) for 2 hours; 3) BCEC monolayers on filter inserts with primary isolated newborn rat brain astrocytes cultured on the bottom side of the filter insert (FIG. 1b: BCEC-Astrocytes); 4) BCEC monolayers on filter inserts with primary isolated newborn rat brain astrocytes cultured on the bottom side of the filter insert, apically exposed to 1 microgram/ml LPS (serotype 055:B5) for 2 hours. The LPS treated BCEC (conditions 2 and 4) were compared to the results found in the untreated BCEC (conditions 1 and 3).

After 2 hours of exposure to LPS, BBB functionality was assessed by TEER across the filters using an electrical resistance system (ERS) with a current-passing and voltage-measuring electrode (Millicell-ERS, Millipore Corporation, Bedford, Mass., USA). TEER (Ohm·cm$^2$) was calculated from the displayed electrical resistance on the readout screen by subtraction of the electrical resistance of a collagen coated filter without cells and a correction for filter surface area. TEER across collagen coated filters with only astrocytes on the bottom was close to zero (Gaillard et al., 2001, supra).

Figure 3A:
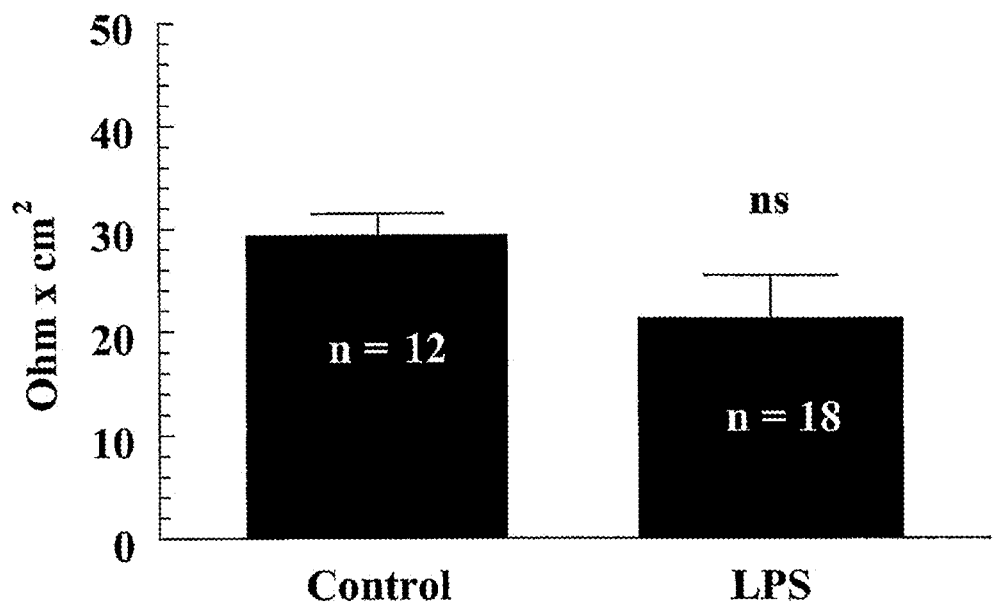
FIG. 3 is a diagram showing the effect on TEER across BCEC-ACM monolayers of 2 hours exposure to LPS, expressed in Ohm·cm$^2$ (mean±standard error, panel a) and as % of control (i.e., untreated BCEC-ACM monolayers, mean±standard error, panel b).
Figure 3B:
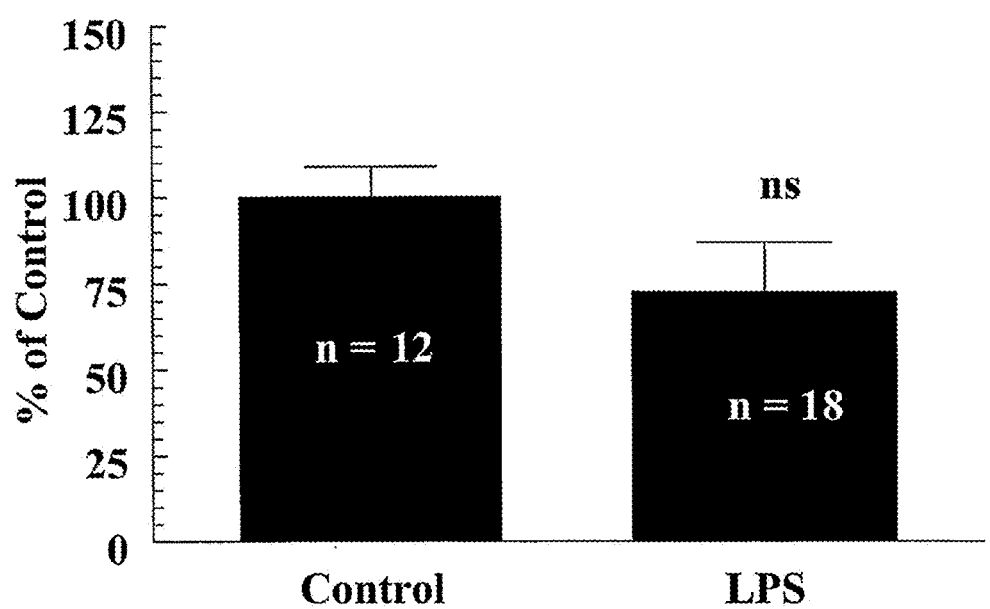

The average TEER across BCEC-ACM monolayers was 29.3±2.1 Ohm·cm$^2$ (mean±standard error, n=12) before exposure to LPS and decreased to 21.2±4.2 Ohm·cm$^2$ (mean±standard error, n=18) after 2 h of LPS exposure. See FIG. 3a for a graphic representation of the results. This decrease in TEER cannot be considered significant according to the Unpaired t-test (p>0.05). Accordingly, TEER decreased to 72.4±14.3% (mean±standard error, n=18) when compared to untreated BCEC-ACM monolayers (see FIG. 3b for a graphic representation).

Figure 4A:
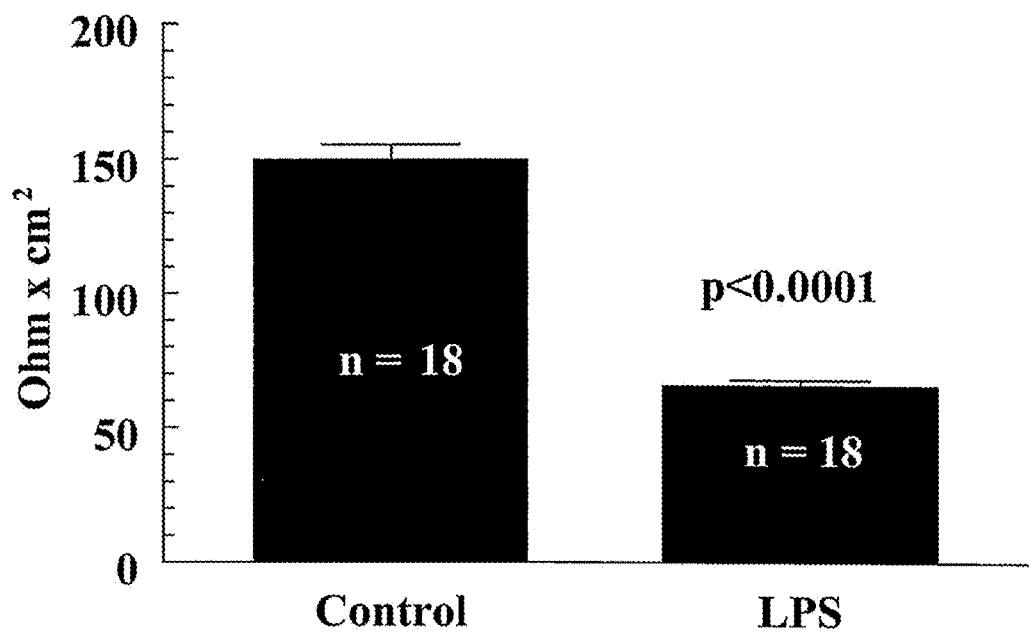
FIG. 4 is a diagram showing the effect on TEER across BCEC-Astrocytes cocultures of 2 hours exposure to LPS, expressed in Ohm·cm$^2$ (mean±standard error, panel a) and as % of control (i.e., untreated BCEC-Astrocytes cocultures, mean±standard error, panel b).
Figure 4B:
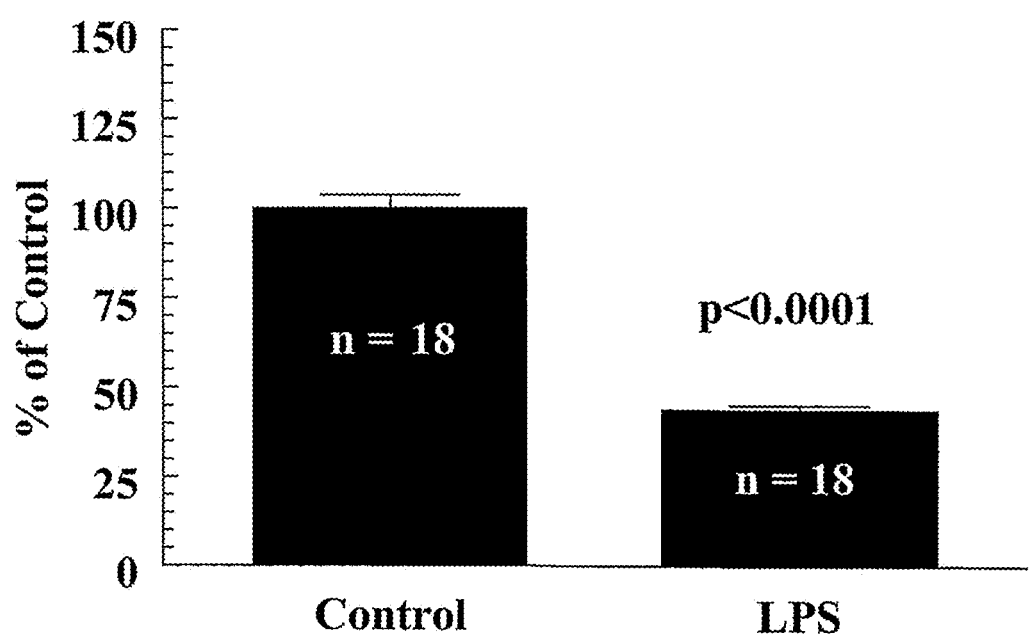

The average TEER across BCEC-Astrocytes cocultures was 149.8±5.4 Ohm·cm$^2$ (mean±standard error, n=18) before exposure to LPS and decreased to 65.5±2.1 Ohm·cm$^2$ (mean±standard error, n=18) after 2 h of LPS exposure. See FIG. 4a for a graphic representation of the results. This decrease in TEER can be considered extremely significant according to the Unpaired t-test (p<0.0001). Accordingly, TEER decreased to 43.7±1.4% (mean±standard error, n=18) when compared to untreated BCEC-Astrocytes cocultures (see FIG. 4b for a graphic representation).

For all experimental conditions (BCEC-ACM monolayers±LPS and BCEC-Astrocytes cocultures±LPS) the RNA isolation, labeling of cRNA and hybridization protocol was performed in triplo and all samples were analyzed on both the HG-U95Av2 and HG-U133A arrays. Affymetrix Microarray Suite 5.0 and Affymetrix Data Mining Tool 2.0 were used for primary analysis of the acquired intensity data. Microsoft Excel (Microsoft, USA) was used for further analysis. Global scaling, where the data of each chip is scaled to a user-defined target intensity, was performed to make experiments comparable. Genes that were designated as "absent" by Affymetrix Microarray Suite 5.0 in all samples were eliminated from further analysis. When applicable, only the genes that were designated as "present" or as "marginally present" in all three "triplo" samples were included for further analysis. Mann-Whitney tests were performed to identify genes that were statistically significant differentially expressed (between control BCEC-ACM monolayers and LPS-treated BCEC-ACM monolayers; between control BCEC-Astrocytes cocultures and LPS-treated BCEC-Astrocytes cocultures; between LPS-treated BCEC-ACM monolayers and LPS-treated BCEC-Astrocytes cocultures). Differences were considered to be statistically significant when p-value was <0.05. Furthermore, for the LPS effect between BCEC-ACM monolayers and BCEC-Astrocytes cocultures, fold changes were calculated based on the average intensity value (only changes of 2 fold or more were considered biologically relevant).

The identified genes are designated herein as "lipopolysaccharide-sensitive (LPSS)" genes, and coded accordingly (LPSS01-LPSS25) and presented in Table 1. Included are also the SEQ ID NOs, LPS effect (up, down, differentially expressed (dif+ or dif−)), the accession codes for reference in publicly accessible databases (RefSeq), the gene symbol, and a description (title or gene name) for the LPSS gene. For each identified LPSS gene, the specific result is presented in Table 2.

Example 2

Characterization of LPSS14 (DTR) in BCEC-Astrocyte Cocultures

Figure 1B:
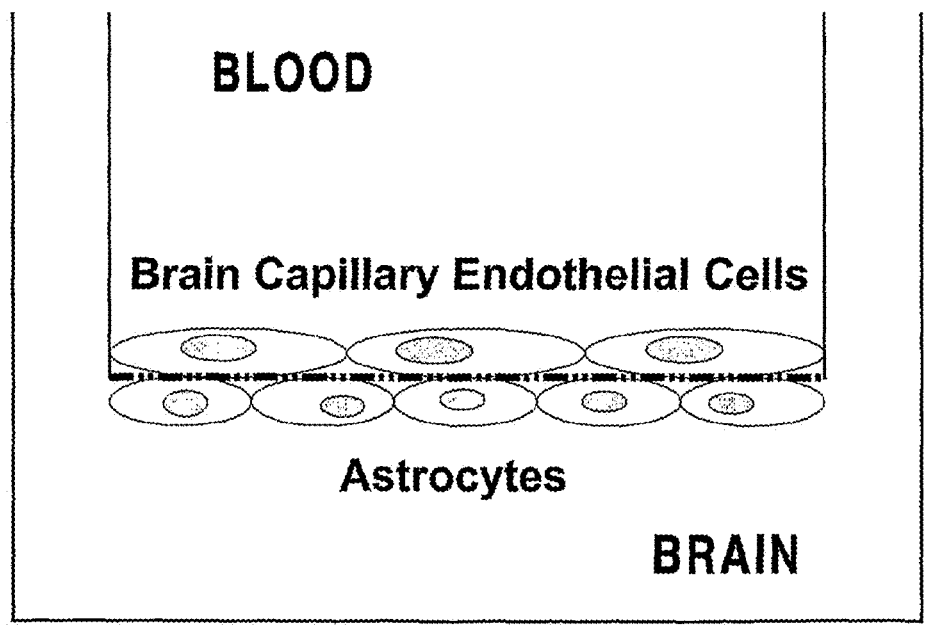
Figure 7:
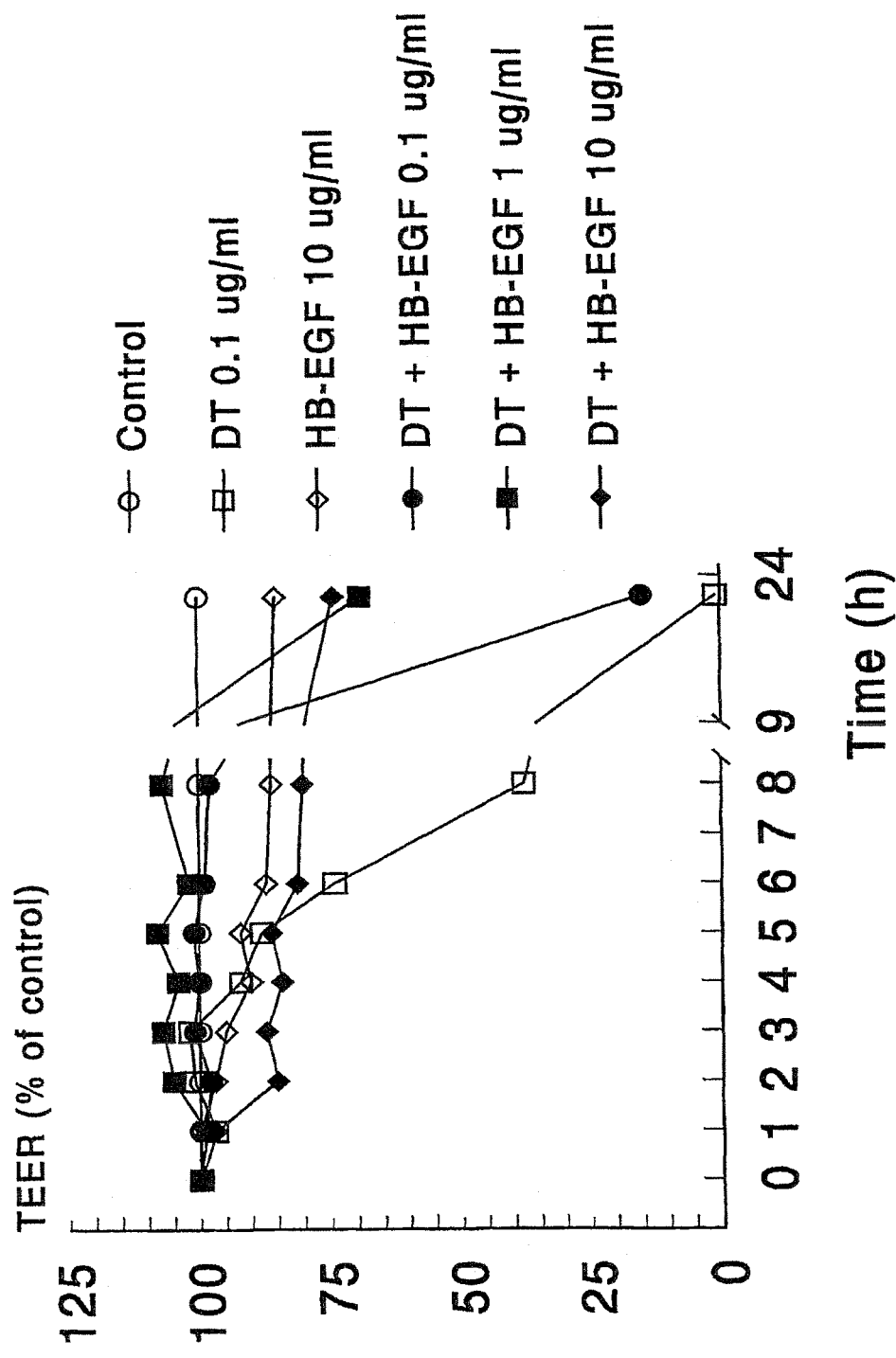
FIG. 7 is a diagram showing the effect on TEER (expressed as mean % of control) across BCEC-Astrocytes cocultures exposed to 100 ng/ml DT which was preincubated (1 hour at room temperature) with various concentrations of soluble HB-EGF (0.1-10 microgram/ml), acting as a non-competitive antagonist for the DTR by binding to the receptor-binding domain of DT, before it was exposed to the apical side of the filter.
Figure 8:
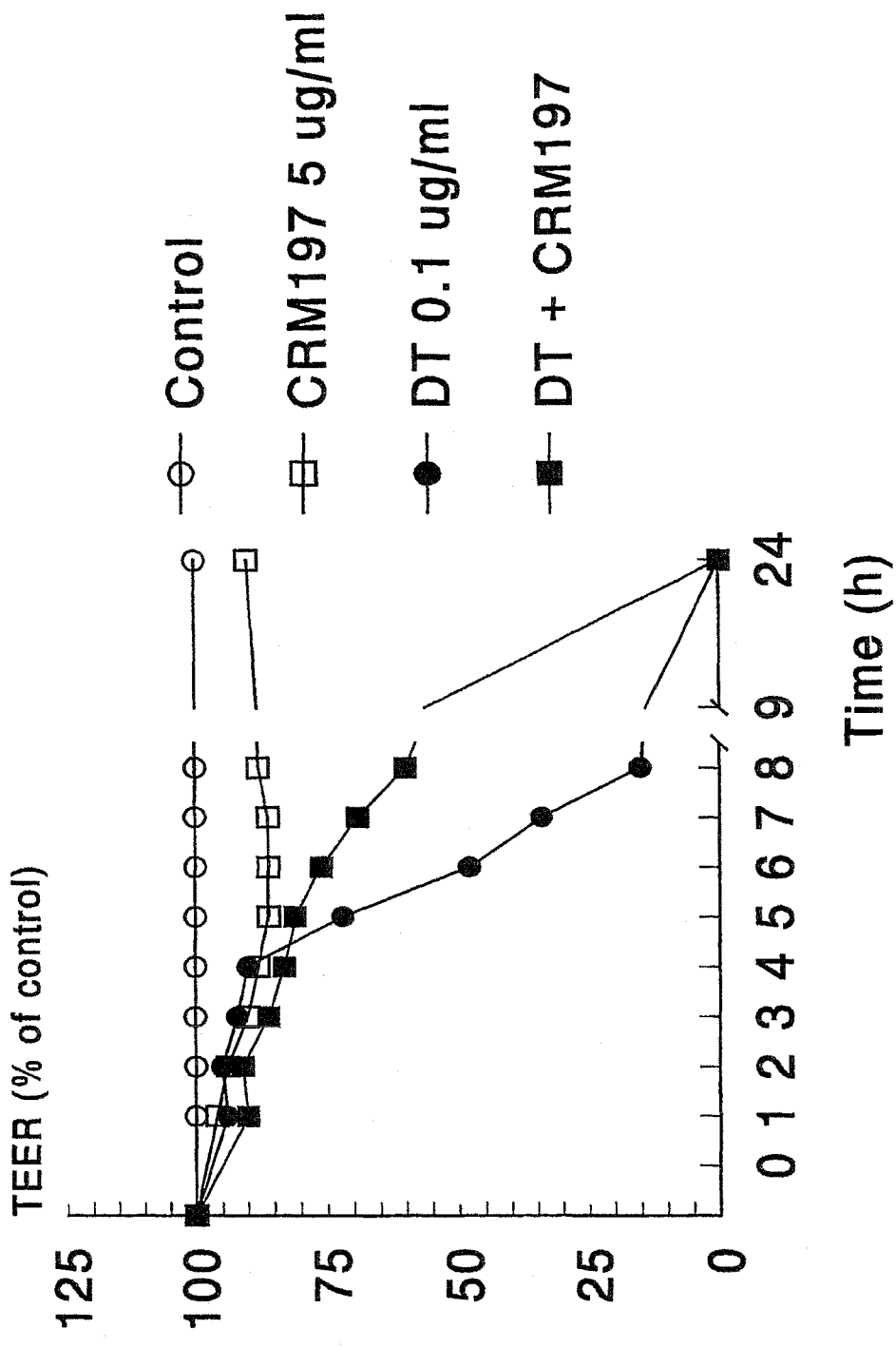
FIG. 8 is a diagram showing the effect on TEER (expressed as mean % of control) across BCEC-Astrocytes cocultures pretreated for 1 hour with 5 microgram/ml of CRM197, acting as a competitive antagonist at the DTR by binding to the receptor-binding domain for DT, before the BCEC were exposed to 100 ng/ml DT.

For the characterization of LPSS14 (DTR) on the blood-brain barrier, BCEC cultured from primary isolated brain capillaries from calf brain were used as monolayers on filter inserts with primary isolated newborn rat brain astrocytes cultured on the bottom side of the filter insert (FIG. 1b: BCEC-Astrocytes, as detailed in Gaillard et al., 2001, supra, which is included as a reference and briefly herein in "1.1 Cell Culture"). We used: 1) BCEC exposed to various concentrations (1 ng/ml up to 10 microgram/ml) of DT on the apical (blood) side of the filter (results are depicted in FIG. 5); 2) like 1, but then DT was exposed to the basolateral (brain) side of the filter (results are depicted in FIG. 6); 3) BCEC exposed to 100 ng/ml DT which was preincubated (1 hour at room temperature) with various concentrations of soluble HB-EGF (0.1-10 microgram/rid), acting as a non-competitive antagonist for the DTR by binding to the receptor-binding domain of DT, before it was exposed to the apical side of the filter (results are depicted in FIG. 7); 4) BCEC pretreated for 1 hour with 5 microgram/ml of CRM197, acting as a competitive antagonist at the DTR by binding to the receptor-binding domain for DT, before the BCEC were exposed to 100 ng/ml DT (results are depicted in FIG. 8).

Every hour after exposure to DT, BBB functionality was assessed by TEER across the filters using an electrical resistance system (ERS) with a current-passing and voltage-measuring electrode (Millicell-ERS, Millipore Corporation, Bedford, Mass., USA). TEER (Ohm·cm$^2$) was calculated from the displayed electrical resistance on the readout screen by subtraction of the electrical resistance of a collagen coated filter without cells and a correction for filter surface area. TEER across collagen coated filters with only astrocytes on the bottom was close to zero (Gaillard et al., 2001, supra). Effects on TEER were normalized for control treated filters and represented as such.

Figure 5:
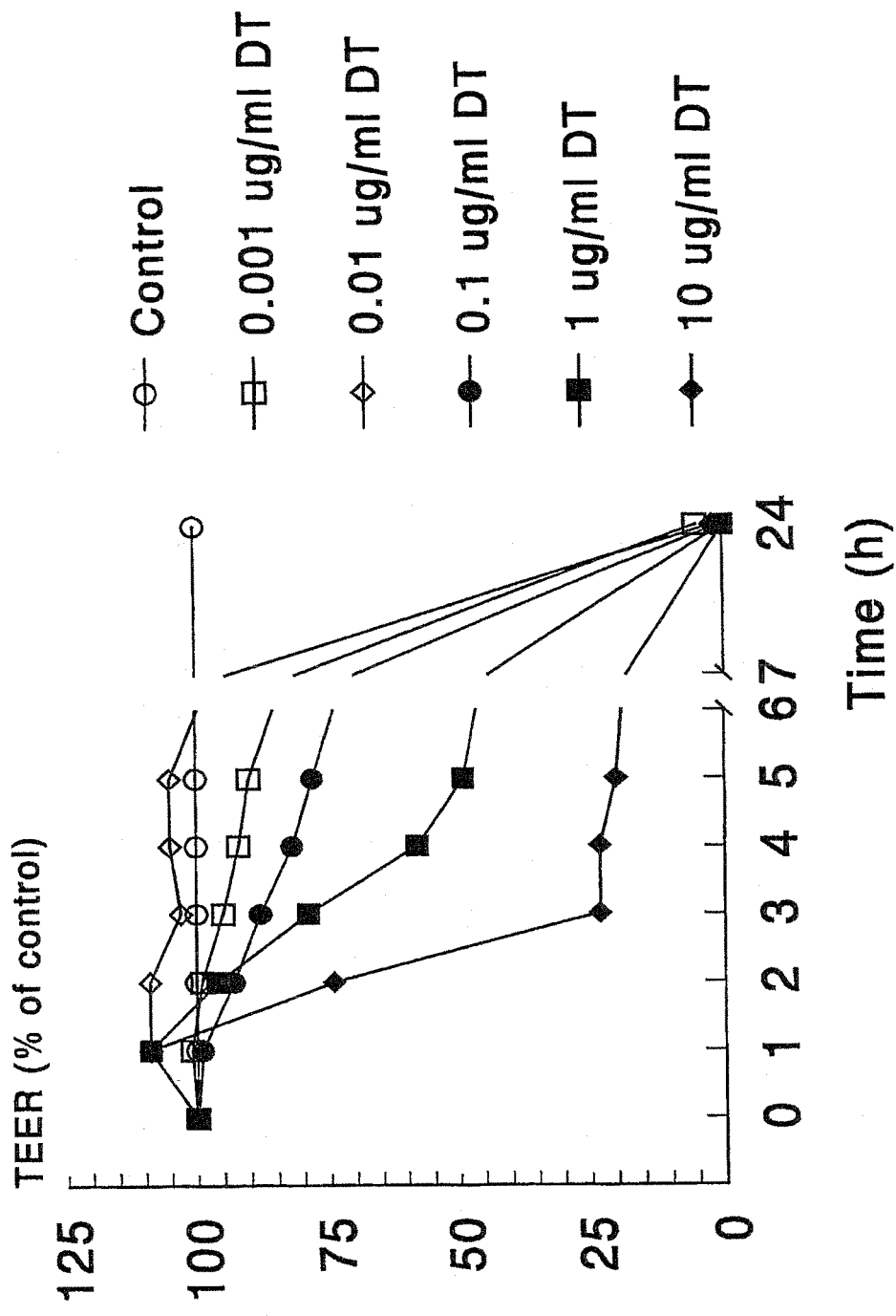
FIG. 5 is a diagram showing the effect on TEER (expressed as mean % of control) across BCEC-Astrocytes cocultures exposed to various concentrations (1 ng/ml up to 10 microgram/ml) of DT on the apical (blood) side of the filter.

After apical exposure to 1 ng/ml up to 10 microgram/ml of DT, the TEER across BCEC-Astrocytes cocultures decreased in a concentration- and time dependent manner, while concentrations as low as 1 ng/ml were toxic after an overnight incubation period (FIG. 5). These results indicate that DT is effectively taken up from the apical site by BCEC in which it can exert its toxic effects.

Figure 6:
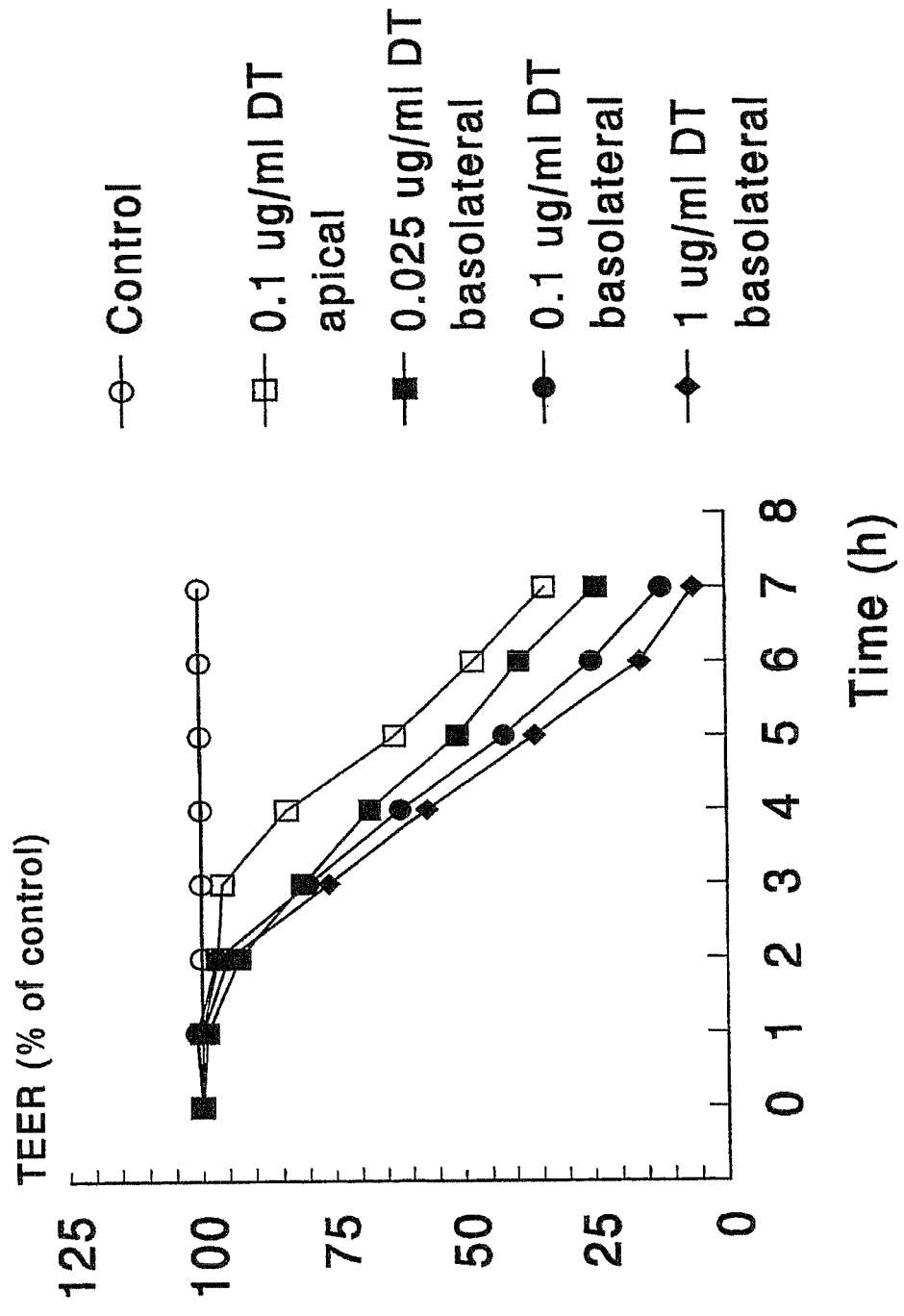
FIG. 6 is a diagram showing the effect on TEER (expressed as mean % of control) across BCEC-Astrocytes cocultures exposed to various concentrations (25 ng/ml up to 1 microgram/ml) of DT on the basolateral (brain) side of the filter.

After basolateral exposure to 25 ng/ml up to 1000 ng/ml of DT, the TEER across BCEC-Astrocytes cocultures decreased in a concentration- and time dependent manner, while when compared to equimolar apical concentrations or amounts of DT these effects occurred about 1 hour earlier (FIG. 6). These results indicate that, when compared to apical exposure, DT is more effectively taken up by BCEC from the basolateral site.

After apical exposure to 100 ng/ml DT which was preincubated with soluble HB-EGF, the toxic effect of DT on BCEC-Astrocytes cocultures decreased in a concentration dependent manner (FIG. 7). In fact, a preincubation of 100 ng/ml DT with 10 microgram/ml of soluble HB-EGF completely prevented the DT-induced toxic effect on BCEC, even after an overnight assessment. These results indicate that DT-uptake in BCEC is effectively blocked by previous specific binding of DT to its soluble receptor, making it unable to exert its toxic effects within the BCEC.

After BCEC were preincubated with CRM197, the toxic effect after apical exposure to 100 ng/ml DT on BCEC-Astrocytes cocultures decreased (FIG. 8). These results indicate that DT-uptake in BCEC is effectively antagonized by previous specific binding of CRM197 to the DTR, making it less available for DT to exert its toxic effects within the BCEC.

Example 3

Figure 9:
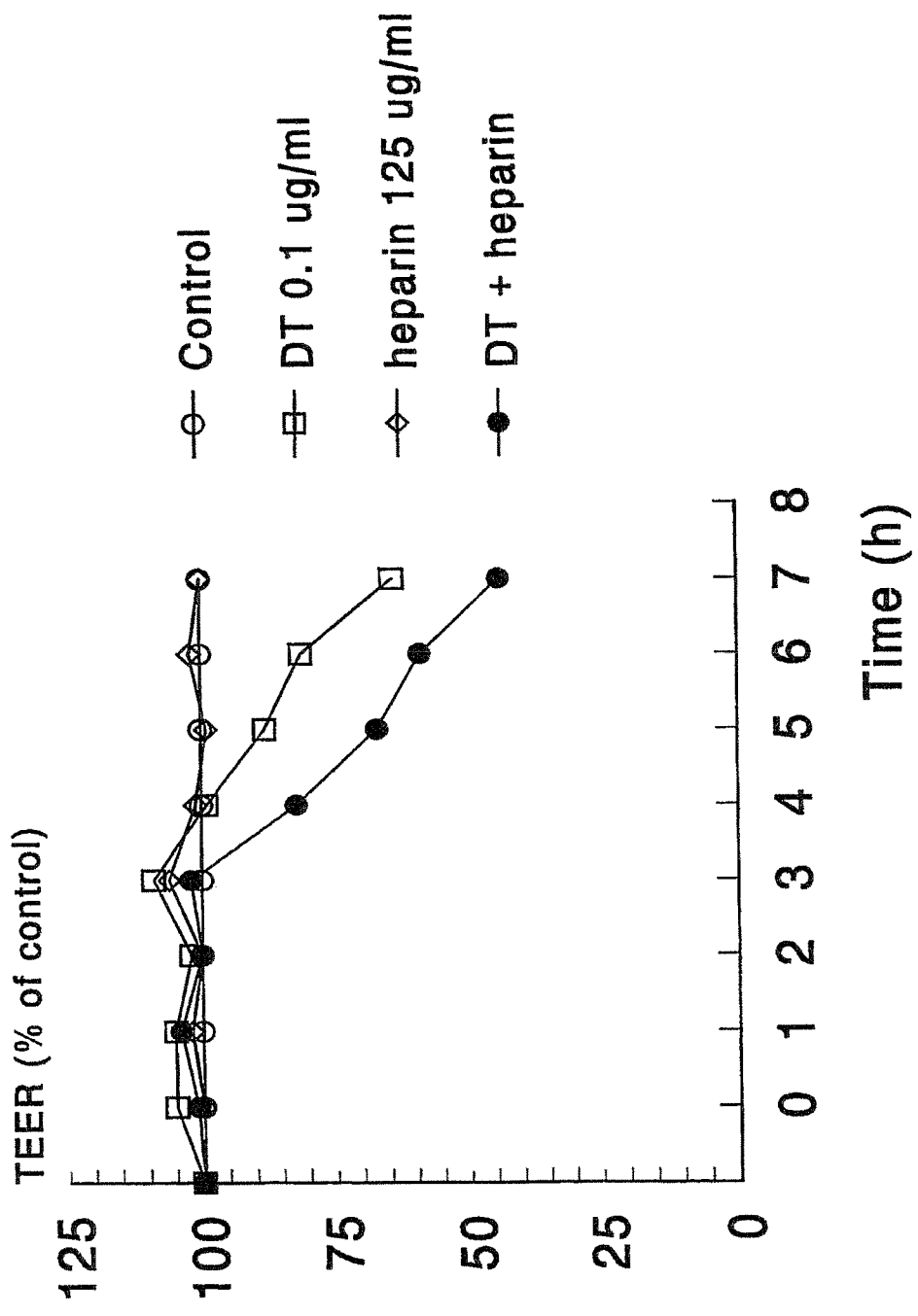
FIG. 9 is a diagram showing the effect on TEER (expressed as mean % of control) across BCEC-astrocyte cocultures pretreated for 1 hour with heparin (125 microgram/ml), acting as an enhancer of DT binding at the DTR by introducing a conformational change in the receptor-binding domain for DT, before the BCEC were exposed to 100 ng/ml DT.

Modulation of the Biological Activity of LPSS14 (DTR) in BCEC-Astrocyte Cocultures For the modulation of the biological activity of LPSS14 (DTR) on the blood-brain barrier, BCEC cultured from primary isolated brain capillaries from calf brain were used as monolayers on filter inserts with primary isolated newborn rat brain astrocytes cultured on the bottom side of the filter insert (FIG. 1b: BCEC-Astrocytes, as detailed in Gaillard et al., 2001, supra, which is included as a reference and briefly herein in "1.1 Cell Culture"). We used: 1) BCEC pretreated for 1 hour with heparin (125 microgram/ml), acting as an enhancer of DT binding at the DTR by introducing a conformational change in the receptor-binding domain for DT, before the BCEC were exposed to 100 ng/ml DT (results are depicted in FIG. 9); 2) BCEC apically exposed to 1 microgram/ml LPS (serotype 055:B5) for 2 hours, thereby increasing the level of expression of DTR, before the BCEC were exposed to 100 ng/ml DT (results are depicted in FIG. 10); 3) BCEC apically exposed to 10 micromolar BB94 (batimastat) for 1 hour, acting as an inhibitor of MMP's involved in the process of ectodomain shedding, thereby increasing the availability of DTR on the cell membrane, before the BCEC were exposed to 100 ng/ml DT (results are depicted in FIG. 10); 4) the combination of LPS (2) and BB94 (3), thereby increasing both the level of expression and the availability of DTR on the cell membrane, before the BCEC were exposed to 100 ng/ml DT (results are depicted in FIG. 10).

Every hour after exposure to DT, BBB functionality was assessed by TEER across the filters using an electrical resistance system (ERS) with a current-passing and voltage-measuring electrode (Millicell-ERS, Millipore Corporation, Bedford, Mass., USA). TEER (Ohm·cm$^2$) was calculated from the displayed electrical resistance on the readout screen by subtraction of the electrical resistance of a collagen coated filter without cells and a correction for filter surface area. TEER across collagen coated filters with only astrocytes on the bottom was close to zero (Gaillard et al., 2001, supra). Effects on TEER were normalized for control treated filters and represented as such.

After BCEC were preincubated with heparin, the toxic effect after apical exposure to 100 ng/ml DT on BCEC-Astrocytes cocultures increased in a way that the effect took place about 1 hour earlier then untreated controls (FIG. 9), consistent with the level of toxicity measured after a 10-fold higher concentration of DT. These results indicate that DT-uptake in BCEC is effectively increased by heparin.

Figure 10:
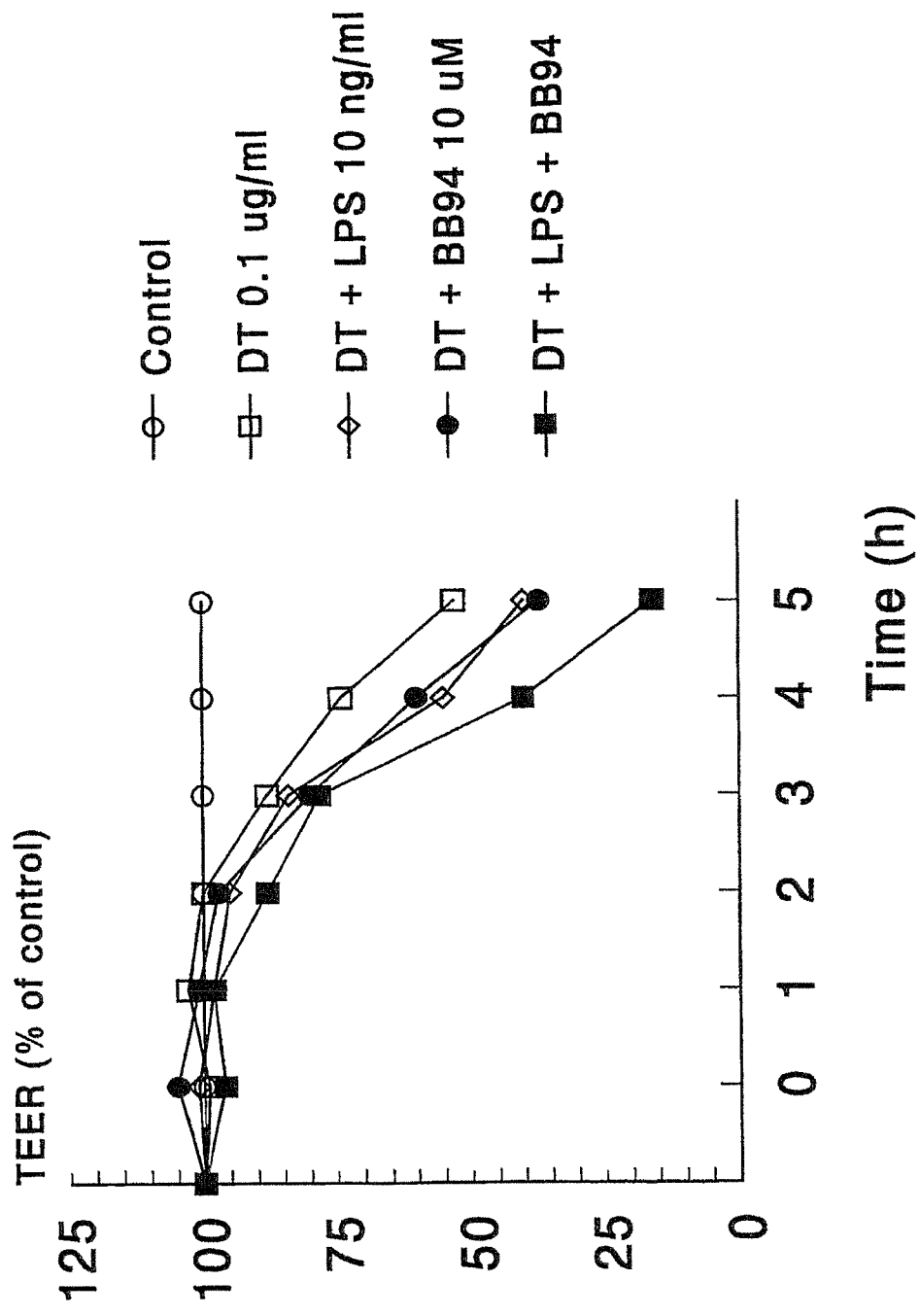
FIG. 10 is a diagram showing the effect on TEER (expressed as mean % of control) across BCEC-astrocyte cocultures apically exposed to 1 microgram/ml LPS (serotype 055: B5) for 2 hours, thereby increasing the level of expression of DTR, or 10 micromolar BB94 (batimastat) for 1 hour, acting as an inhibitor of MMP's involved in the process of ectodomain shedding, thereby increasing the availability of DTR on the cell membrane, or the combination of LPS and BB94, thereby increasing both the level of expression and the availability of DTR on the cell membrane, before the BCEC were exposed to 100 ng/ml DT.

After BCEC were preincubated with LPS or BB94, the toxic effect after apical exposure to 100 ng/ml DT on BCEC-Astrocytes cocultures moderately increased in a way that the effect took place faster then in untreated controls (FIG. 10). Moreover, when BCEC were preincubated with both LPS and BB94 together, the toxic effect after apical exposure to 100 ng/ml DT on BCEC-Astrocytes cocultures increased in a way that the effect took place much faster then in untreated controls and in separately treated BCEC (FIG. 10). These results indicate that DT-uptake in BCEC is effectively increased by LPS (probably due to increased DTR expression) and BB94 (probably due to increased DTR availability by inhibited ectodomain shedding), and that these are additive effects.

Example 4

Figure 14:
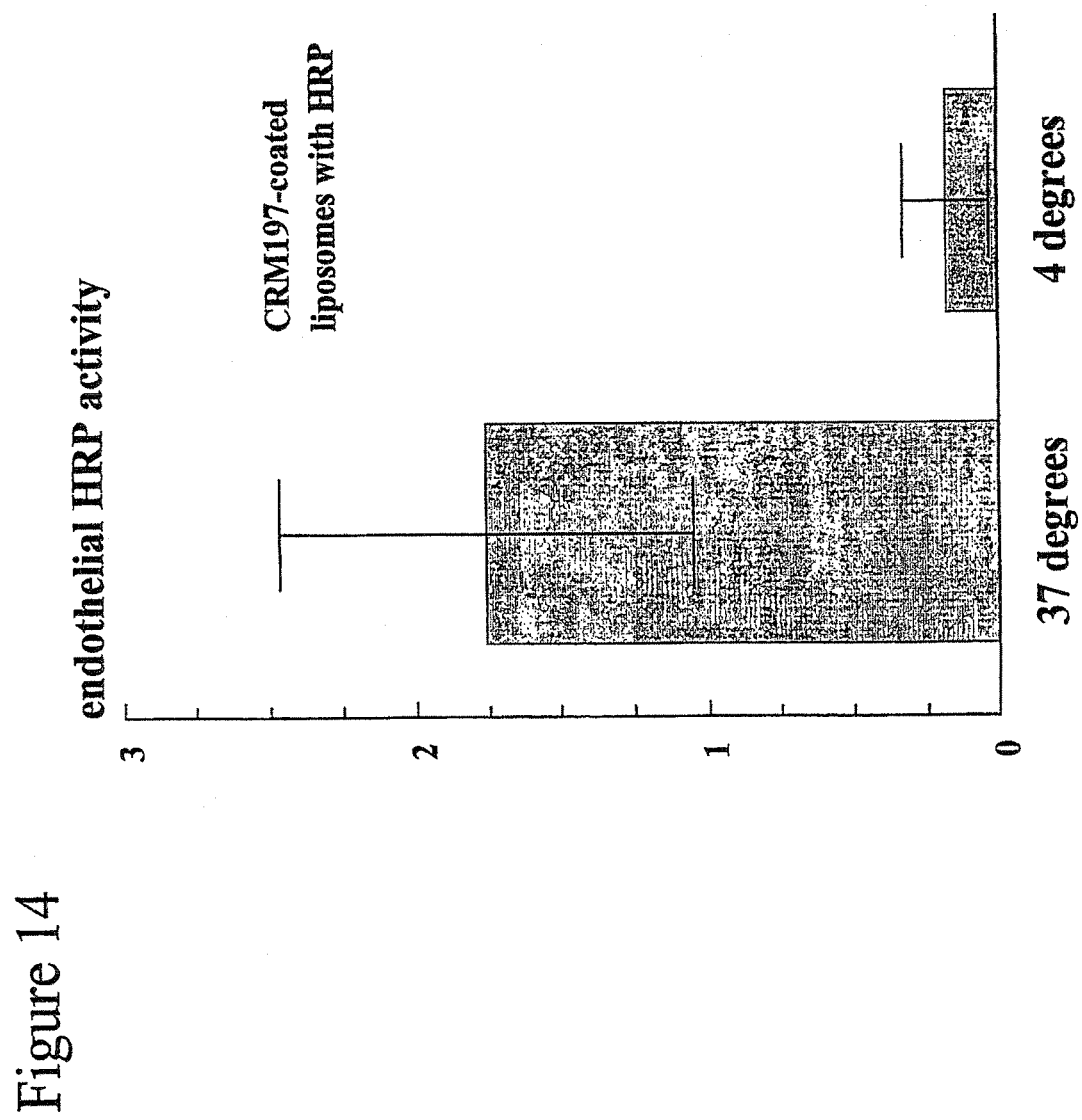
FIG. 14 is a diagram showing HRP activity in BCEC lysates after exposure to HRP-loaded CRM197-coated PEG-liposomes corresponding to a concentration of 5 microgram/ml of free HRP at 37° C. and 4° C. (to inhibit active uptake), indicating that the HRP-loaded CRM197-coated PEG-liposomes were actively taken up by the BCEC.
Figure 15:
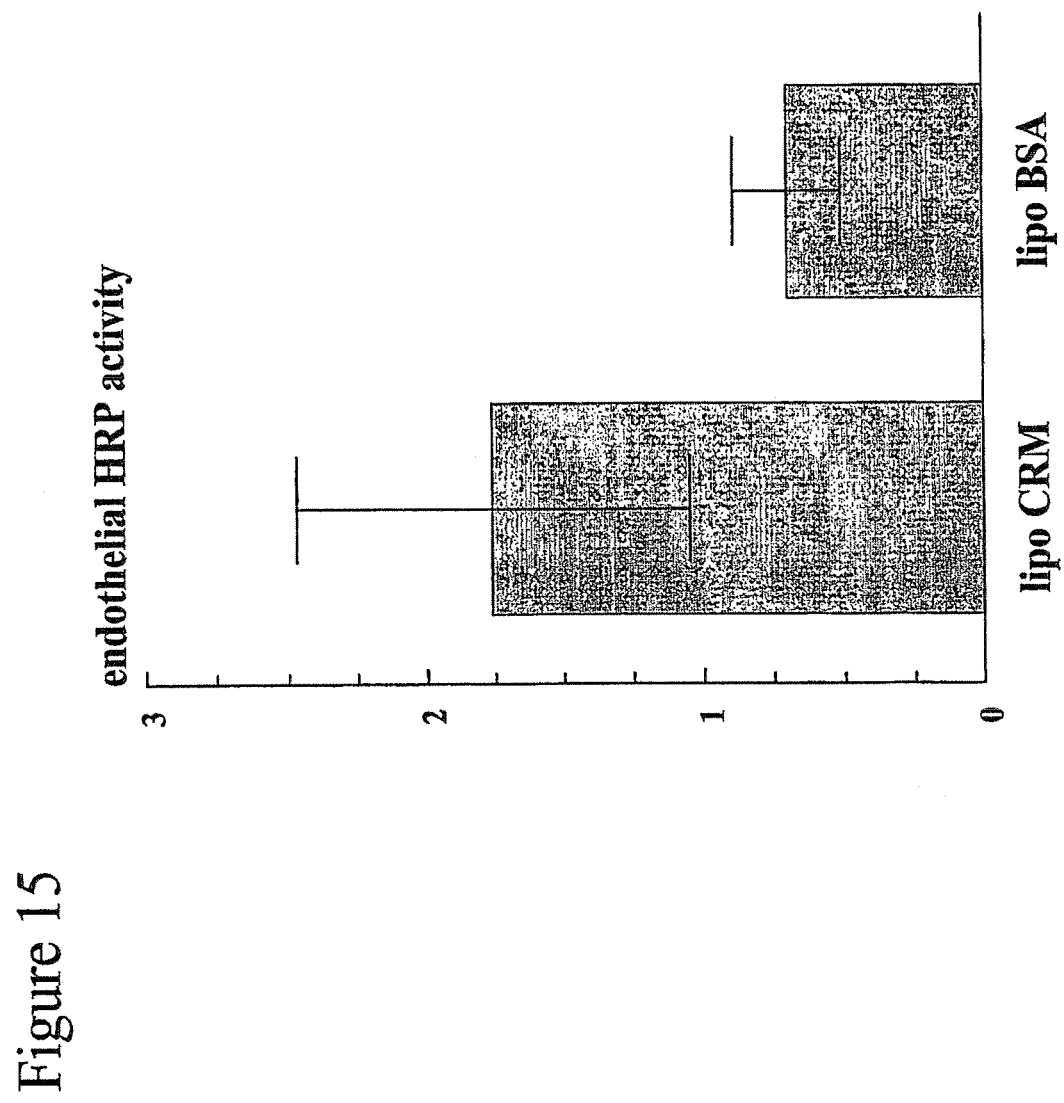
FIG. 15 is a diagram showing HRP activity in BCEC lysates after exposure to concentrations corresponding to 5 microgram/ml of free HRP of either HRP-loaded CRM197-coated PEG-liposomes or HRP-loaded BSA-coated PEG-liposomes (to determine the carrier specificity), indicating that the HRP-loaded CRM197-coated PEG-liposomes were specifically taken up by the BCEC.
Figure 16:
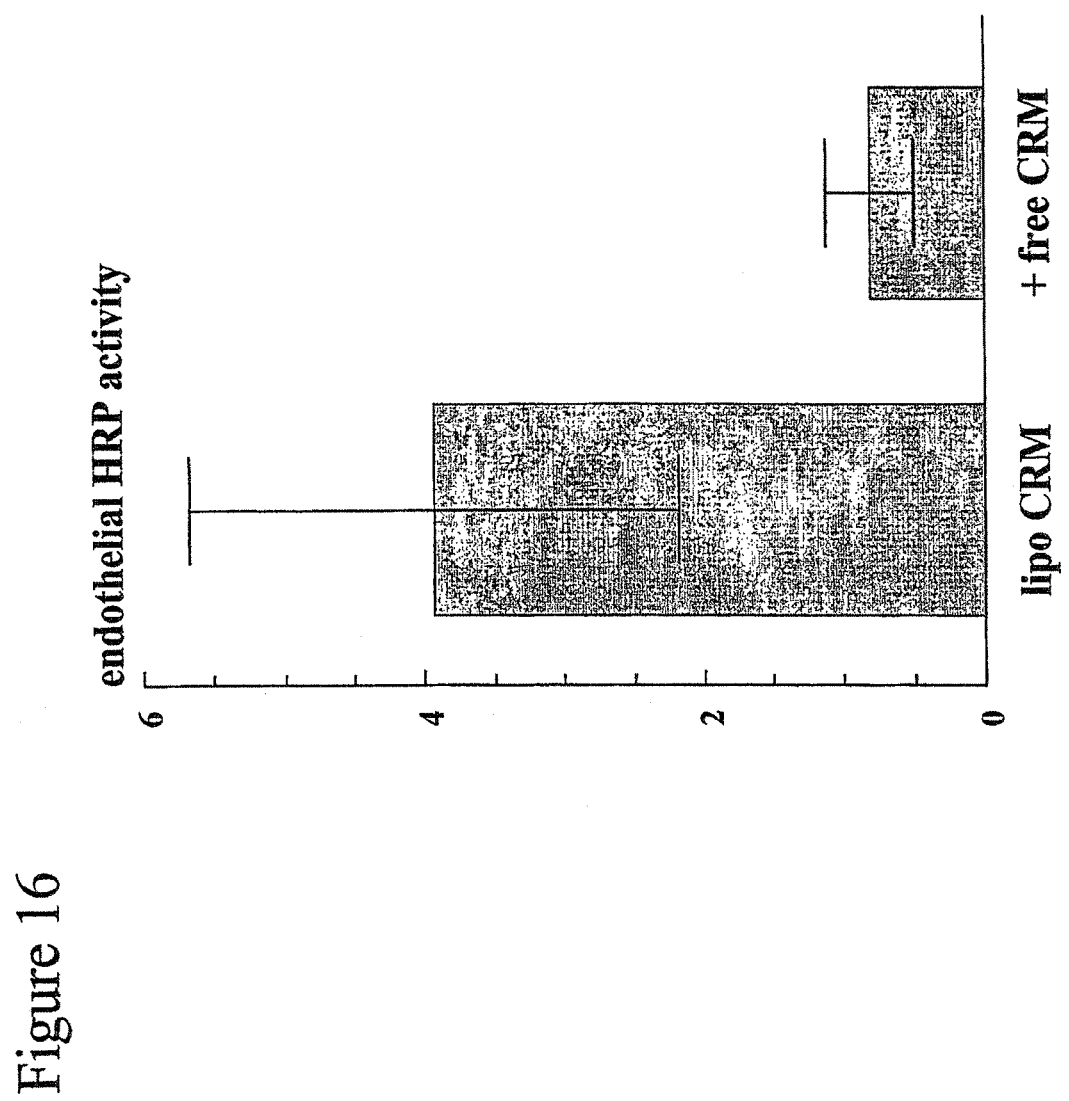
FIG. 16 is a diagram showing HRP activity in BCEC lysates after exposure to HRP-loaded CRM197-coated PEG-liposomes corresponding to a concentration of 5 microgram/ml of free HRP and compared to the uptake in BCEC that were pretreated for 1 hour with 50 microgram/ml of free CRM197 (to determine the specific involvement of the DTR), indicating that the HRP-loaded CRM197-coated PEG-liposomes were indeed specifically taken up by the BCEC via the DTR.

Drug Targeting to the Blood-Brain Barrier via LPSS14 (DTR): In Vitro Uptake Studies For the assessment of the blood-brain barrier drug targeting ability via LPSS14 (DTR), BCEC cultured from primary isolated brain capillaries from calf brain were used as monolayers in 96-wells plates (as detailed in Gaillard et al., 2001, supra, which is included as a reference and briefly herein in "1.1 Cell Culture"). We used: 1) proteins (CRM197, BSA and holo-transferrin (TrF)) conjugated to horseradish peroxidase (HRP, a 40 kDa enzyme) in a 10:1 weight/weight ratio (FIG. 11); and 2) CRM197 conjugated to HRP in a 10:1 weight/weight ratio and CRM197 conjugated to HRP in a 10:1 weight/weight ratio preincubated (1 hour at room temperature) with 10 microgram/ml soluble HB-EGF, acting as a non-competitive antagonist for DTR-mediated uptake by binding to the receptor-binding domain of CRM197 (FIG. 12); and 3) HRP-loaded CRM197-coated PEG-liposomes, at 37° C. and 4° C., to determine the active uptake (FIG. 14). For the 4° C. arm of the experiment, BCEC were allowed to cool down in the refrigerator for 1 hour before the uptake experiment was started. In this specific experiment, BCEC were grown in complete hepes buffered DMEM+S for the last 2 days; and 4) HRP-loaded CRM197-coated PEG-liposomes and HRP-loaded BSA-coated PEG-liposomes, to determine the specific uptake (FIG. 15); and 5) HRP-loaded CRM197-coated PEG-liposomes and HRP-loaded CRM197-coated PEG-liposomes on BCEC that were pretreated for 1 hour with 50 microgram/ml of free CRM197, acting as a competitive antagonist at the DTR by binding to the receptor-binding domain for the CRM197-coated PEG-liposomes (FIG. 16).

Proteins were conjugated to HRP by means of a HRP conjugation kit according to the manufacturers instructions (a Diagnostic International, San Antonio, Tex., USA). In addition, conjugated proteins were further purified on a HiPrep 16/60 column packed with Sephacryl S-200 HR matrix (Amersham Biosciences, UK).

Liposomes (100 nm) were prepared essentially according to Mastrobattista et al. (1999, Biochim. Biophys. Acta. 1419: 353-63) and consisted of EPC-35 and cholesterol in a 2:1 ratio, with 2.5% PEG2000-DSPE and 2.5% PEG2000-maleimide-PE, conjugated to about 3-60 CRM197 proteins per liposome. Briefly, after evaporation of organic solvents the lipid film was resuspended in HBS pH 6.5 containing 0.3 mg HRP per µmol PL and liposomes were extruded 3-5 times through a series of filters (200-50 nm). CRM197 was modified with a thiol group using SATA according to Bloemen et al. (1995, FEBS Lett. 357:140-4). CRM197 and SATA (1:8 molar ratio) were incubated for 1 h at room temperature under constant shaking. Free SATA was removed by centrifugation over 30 kDa cut-off filters (Vivaspin). Directly before coupling to PEG2000-maleimide-PE, the thiol group was activated (deprotected) by incubation with 0.1 M hydroxylamine (pH 7.4) for 45 min at room temperature. The amount and stability of the thiol groups was determined with Ellman's reagent (Ellman, 1959, Arch. Biochem. Biophys. 82:70-7). HRP-preloaded liposomes were coated with CRM197-conjugated PEG2000 according to the post-insertion method (Iden et al., 2001, Biochim Biophys Acta. 1513:207-16). Briefly, micelles of 2.5% CRM197-conjugated PEG2000-maleimide-PE and 2.5% PEG2000-DSPE were transferred into preformed HRP-loaded liposomes during a 2 h incubation at 40° C., before separation on a Sephadex CL4B column, followed by concentration using ultracentrifugation (60.000 g, 30 min, 10° C.). For specific experiments (as indicated for each example), CRM197 was replaced by BSA undergoing the herein above described protocol, serving as control liposomes. After preparation the phospholipid content was determined according to Fiske and Subarrow, and the protein content was determined with the Biorad protein assay (modification of Bradford). The CRM197-coated PEG-liposomes contained 3.3 proteins per liposome, where the BSA-coated PEG-liposomes contained 26.9 proteins per liposome. Furthermore size (112 nm for the CRM197-coated PEG-liposomes and 104 nm for the BSA-coated PEG-liposomes) and polydispersity (0.21 for the CRM197-coated PEG-liposomes and 0.08 for the BSA-coated PEG-liposomes) were determined by dynamic light scattering with a Malvern 4700 system (Malvern Ltd. Malvern, UK). The zeta potential (−18.6±0.7 for the CRM197-coated PEG-liposomes and −25.2±11.2 for the BSA-coated PEG-liposomes) was determined with a Malvern 3000 HSa Zetasizer (Malvern Ltd. Malvern, UK).

HRP activity of conjugated proteins, the HRP content of the liposomes and in cell lysate samples was detected using a standard colorimetric assay with the appropriate calibration curves. Cells and liposomes were lysed (after thorough washing of the cells with cold PBS) by 40 microliters of an aqueous solution of 0.1% Na-deoxycholate.

Figure 11:
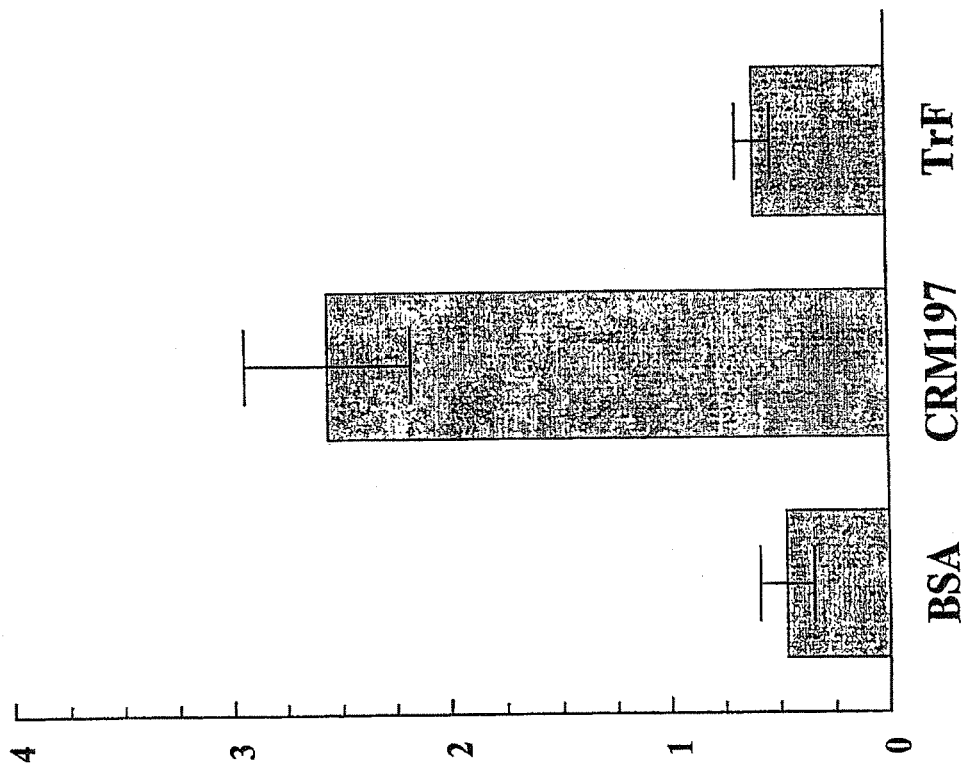
FIG. 11 is a diagram showing HRP activity in BCEC lysates after exposure to HRP-conjugated proteins (CRM197, BSA and holo-transferrin) in a concentration corresponding to 5 microgram/ml of un-conjugated HRP.

After BCEC were incubated with HRP-conjugated proteins corresponding to a concentration of 5 microgram/ml of un-conjugated HRP, the CRM197-HRP conjugate was preferably taken up by the BCEC when compared to BSA- and transferrin-HRP conjugates (FIG. 11). These results indicate that CRM197 conjugated to a cargo of 40 kDa is specifically taken up by BCEC.

Figure 12:
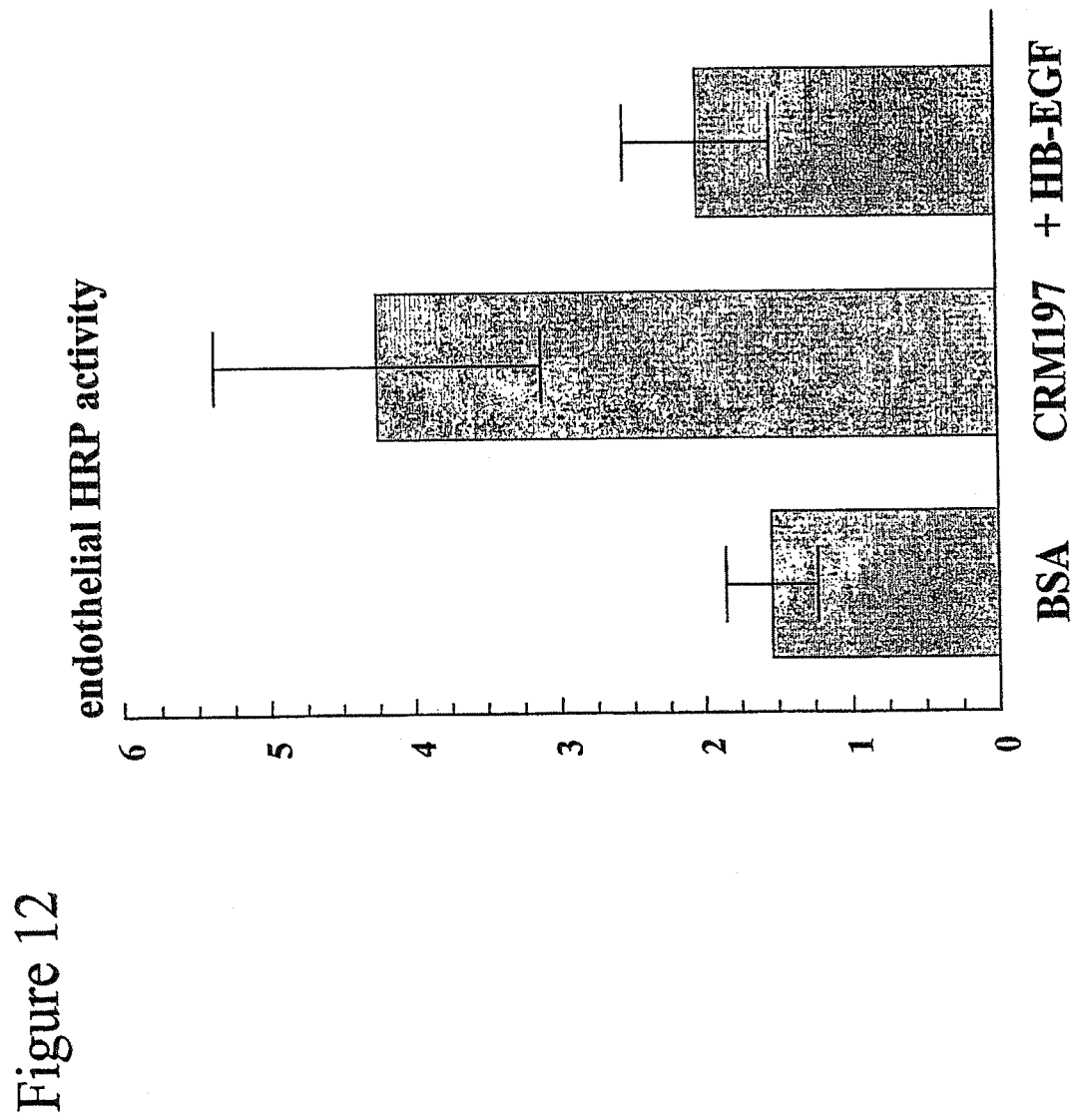
FIG. 12 is a diagram showing HRP activity in BCEC lysates after exposure, in a concentration corresponding to 5 microgram/ml of un-conjugated HRP, to HRP-conjugated CRM197, HRP-conjugated BSA and HRP-conjugated CRM197 which was preincubated with 10 microgram/ml soluble HB-EGF, acting as a non-competitive antagonist for DTR-mediated uptake by binding to the receptor-binding domain of CRM197.

After BCEC were incubated with CRM197-HRP-conjugate (corresponding to a concentration of 5 microgram/ml of un-conjugated HRP) which was preincubated with 10 microgram/ml soluble HB-EGF, the specific uptake of the CRM197-HRP conjugate was completely inhibited, as compared to the a-specific uptake of BSA-HRP-conjugate (FIG. 12). These results indicate that CRM197 conjugated to a cargo of 40 kDa is specifically taken up by BCEC via a DTR-mediated uptake process.

After BCEC were incubated with HRP-loaded CRM197-coated PEG-liposomes corresponding to a concentration of 5 microgram/ml of free HRP, the 37° C. HRP-loaded CRM197-coated PEG-liposomes were actively taken up by the BCEC when compared to the uptake at 4° C. (FIG. 14), and specifically when compared to the uptake of the HRP-loaded BSA-coated PEG-liposomes (FIG. 15), and specifically mediated by the DTR when compared to the amount of uptake of HRP-loaded CRM197-coated PEG-liposomes by BCEC that were pretreated for 1 hour with 50 microgram/ml of free CRM197 (FIG. 16). Collectively, these results indicate that CRM197-coated PEG-liposomes are actively and specifically taken up by the DTR at the BCEC.

Example 5

Drug Targeting Across the Blood-Brain Barrier via LPSS14 (DTR)

In Vitro Transcytosis Studies

Figure 13:
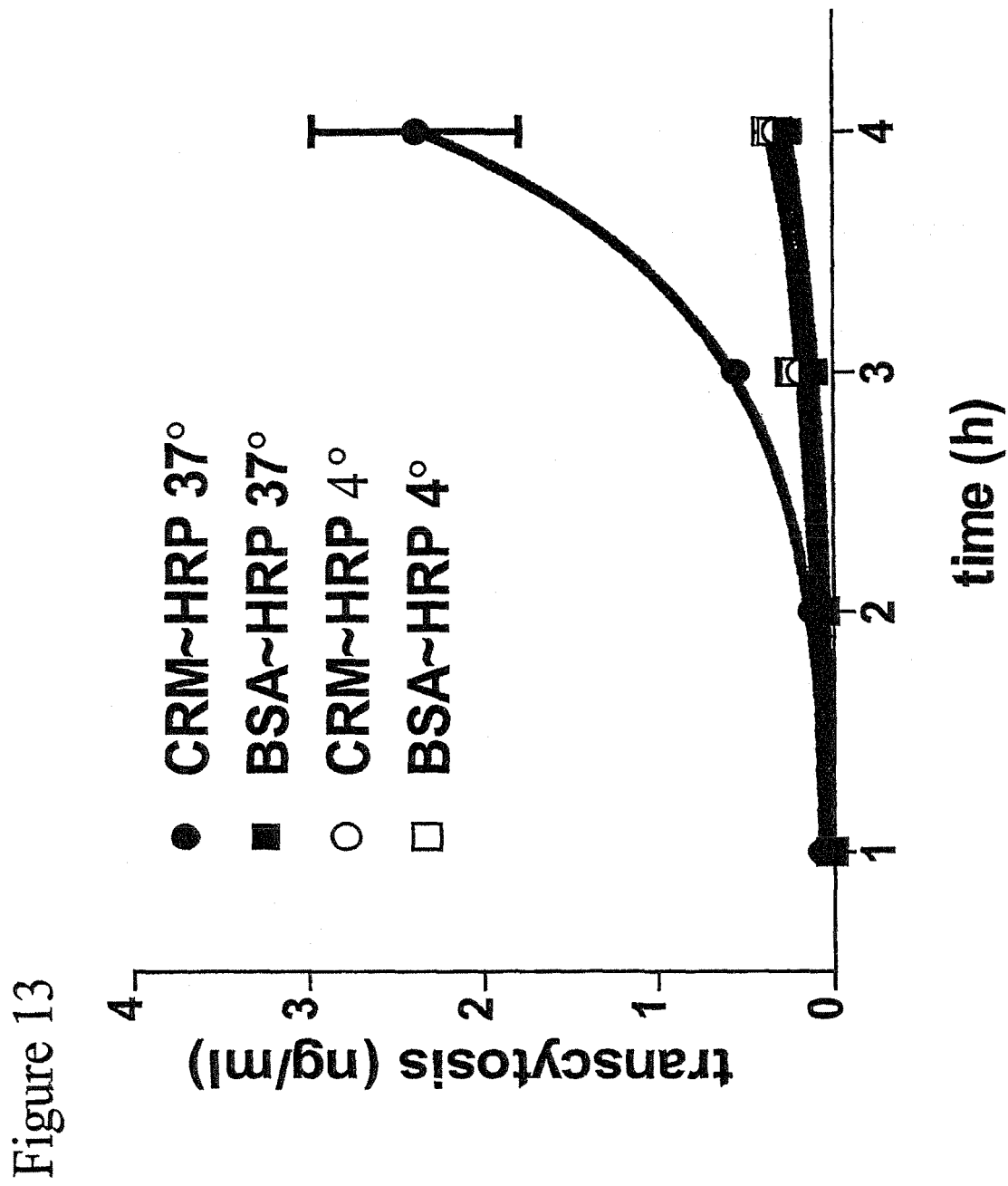
FIG. 13 is a diagram showing active and selective transcytosis of HRP-conjugated CRM197 across the in vitro blood-brain barrier (i.e., HRP activity in the basolateral compartment after apical exposure to HRP-conjugated CRM197 (lines with circles) and HRP-conjugated BSA (lines with squares) in a concentration corresponding to 5 microgram/ml of un-conjugated HRP, at 37° C. (lines with filled symbols) and 4° C. (lines with open symbols)).
Figure 17:
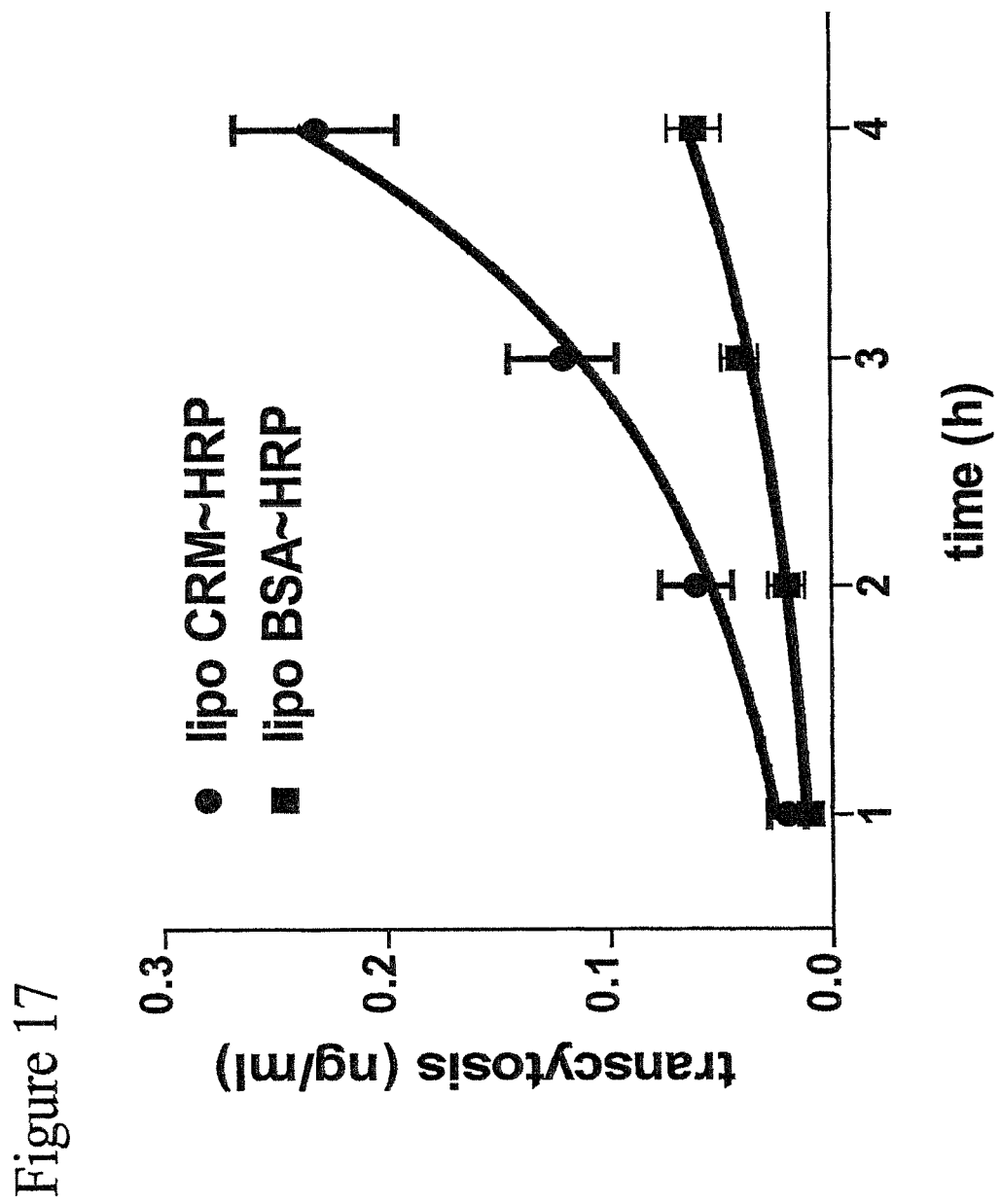
FIG. 17 is a diagram showing the selective transcytosis of HRP across the in vitro blood-brain barrier via CRM197-coated PEG-liposomes (i.e., HRP activity in the basolateral compartment after apical exposure to HRP-loaded CRM197-coated PEG-liposomes (line with circles) and HRP-loaded BSA-coated PEG-liposomes (line with squares, to determine the carrier specificity) in a concentration corresponding to 5 microgram/ml of free HRP).

For the assessment of the blood-brain barrier drug targeting ability via LPSS14 (DTR) by transcytosis, BCEC cultured from primary isolated brain capillaries from calf brain were used as monolayers on filter inserts with primary isolated newborn rat brain astrocytes cultured on the bottom side of the filter insert (FIG. 1b: BCEC-Astrocytes, as detailed in Gaillard et al., 2001, supra, which is included as a reference and briefly herein in "1.1 Cell Culture"). For the transcytosis experiments described in this example, the cells were treated with 312.5 µM 8-(4-chlorophenylthio (CPT))-cAMP, and 17.5 µM RO-20-1724 in complete hepes buffered DMEM+S for the last 2 or 3 days in order to dramatically increase tightness of (i.e., reduce paracellular leakiness) the BCEC-Astrocytes cocultures. We used: 1) CRM197, acting as the targeting moiety, and BSA, acting as an control protein, conjugated to horseradish peroxidase (HRP, a 40 kDa enzyme) in a 2:1 weight/weight ratio, both at 37° C. and at 4° C., to determine the active and specific transcytosis (FIG. 13). For the 4° C. arm of the experiment, filters were allowed to cool down in the refrigerator for 1 hour before the transport experiment was started; and 2) HRP-loaded CRM197-coated PEG-liposomes and HRP-loaded BSA-coated PEG-liposomes, to determine the specific transcytosis (FIG. 17).

BBB functionality was assessed by TEER across the filters using an electrical resistance system (ERS) with a current-passing and voltage-measuring electrode (Millicell-ERS, Millipore Corporation, Bedford, Mass., USA). TEER (Ohm·cm$^2$) was calculated from the displayed electrical resistance on the readout screen by subtraction of the electrical resistance of a collagen coated filter without cells and a correction for filter surface area. TEER across collagen coated filters with only astrocytes on the bottom was close to zero (Gaillard et al., 2001, supra).

Proteins were conjugated to HRP by means of a HRP conjugation kit according to the manufacturers instructions (a Diagnostic International, San Antonio, Tex., USA). In addition, conjugated proteins were further purified on a HiPrep 16/60 column packed with Sephacryl S-200 HR matrix (Amersham Biosciences, UK).

Liposomes (100 nm) were prepared as described above. HRP conjugated to CRM197 or BSA, or HRP-loaded PEG-liposomes conjugated to either CRM197 or BSA, were added to the apical side of the filter insert and the filter was directly transferred into a fresh well containing warm (or cold for the HRP-conjugated proteins) 250 microliter hepes buffered DMEM+S. Every hour, up to 4 hours in total, this procedure was repeated in order to prevent possible re-endocytosis of HRP-conjugated proteins or HRP-loaded PEG-liposomes conjugated to either CRM197 or BSA by the abluminal side of the BCEC. Cumulated HRP activity of transcytosed HRP into the basolateral compartment was detected using a standard colorimetric assay with the appropriate calibration curves.

The average TEER across BCEC-Astrocytes cocultures increased from 149.8±5.4 Ohm·cm$^2$ (mean±standard error, n=18) to 834±77 Ohm·cm$^2$ (mean±standard error, n=24) after treatment with 8-4-CPT-cAMP and RO-20-1724. No difference in DT sensitivity was observed between cells un-treated and cell treated as such (data not shown).

After BCEC were incubated with HRP-conjugated proteins corresponding to a concentration of 5 microgram/ml of un-conjugated HRP, the CRM197-HRP conjugate was preferably transcytosed across the BCEC when compared to BSA-HRP conjugates (FIG. 13). At 4° C., the level of transport for the CRM197-HRP conjugate was identical to the BSA-HRP conjugates at 37° and 4° C. (FIG. 13). These results indicate that CRM197, even when conjugated to a protein cargo of 40 kDa, is specifically and actively transcytosed across the blood-brain barrier.

After BCEC were incubated with HRP-loaded PEG-liposomes conjugated to either CRM197 or BSA corresponding to a concentration of 5 microgram/ml of free HRP, the CRM197-coated PEG-liposomes were preferably transcytosed across the BCEC when compared to the BSA-coated PEG-liposomes (FIG. 17). These results indicate that CRM197, even when conjugated to a liposome of about 100 nm, can specifically deliver its protein cargo of 40 kDa across the blood-brain barrier.

Example 6

Drug Targeting Across the Blood-Brain Barrier via LPSS14 (DTR)

In Vivo Brain Distribution Studies in Guinea Pigs

Brain uptake of CRM197 or holo-transferrin (TrF) conjugated to HRP (2:1 weight/weight ratio) was determined 1.5 h after an intracarotid bolus injection of the conjugates (corresponding to a concentration of 500 microgram/ml in 0.5 ml saline of un-conjugated HRP), and compared to an equal concentration of free HRP, in young male Guinea pigs (Dunkin-Hartley HsdPoc:HD, 250-300 g). The proteins were conjugated to HRP by means of a HRP conjugation kit according to the manufacturers instructions (α Diagnostic International, San Antonio, Tex., USA). In addition, conjugated proteins were further purified on a HiPrep 16/60 column packed with Sephacryl S-200 HR matrix (Amersham Biosciences, UK). Briefly, the animals were anesthetized with isoflurane inhalation (4% induction, 1-1.5% maintenance) in an air/oxygen mixture (2:1). A cannula was placed in the carotid artery for blood sample collection and drug administration. At 1.5 h after injection of the proteins, animals were deeply anesthetized with 4% isoflurane (1-2 min) and subsequently the whole animal (including the brain) was perfused with saline via the cardiac aorta (<5 min), to clear the blood vessels from blood. Directly after, the animal was decapitated and the brain was removed from the skull for further analysis. Only brains that were cleared from all blood (based on a visual inspection of the brain) were used for further analysis.

The cortex of perfused brains (and one non-perfused control brain) was dissected and weighted. Directly after, the cortex fragments were homogenized and one half volume of the homogenate was filtrated through an 120 micrometer nylon mesh. Both the filtrate (containing the vascular structures) and the eluent (containing the brain parenchymal cells), in addition to the full homogenate, were used to analyze the HRP activity of transcytosed HRP into the three brain cortex samples (i.e., full homogenates (designated "homogenate" in FIG. 18), brain parenchyma (designated "parenchyma" in FIG. 18) and cerebrovasculature (designated "capillaries" in FIG. 18)). Tissue/cells were lysed by an aqueous solution of 0.1% Na-deoxycholate (final concentration) before the HRP activity was detected in the clear supernatant of the spun-down homogenates using a standard colorimetric assay with the appropriate calibration curves and corrections for dilutions and protein content of the supernatants.

Central cross-sections (ear to ear) of about 0.5 cm of the perfused brains (and one non-perfused control brain (i.e., no injections of HRP or HRP-conjugates)) were dissected and were directly snap-frozen in isopentane and stored till use at minus 80° C. The tissue sections were cut into 14 micrometer cryosections on a cryostat. Some sections were air fixed and HRP (or endogenous peroxidases in case of the non-perfused control brain) activity was stained directly by TMB (peroxidase substrate kit TMB, Vector Laboratories) for 30 min, washed in demi water for 5 min, and dehydrated in a series of ethanol and xylene (90% ethanol 2×1 min; 100% ethanol 2×1 min; xylene 2×1 min) and finally embedded in Entellan (Merck). Other sections were fixed in 4% paraformaldehyde (15 min), and CRM197 distribution in the brain was stained by immunohistochemistry for diphtheria toxin by mouse-anti-diphtheria toxin 1:10 (OBT0746, ImmunologicalsDirect.com), and a secondary HRP-goat-anti-mouse antibody 1:250 (Jackson Immunoresearch). This primary antibody was able to selectively stain CRM197 as well as CRM197-HRP conjugates in dot-blot pilot experiments, both on pure proteins samples and in the CRM197-HRP conjugated homogenate samples (data not shown). Endogenous peroxidases were blocked (20 min in PBS with 0.3% $H_2O_2$ en 0.1% $NaN_3$), and non-specific staining was prevented by 5% normal goat serum. HRP activity of the secondary antibody was stained by TMB (peroxidase substrate kit TMB, Vector Laboratories) for 10 min, washed in demi water for 5 min, and dehydrated in a series of ethanol and xylene (90% ethanol 2×1 min; 100% ethanol 2×1 min; xylene 2×1 min) and finally embedded in Entellan (Merck). No counterstaining was performed.

Figure 18:
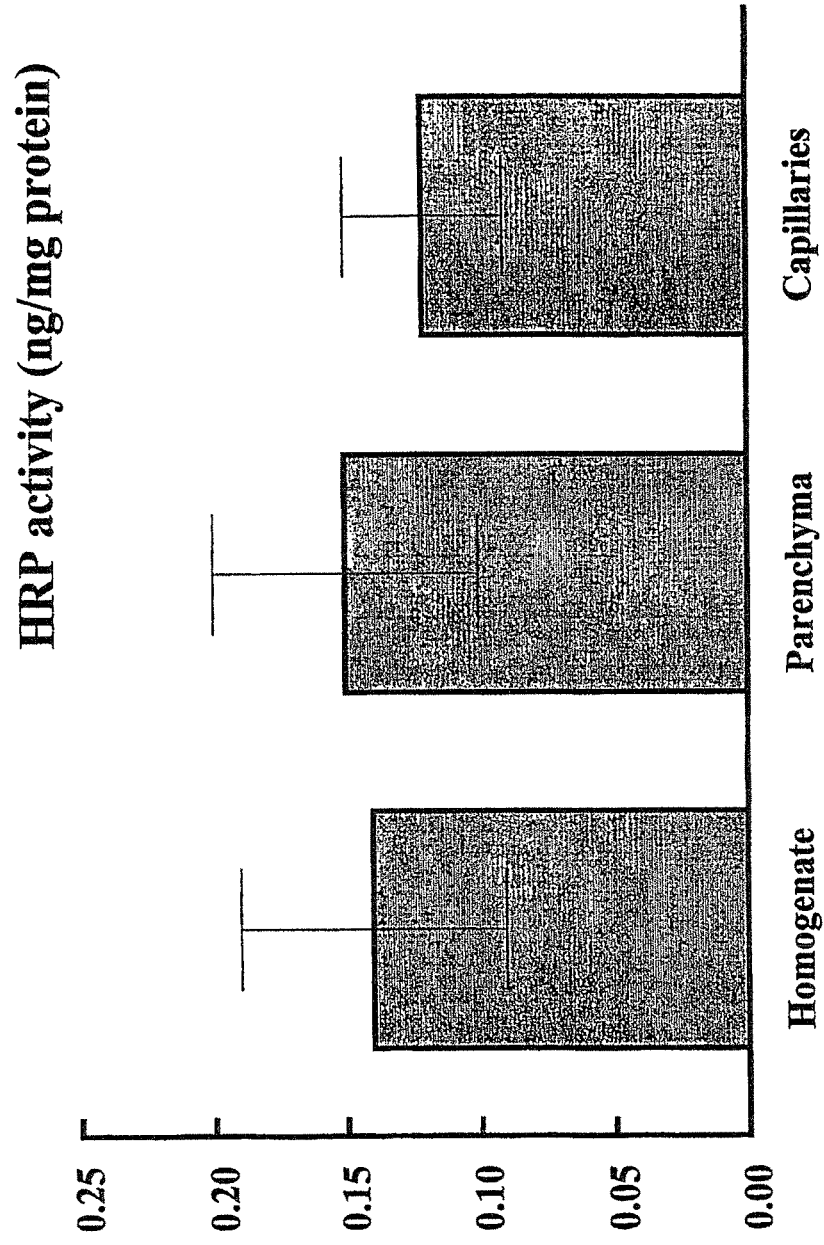
FIG. 18 is a diagram showing HRP activity in three brain cortex homogenate samples (i.e., full homogenates (designated "homogenate"), brain parenchyma (designated "parenchyma") and cerebrovasculature (designated "capillaries")) for the CRM197-HRP conjugate injected animals. The level of HRP activity in all samples from the TrF-HRP conjugate injected animals, as well as for the free HRP injected animals, were below the detection limit of the HRP assay, indicating that only CRM197 conjugated to a cargo of 40 kDa (i.e., HRP) is specifically taken up in the brain cortex, where free HRP and HRP conjugated to TrF is not.

1.5 hours after guinea pigs were injected with HRP-conjugated CRM197 and TrF (both corresponding to a concentration of 500 microgram/ml of un-conjugated HRP), as well as with an equal concentration of free HRP, only HRP activity in all three brain cortex homogenate samples (i.e., full homogenates (designated "homogenate" in FIG. 18), brain parenchyma (designated "parenchyma" in FIG. 18) and cerebrovasculature (designated "capillaries" in FIG. 18)) for the CRM197-HRP conjugate injected animals was observed (FIG. 18). Data from three animals were included for this analysis, based on the absolute absence of blood in the brain (which was also confirmed in the cryosections as described below). The level of HRP activity in all samples from the TrF-HRP conjugate injected animals, as well as for the free HRP injected animals, were below the detection limit (n=2 for both groups, after selection based on the absolute absence of blood in the brain (which was also confirmed in the cryosections as described below)). These results indicate that CRM197 conjugated to a cargo of 40 kDa (i.e., HRP) is specifically taken up in the brain cortex, where free HRP and HRP conjugated to TrF is not. Unfortunately, plasma kinetics of the injected HRP-conjugates and free HRP could not be determined based on the standard colorimetric assay for HRP due to high levels of endogenous peroxidases present in the blood that also changed over time in control (i.e., 0.5 milliliter saline) injected animals (probably due to mild and transient hemolysis due to the injected volume of saline which was observed in all animals). Consequently, the volume of brain cortex distribution for the CRM197-HRP conjugate could not be calculated.

Figure 19:
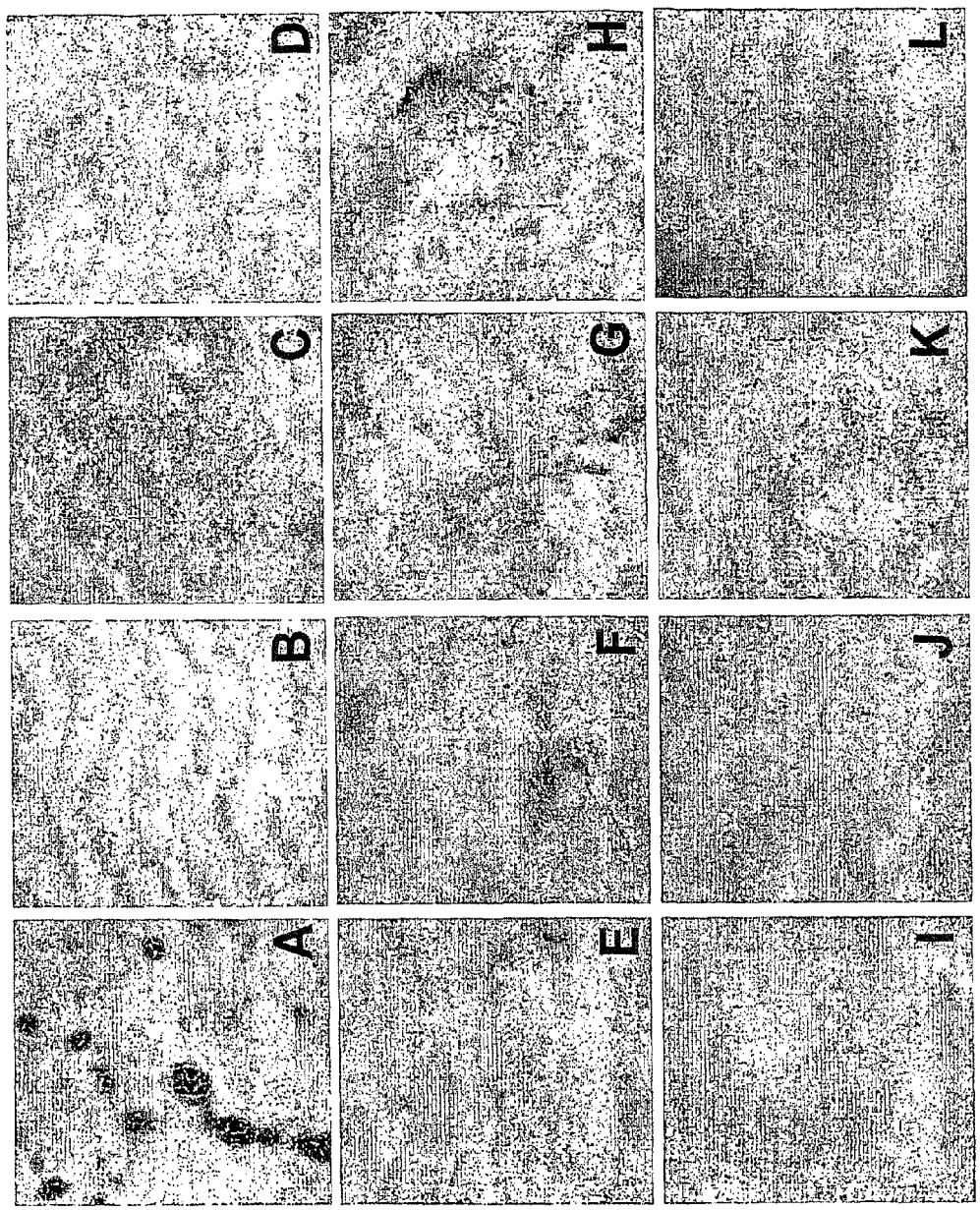
FIG. 19 displays representative photographs of: (panel A) a non-perfused control brain that was directly stained for endogenous peroxidase activity by TMB (note the distinct and strong staining pattern characteristic for blood vessels throughout the whole section); (panel B) a well-perfused control brain that was directly stained for endogenous peroxidase activity by TMB (note that the perfusion procedure with saline via the cardiac aorta was able to completely remove the endogenous peroxidase activity seen in panel A); (panels C and D) TMB-stained cryosections of well-perfused brains of two free HRP injected animals (note that, like in the well-perfused control brain, no visible staining can be observed) (panels E and F) two TMB-stained cryosections of a well-perfused brain of a CRM197-HRP conjugate injected animal (note the staining patterns characteristic for association with small blood vessels, as well as the distinct staining areas characteristic for extravasated (i.e., transported) HRP across the blood vessels); (panels G and H) TMB-stained cryosections of two more well-perfused brains of CRM197-HRP conjugate injected animals (again note the distinct staining areas characteristic for extravasated (i.e., transported) HRP across the blood vessels); (panels I and J) two TMB-stained cryosections of a well-perfused brain of a TrF-HRP conjugate injected animal (note the few (if any) very faint staining patterns characteristic for association with small blood vessels); (panels K and L) two TMB-stained cryosections of another well-perfused brain of a TrF-HRP conjugate injected animal (again note the few (if any) very faint staining patterns characteristic for association with small blood vessels). Collectively, these results indicate that CRM197 conjugated to a cargo of 40 kDa (i.e., HRP) is specifically taken up in the brain cortex, where free HRP and HRP conjugated to TrF is not. All magnifications of the brain cortex cryosections are 40×.

After the cryosections of the non-perfused control brain was directly stained for endogenous peroxidase activity by TMB a distinct and strong staining pattern characteristic for blood vessels was observed throughout the whole section. A typical example for this pattern is shown in FIG. 19, panel A. As can be appreciated from panel B in FIG. 19, the perfusion procedure with saline via the cardiac aorta was able to completely remove this endogenous peroxidase activity. These results indicate that, indeed, interfering endogenous peroxidases are present in blood, as was already observed with the standard colorimetric assay for HRP in the plasma samples. The TMB-stained cryosections of the well-perfused brains of free HRP injected animals showed, like the well-perfused control brain, no visible staining (FIG. 19, panels C and D show representative photographs of two different animals). The TMB-stained cryosections of the well-perfused brains of CRM197-HRP conjugate injected animals showed, however, staining patterns characteristic for association with small blood vessels (FIG. 19, panels E and F show representative photographs (E and F are from the same animal)). In addition, several distinct staining areas throughout the whole section characteristic for extravasated (i.e., transported) HRP across the blood vessels were observed in these animals (FIG. 19, panels F, G and H show representative photographs of three different animals). In contrast, the TMB-stained cryosections of the well-perfused brains of TrF-HRP conjugate injected animals showed a few (if any) very faint staining patterns characteristic for association with small blood vessels (FIG. 19, panels I and J, and K and L show two representative photographs of two different animals). Collectively, these results are consistent with the data obtained from the brain cortex homogenates and once more indicate that CRM197 conjugated to a cargo of 40 kDa (i.e., HRP) is specifically taken up in the brain cortex, where free HRP and HRP conjugated to TrF is not.

Figure 20:
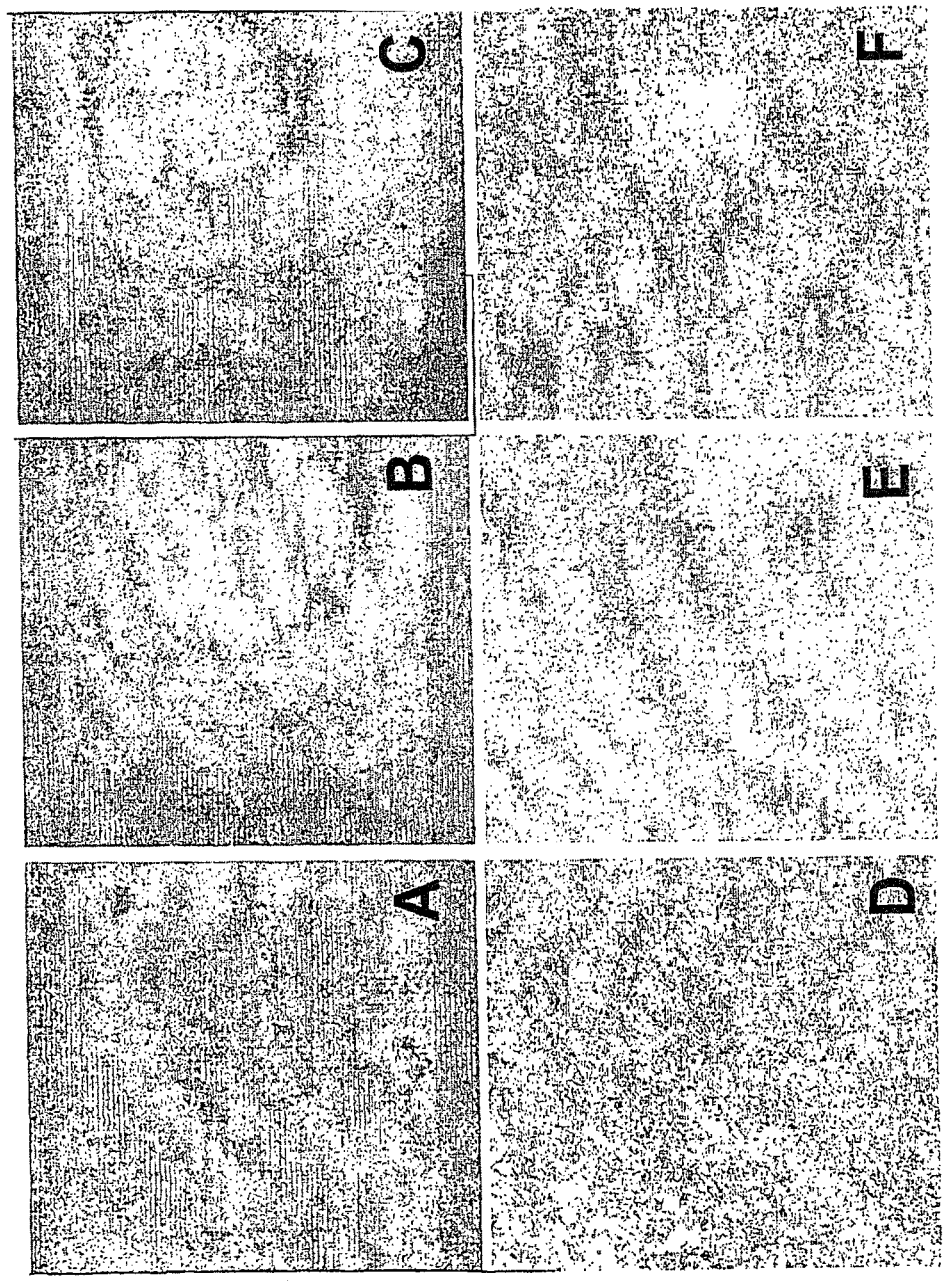
FIG. 20 displays representative photographs of: (panels A and D) a cryosection of a CRM197-HRP conjugate injected animal stained for CRM197 by immunohistochemistry for diphtheria toxin by mouse-anti-diphtheria toxin (note the faint homogeneously distributed staining pattern throughout the whole section, panel A: magnification 20× and panel D: magnification 100×); (panels B and E) a cryosection of a free HRP injected animal stained for CRM197 by immunohistochemistry for diphtheria toxin by mouse-anti-diphtheria toxin (note that the staining pattern was absent, panel B: magnification 20× and panel E: magnification 100×); (panels C and F) a cryosection of a TrF-HRP conjugate injected animal stained for CRM197 by immunohistochemistry for diphtheria toxin by mouse-anti-diphtheria toxin (again, note that the staining pattern was absent, panel C: magnification 20× and panel F: magnification 100×) Collectively, these results indicate that CRM197 (cleaved or still conjugated to HRP) is taken up in the brain.

Cryosections in which the CRM197 distribution in the brain was stained by immunohistochemistry for diphtheria toxin by mouse-anti-diphtheria toxin showed a faint homogeneously distributed pattern throughout the whole section (FIG. 20, panels A and D show two magnifications of representative photographs from the same animal). This staining pattern was not observed in the free HRP and TrF-HRP conjugate injected animals (FIG. 20, panels B and E, and C and F show two magnifications of representative photographs from the same animal, respectively). Collectively, these results indicate that CRM197 (cleaved or still conjugated to HRP) is taken up in the brain.

When all exemplary methods are considered and combined with the available prior art regarding the DTR as is included herein, the following mechanism of action for the delivery of drugs into and across the blood-brain bather is proposed: Following specific binding of the B domain of the drug- or liposome-conjugated carrier protein (e.g., CRM197) to the diphtheria toxin receptor, the carrier protein/drug complex is endocytosed. Due to a pH shift-induced change in conformation in the carrier protein, the T domain of the carrier protein/drug complex is inserted into the membrane of the endosome, followed by subsequent translocation of the A domain (including the drug complex) into the cytosol. Thereafter, drug and carrier protein (cleaved of still conjugated) are transported across the blood-brain barrier. Since a part of the endosomes are likely to end up in lysosomes this mechanism of action is also useful as a means of delivering therapeutic agents to the lysosome. In this instance, conjugates with enzymes (e.g., an enzyme deficient in a patient with a lysosomal storage disease) are particularly of interest.

What is claimed is:

1. A method of delivering a therapeutic agent into and across an endothelial cell (EC) of a microvascular blood-central nervous system (CNS) barrier in a Diphtheria toxin (DT) sensitive subject in need thereof, comprising:
   (a) administering to the subject a moiety that increases binding of DT to DT receptors (DTR) selected from the group consisting of heparin, heparan sulfate, a heparan sulfate proteoglycan, a matrix metalloproteinase inhibitor, BB-94 (batimastat), an inhibitor of ADAM12 or ADAM10, or a MAP/ERK kinase inhibitor; followed by
   (b) administering to said subject a therapeutic agent with a pharmaceutically acceptable carrier, which therapeutic agent or carrier is conjugated to a DTR-binding targeting antibody molecule to constitute a conjugate that specifically binds to the DTR on target tissue cells, such that an effective barrier-entering, barrier-crossing amount of said therapeutic agent enters and crosses the EC microvascular barrier.

2. The method of claim 1 wherein the barrier being entered and/or crossed is the blood-brain barrier (BBB), blood-retina barrier, blood-nerve barrier or blood-spinal cord barrier in a subject with (i) a CNS disease or disorder or (ii) a peripheral disease or disorder with CNS involvement.

3. The method of claim 2 wherein the disease or disorder-is:
   (a) a neurodegenerative disorder;
   (b) a neuropsychiatric disorder;
   (c) a CNS disorder selected from the group consisting of a brain tumor, epilepsy, migraine, narcolepsy, insomnia, chronic fatigue syndrome, mountain sickness, encephalitis, meningitis, and AIDS-related dementia;
   (d) an angiogenesis-related disorder;
   (e) an inflammatory or autoimmune disorder;
   (f) age-related macular degeneration; or
   (g) a lysosomal storage disease.

4. The method according to claim 1 wherein the DT-sensitive subject is a human.

5. The method of claim 1 wherein the therapeutic agent or carrier is directly conjugated to the targeting antibody molecule by:
   (a) non-specific or specific protein-protein interaction;
   (b) covalent bonding;
   (c) non-covalent bonding; or
   (d) coordinating chemical bonding;
which conjugation is optionally effected via a spacer or linker that bridges between the therapeutic agent or carrier and the targeting antibody molecule.

6. The method of claim 5 wherein the therapeutic agent-targeting antibody molecule conjugate or carrier-targeting antibody molecule conjugate is a recombinant fusion or hybrid polypeptide.

7. The method of claim 1 wherein the amino acid sequence of the DTR is at least 90% identical with SEQ ID NO:22.

8. The method of claim 1 wherein said administering is
   (a) by continuous intravenous or intraarterial infusion; or
   (b) by bolus injection by an intravenous, intramuscular, intraarterial, or intralesional route.

9. A method of delivering a therapeutic agent into and across an EC of a microvascular blood-CNS barrier in a subject, comprising administering to a DT-sensitive subject with (i) a CNS disease or disorder or (ii) a peripheral disease or disorder with CNS involvement, a composition comprising:
   (a) a therapeutic agent; and
   (b) a pharmaceutically acceptable carrier,
wherein the therapeutic agent is encapsulated in a nanocontainer to which is linked a DTR-binding targeting antibody molecule,
   wherein an effective barrier-entering and barrier crossing amount of said therapeutic agent enters and crosses the EC microvascular blood CNS barrier.

10. The method of claim 9 wherein the nanocontainer is a nanoparticle, a liposome or a nanogel.

* * * * *

SEQUENCE LISTING

<160> NUMBER OF SEQ ID NOS: 33

<210> SEQ ID NO 1
<211> LENGTH: 491
<212> TYPE: PRT
<213> ORGANISM: Homo sapiens

<400> SEQUENCE: 1

Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

```
Val Tyr Ser Tyr Phe Glu Cys Arg Glu Lys Lys Thr Glu Asn Ser Lys
            35                  40                  45
Leu Arg Lys Val Lys Tyr Glu Glu Thr Val Phe Tyr Gly Leu Gln Tyr
 50                  55                  60
Ile Leu Asn Lys Tyr Leu Lys Gly Lys Val Val Thr Lys Glu Lys Ile
 65                  70                  75                  80
Gln Glu Ala Lys Asp Val Tyr Lys Glu His Phe Gln Asp Asp Val Phe
                 85                  90                  95
Asn Glu Lys Gly Trp Asn Tyr Ile Leu Glu Lys Tyr Asp Gly His Leu
                100                 105                 110
Pro Ile Glu Ile Lys Ala Val Pro Glu Gly Phe Val Ile Pro Arg Gly
                115                 120                 125
Asn Val Leu Phe Thr Val Glu Asn Thr Asp Pro Glu Cys Tyr Trp Leu
                130                 135                 140
Thr Asn Trp Ile Glu Thr Ile Leu Val Gln Ser Trp Tyr Pro Ile Thr
145                 150                 155                 160
Val Ala Thr Asn Ser Arg Glu Gln Lys Lys Ile Leu Ala Lys Tyr Leu
                165                 170                 175
Leu Glu Thr Ser Gly Asn Leu Asp Gly Leu Glu Tyr Lys Leu His Asp
                180                 185                 190
Phe Gly Tyr Arg Gly Val Ser Ser Gln Glu Thr Ala Gly Ile Gly Ala
                195                 200                 205
Ser Ala His Leu Val Asn Phe Lys Gly Thr Asp Thr Val Ala Gly Leu
                210                 215                 220
Ala Leu Ile Lys Lys Tyr Tyr Gly Thr Lys Asp Pro Val Pro Gly Tyr
225                 230                 235                 240
Ser Val Pro Ala Ala Glu His Ser Thr Ile Thr Ala Trp Gly Lys Asp
                245                 250                 255
His Glu Lys Asp Ala Phe Glu His Ile Val Thr Gln Phe Ser Ser Val
                260                 265                 270
Pro Val Ser Val Val Ser Asp Ser Tyr Asp Ile Tyr Asn Ala Cys Glu
                275                 280                 285
Lys Ile Trp Gly Glu Asp Leu Arg His Leu Ile Val Ser Arg Ser Thr
                290                 295                 300
Gln Ala Pro Leu Ile Ile Arg Pro Asp Ser Gly Asn Pro Leu Asp Thr
305                 310                 315                 320
Val Leu Lys Val Leu Glu Ile Leu Gly Lys Lys Phe Pro Val Thr Glu
                325                 330                 335
Asn Ser Lys Gly Tyr Lys Leu Leu Pro Pro Tyr Leu Arg Val Ile Gln
                340                 345                 350
Gly Asp Gly Val Asp Ile Asn Thr Leu Gln Glu Ile Val Glu Gly Met
                355                 360                 365
Lys Gln Lys Met Trp Ser Ile Glu Asn Ile Ala Phe Gly Ser Gly Gly
                370                 375                 380
Gly Leu Leu Gln Lys Leu Thr Arg Asp Leu Leu Asn Cys Ser Phe Lys
385                 390                 395                 400
Cys Ser Tyr Val Val Thr Asn Gly Leu Gly Ile Asn Val Phe Lys Asp
                405                 410                 415
Pro Val Ala Asp Pro Asn Lys Arg Ser Lys Gly Arg Leu Ser Leu
                420                 425                 430
His Arg Thr Pro Ala Gly Asn Phe Val Thr Leu Glu Glu Gly Lys Gly
                435                 440                 445
Asp Leu Glu Glu Tyr Gly Gln Asp Leu Leu His Thr Val Phe Lys Asn
```

```
                    450                 455                 460
Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490
```

<210> SEQ ID NO 2
<211> LENGTH: 408
<212> TYPE: PRT
<213> ORGANISM: Homo sapiens

<400> SEQUENCE: 2

```
Met Ile Pro Gly Asn Arg Met Leu Met Val Leu Leu Cys Gln Val
1               5                   10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
                35                  40                  45

Gln Ser His Glu Leu Leu Arg Asp Phe Glu Ala Thr Leu Leu Gln Met
50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu
                85                  90                  95

Glu Gln Ile His Ser Thr Gly Leu Glu Tyr Pro Glu Arg Pro Ala Ser
                100                 105                 110

Arg Ala Asn Thr Val Arg Ser Phe His His Glu Glu His Leu Glu Asn
                115                 120                 125

Ile Pro Gly Thr Ser Glu Asn Ser Ala Phe Arg Phe Leu Phe Asn Leu
                130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
                180                 185                 190

Gly His Leu Ile Thr Arg Leu Leu Asp Thr Arg Leu Val His His Asn
                195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
                260                 265                 270

Val Thr Phe Gly His Asp Gly Arg Gly His Ala Leu Thr Arg Arg Arg
                275                 280                 285

Arg Ala Lys Arg Ser Pro Lys His His Ser Gln Arg Ala Arg Lys Lys
                290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
```

```
                    340                 345                 350
Asn His Ala Ile Val Gln Thr Leu Val Asn Ser Val Asn Ser Ser Ile
                355                 360                 365

Pro Lys Ala Cys Cys Val Pro Thr Glu Leu Ser Ala Ile Ser Met Leu
        370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 3
<211> LENGTH: 408
<212> TYPE: PRT
<213> ORGANISM: Homo sapiens

<400> SEQUENCE: 3

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
```

```
                    305                 310                 315                 320
Gly Trp Asn Asp Trp Ile Val Ala Pro Pro Gly Tyr Gln Ala Phe Tyr
                    325                 330                 335

Cys His Gly Asp Cys Pro Phe Pro Leu Ala Asp His Leu Asn Ser Thr
                    340                 345                 350

Asn His Ala Ile Val Gln Thr Leu Val Asn Ser Val Asn Ser Ser Ile
                    355                 360                 365

Pro Lys Ala Cys Cys Val Pro Thr Glu Leu Ser Ala Ile Ser Met Leu
                    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                    405

<210> SEQ ID NO 4
<211> LENGTH: 408
<212> TYPE: PRT
<213> ORGANISM: Homo sapiens

<400> SEQUENCE: 4

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
                    20                  25                  30

Lys Lys Val Ala Glu Ile Gln Gly His Ala Gly Gly Arg Arg Ser Gly
                    35                  40                  45

Gln Ser His Glu Leu Leu Arg Asp Phe Glu Ala Thr Leu Leu Gln Met
            50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                    85                  90                  95

Glu Gln Ile His Ser Thr Gly Leu Glu Tyr Pro Glu Arg Pro Ala Ser
                    100                 105                 110

Arg Ala Asn Thr Val Arg Ser Phe His His Glu Glu His Leu Glu Asn
                    115                 120                 125

Ile Pro Gly Thr Ser Glu Asn Ser Ala Phe Arg Phe Leu Phe Asn Leu
            130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                    165                 170                 175

Arg Ile Asn Ile Tyr Glu Val Met Lys Pro Pro Ala Glu Val Val Pro
                    180                 185                 190

Gly His Leu Ile Thr Arg Leu Leu Asp Thr Arg Leu Val His His Asn
                    195                 200                 205

Val Thr Arg Trp Glu Thr Phe Asp Val Ser Pro Ala Val Leu Arg Trp
            210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                    245                 250                 255

Ser Leu Pro Gln Gly Ser Gly Asn Trp Ala Gln Leu Arg Pro Leu Leu
                    260                 265                 270

Val Thr Phe Gly His Asp Gly Arg Gly His Ala Leu Thr Arg Arg Arg
```

```
                    275                 280                 285
Arg Ala Lys Arg Ser Pro Lys His His Ser Gln Arg Ala Arg Lys Lys
            290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
            355                 360                 365

Pro Lys Ala Cys Cys Val Pro Thr Glu Leu Ser Ala Ile Ser Met Leu
        370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 5
<211> LENGTH: 948
<212> TYPE: PRT
<213> ORGANISM: Homo sapiens

<400> SEQUENCE: 5

Met Gly Ile Lys Thr Leu Asn Leu Val Leu Gly Leu Lys Arg Ala Leu
1               5                   10                  15

Glu Phe Pro Glu Val Phe Met Met Glu Val Lys Asp Pro Asn Met Lys
            20                  25                  30

Gly Ala Met Leu Thr Asn Thr Gly Lys Tyr Ala Ile Pro Thr Ile Asp
        35                  40                  45

Ala Glu Ala Tyr Ala Ile Gly Lys Lys Glu Lys Pro Pro Phe Leu Pro
    50                  55                  60

Glu Glu Pro Ser Ser Ser Glu Glu Asp Asp Pro Ile Pro Asp Glu
65                  70                  75                  80

Leu Leu Cys Leu Ile Cys Lys Asp Ile Met Thr Asp Ala Val Val Ile
                85                  90                  95

Pro Cys Cys Gly Asn Ser Tyr Cys Asp Glu Cys Ile Arg Thr Ala Leu
            100                 105                 110

Leu Glu Ser Asp Glu His Thr Cys Pro Thr Cys His Gln Asn Asp Val
        115                 120                 125

Ser Pro Asp Ala Leu Ile Ala Asn Lys Phe Leu Arg Gln Ala Val Asn
    130                 135                 140

Asn Phe Lys Asn Glu Thr Gly Tyr Thr Lys Arg Leu Arg Lys Gln Leu
145                 150                 155                 160

Pro Pro Pro Pro Pro Ile Pro Pro Arg Pro Leu Ile Gln Arg
                165                 170                 175

Asn Leu Gln Pro Leu Met Arg Ser Pro Ile Ser Arg Gln Gln Asp Pro
            180                 185                 190

Leu Met Ile Pro Val Thr Ser Ser Thr His Pro Ala Pro Ser Ile
        195                 200                 205

Ser Ser Leu Thr Ser Asn Gln Ser Ser Leu Ala Pro Val Ser Gly
    210                 215                 220

Asn Pro Ser Ser Ala Pro Ala Pro Val Pro Asp Ile Thr Ala Thr Val
225                 230                 235                 240

Ser Ile Ser Val His Ser Glu Lys Ser Asp Gly Pro Phe Arg Asp Ser
```

-continued

```
                    245                 250                 255
Asp Asn Lys Ile Leu Pro Ala Ala Leu Ala Ser Glu His Ser Lys
                260                 265                 270
Gly Thr Ser Ser Ile Ala Ile Thr Ala Leu Met Glu Glu Lys Gly Tyr
            275                 280                 285
Gln Val Pro Val Leu Gly Thr Pro Ser Leu Leu Gly Gln Ser Leu Leu
        290                 295                 300
His Gly Gln Leu Ile Pro Thr Thr Gly Pro Val Arg Ile Asn Thr Ala
305                 310                 315                 320
Arg Pro Gly Gly Gly Arg Pro Gly Trp Glu His Ser Asn Lys Leu Gly
                325                 330                 335
Tyr Leu Val Ser Pro Pro Gln Gln Ile Arg Arg Gly Glu Arg Ser Cys
            340                 345                 350
Tyr Arg Ser Ile Asn Arg Gly Arg His His Ser Glu Arg Ser Gln Arg
        355                 360                 365
Thr Gln Gly Pro Ser Leu Pro Ala Thr Pro Val Phe Val Pro Val Pro
    370                 375                 380
Pro Pro Pro Leu Tyr Pro Pro Pro His Thr Leu Pro Leu Pro Pro
385                 390                 395                 400
Gly Val Pro Pro Pro Gln Phe Ser Pro Gln Phe Pro Pro Gly Gln Pro
                405                 410                 415
Pro Pro Ala Gly Tyr Ser Val Pro Pro Gly Phe Pro Pro Ala Pro
            420                 425                 430
Ala Asn Leu Ser Thr Pro Trp Val Ser Ser Gly Val Gln Thr Ala His
        435                 440                 445
Ser Asn Thr Ile Pro Thr Thr Gln Ala Pro Pro Leu Ser Arg Glu Glu
    450                 455                 460
Phe Tyr Arg Glu Gln Arg Arg Leu Lys Glu Glu Lys Lys Lys Ser
465                 470                 475                 480
Lys Leu Asp Glu Phe Thr Asn Asp Phe Ala Lys Glu Leu Met Glu Tyr
                485                 490                 495
Lys Lys Ile Gln Lys Glu Arg Arg Ser Phe Ser Arg Ser Lys Ser
            500                 505                 510
Pro Tyr Ser Gly Ser Ser Tyr Ser Arg Ser Ser Tyr Thr Tyr Ser Lys
        515                 520                 525
Ser Arg Ser Gly Ser Thr Arg Ser Arg Ser Tyr Ser Arg Ser Phe Ser
    530                 535                 540
Arg Ser His Ser Arg Ser Tyr Ser Arg Ser Pro Pro Tyr Pro Arg Arg
545                 550                 555                 560
Gly Arg Gly Lys Ser Arg Asn Tyr Arg Ser Arg Ser Arg Ser His Gly
                565                 570                 575
Tyr His Arg Ser Arg Ser Arg Ser Pro Pro Tyr Arg Arg Tyr His Ser
            580                 585                 590
Arg Ser Arg Ser Pro Gln Ala Phe Arg Gly Gln Ser Pro Asn Lys Arg
        595                 600                 605
Asn Val Pro Gln Gly Glu Thr Glu Arg Glu Tyr Phe Asn Arg Tyr Arg
    610                 615                 620
Glu Val Pro Pro Pro Tyr Asp Met Lys Ala Tyr Tyr Gly Arg Ser Val
625                 630                 635                 640
Asp Phe Arg Asp Pro Phe Glu Lys Glu Arg Tyr Arg Glu Trp Glu Arg
                645                 650                 655
Lys Tyr Arg Glu Trp Tyr Glu Lys Tyr Tyr Lys Gly Tyr Ala Ala Gly
            660                 665                 670
```

```
Ala Gln Pro Arg Pro Ser Ala Asn Arg Glu Asn Phe Ser Pro Glu Arg
            675                 680                 685

Phe Leu Pro Leu Asn Ile Arg Asn Ser Pro Phe Thr Arg Gly Arg Arg
        690                 695                 700

Glu Asp Tyr Val Gly Gly Gln Ser His Arg Ser Arg Asn Ile Gly Ser
705                 710                 715                 720

Asn Tyr Pro Glu Lys Leu Ser Ala Arg Asp Gly His Asn Gln Lys Asp
                725                 730                 735

Asn Thr Lys Ser Lys Glu Lys Glu Ser Glu Asn Ala Pro Gly Asp Gly
            740                 745                 750

Lys Gly Asn Lys His Lys His Arg Lys Arg Lys Gly Glu Glu
        755                 760                 765

Ser Glu Gly Phe Leu Asn Pro Glu Leu Leu Glu Thr Ser Arg Lys Ser
770                 775                 780

Arg Glu Pro Thr Gly Val Glu Glu Asn Lys Thr Asp Ser Leu Phe Val
785                 790                 795                 800

Leu Pro Ser Arg Asp Asp Ala Thr Pro Val Arg Asp Glu Pro Met Asp
                805                 810                 815

Ala Glu Ser Ile Thr Phe Lys Ser Val Ser Glu Lys Asp Lys Arg Glu
            820                 825                 830

Arg Asp Lys Pro Lys Ala Lys Gly Asp Lys Thr Lys Arg Lys Asn Asp
        835                 840                 845

Gly Ser Ala Val Ser Lys Lys Glu Asn Ile Val Lys Pro Ala Lys Gly
850                 855                 860

Pro Gln Glu Lys Val Asp Gly Asp Val Arg Asp Leu Leu Asp Leu Asn
865                 870                 875                 880

Leu Gln Leu Lys Lys Pro Lys Arg Arg Leu Arg Arg Leu Thr Ile Leu
                885                 890                 895

Asn His His Leu Pro Leu Arg Arg Met Lys Lys Ser Leu Glu Pro Pro
            900                 905                 910

Glu Lys Leu Thr Leu Asn Gln Gln Lys Thr Pro Arg Asn Lys Thr Ser
        915                 920                 925

Gln Arg Gly Lys Ser Glu Glu Gly Leu Phe Gln Arg Cys Gln Ile Arg
930                 935                 940

Lys Ala Asn Asn
945

<210> SEQ ID NO 6
<211> LENGTH: 556
<212> TYPE: PRT
<213> ORGANISM: Homo sapiens

<400> SEQUENCE: 6

Met Ala Thr Thr Ala Thr Cys Thr Arg Phe Thr Asp Tyr Gln Leu
1               5                   10                  15

Phe Glu Glu Leu Gly Lys Gly Ala Phe Ser Val Val Arg Arg Cys Val
            20                  25                  30

Lys Lys Thr Ser Thr Gln Glu Tyr Ala Ala Lys Ile Ile Asn Thr Lys
        35                  40                  45

Lys Leu Ser Ala Arg Asp His Gln Lys Leu Glu Arg Glu Ala Arg Ile
    50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95
```

```
Glu Leu Phe Glu Asp Ile Val Ala Arg Glu Tyr Tyr Ser Glu Ala Asp
            100                 105                 110

Ala Ser His Cys Ile His Gln Ile Leu Glu Ser Val Asn His Ile His
        115                 120                 125

Gln His Asp Ile Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala Asp Gln Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Arg Lys Phe Asn Ala Arg Arg Lys Leu Lys Gly Ala Ile
    290                 295                 300

Leu Thr Thr Met Leu Val Ser Arg Asn Phe Ser Ala Ala Lys Ser Leu
305                 310                 315                 320

Leu Asn Lys Lys Ser Asp Gly Val Lys Pro Gln Ser Asn Asn Lys
                325                 330                 335

Asn Ser Leu Val Ser Pro Ala Gln Glu Pro Ala Pro Leu Gln Thr Ala
            340                 345                 350

Met Glu Pro Gln Thr Thr Val Val His Asn Ala Thr Asp Gly Ile Lys
        355                 360                 365

Gly Ser Thr Glu Ser Cys Asn Thr Thr Thr Glu Asp Glu Asp Leu Lys
    370                 375                 380

Ala Ala Pro Leu Arg Thr Gly Asn Gly Ser Ser Val Pro Glu Gly Arg
385                 390                 395                 400

Ser Ser Arg Asp Arg Thr Ala Pro Ser Ala Gly Met Gln Pro Gln Pro
                405                 410                 415

Ser Leu Cys Ser Ser Ala Met Arg Lys Gln Glu Ile Ile Lys Ile Thr
            420                 425                 430

Glu Gln Leu Ile Glu Ala Ile Asn Asn Gly Asp Phe Glu Ala Tyr Thr
        435                 440                 445

Lys Ile Cys Asp Pro Gly Leu Thr Ser Phe Glu Pro Glu Ala Leu Gly
    450                 455                 460

Asn Leu Val Glu Gly Met Asp Phe His Lys Phe Tyr Phe Glu Asn Leu
465                 470                 475                 480

Leu Ser Lys Asn Ser Lys Pro Ile His Thr Thr Ile Leu Asn Pro His
                485                 490                 495

Val His Val Ile Gly Glu Asp Ala Ala Cys Ile Ala Tyr Ile Arg Leu
            500                 505                 510

Thr Gln Tyr Ile Asp Gly Gln Gly Arg Pro Arg Thr Ser Gln Ser Glu
        515                 520                 525
```

Glu Thr Arg Val Trp His Arg Arg Asp Gly Lys Trp Leu Asn Val His
    530                 535                 540

Tyr His Cys Ser Gly Ala Pro Ala Ala Pro Leu Gln
545                 550                 555

<210> SEQ ID NO 7
<211> LENGTH: 527
<212> TYPE: PRT
<213> ORGANISM: Homo sapiens

<400> SEQUENCE: 7

Met Ala Thr Thr Ala Thr Cys Thr Arg Phe Thr Asp Asp Tyr Gln Leu
1               5                   10                  15

Phe Glu Glu Leu Gly Lys Gly Ala Phe Ser Val Val Arg Arg Cys Val
                20                  25                  30

Lys Lys Thr Ser Thr Gln Glu Tyr Ala Ala Lys Ile Ile Asn Thr Lys
            35                  40                  45

Lys Leu Ser Ala Arg Asp His Gln Lys Leu Glu Arg Glu Ala Arg Ile
        50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
                100                 105                 110

Ala Ser His Cys Ile His Gln Ile Leu Glu Ser Val Asn His Ile His
            115                 120                 125

Gln His Asp Ile Val His Arg Asp Leu Lys Pro Glu Asn Leu Leu Leu
        130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
                180                 185                 190

Lys Pro Val Asp Ile Trp Ala Cys Gly Val Ile Leu Tyr Ile Leu Leu
            195                 200                 205

Val Gly Tyr Pro Pro Phe Trp Asp Glu Asp Gln His Lys Leu Tyr Gln
        210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala Asp Gln Ala Leu Lys His Pro Trp Val
                260                 265                 270

Cys Gln Arg Ser Thr Val Ala Ser Met Met His Arg Gln Glu Thr Val
            275                 280                 285

Glu Cys Leu Arg Lys Phe Asn Ala Arg Arg Lys Leu Lys Gly Ala Ile
        290                 295                 300

Leu Thr Thr Met Leu Val Ser Arg Asn Phe Ser Val Gly Arg Gln Ser
305                 310                 315                 320

Ser Ala Pro Ala Ser Pro Ala Ala Ser Ala Ala Gly Leu Ala Gly Gln
                325                 330                 335

Ala Ala Lys Ser Leu Leu Asn Lys Lys Ser Asp Gly Gly Val Lys Lys
                340                 345                 350

```
Arg Lys Ser Ser Ser Val His Leu Met Glu Pro Gln Thr Thr Val
        355                 360                 365

Val His Asn Ala Thr Asp Gly Ile Lys Gly Ser Thr Glu Ser Cys Asn
370                 375                 380

Thr Thr Thr Glu Asp Glu Asp Leu Lys Val Arg Lys Gln Glu Ile Ile
385                 390                 395                 400

Lys Ile Thr Glu Gln Leu Ile Glu Ala Ile Asn Asn Gly Asp Phe Glu
                405                 410                 415

Ala Tyr Thr Lys Ile Cys Asp Pro Gly Leu Thr Ser Phe Glu Pro Glu
            420                 425                 430

Ala Leu Gly Asn Leu Val Glu Gly Met Asp Phe His Lys Phe Tyr Phe
        435                 440                 445

Glu Asn Leu Leu Ser Lys Asn Ser Lys Pro Ile His Thr Thr Ile Leu
    450                 455                 460

Asn Pro His Val His Val Ile Gly Glu Asp Ala Ala Cys Ile Ala Tyr
465                 470                 475                 480

Ile Arg Leu Thr Gln Tyr Ile Asp Gly Gln Gly Arg Pro Arg Thr Ser
                485                 490                 495

Gln Ser Glu Glu Thr Arg Val Trp His Arg Arg Asp Gly Lys Trp Leu
            500                 505                 510

Asn Val His Tyr His Cys Ser Gly Ala Pro Ala Pro Leu Gln
        515                 520                 525

<210> SEQ ID NO 8
<211> LENGTH: 518
<212> TYPE: PRT
<213> ORGANISM: Homo sapiens

<400> SEQUENCE: 8

Met Ala Thr Thr Ala Thr Cys Thr Arg Phe Thr Asp Asp Tyr Gln Leu
1               5                   10                  15

Phe Glu Glu Leu Gly Lys Gly Ala Phe Ser Val Val Arg Arg Cys Val
                20                  25                  30

Lys Lys Thr Ser Thr Gln Glu Tyr Ala Ala Lys Ile Ile Asn Thr Lys
            35                  40                  45

Lys Leu Ser Ala Arg Asp His Gln Lys Leu Glu Arg Glu Ala Arg Ile
        50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
            100                 105                 110

Ala Ser His Cys Ile His Gln Ile Leu Glu Ser Val Asn His Ile His
        115                 120                 125

Gln His Asp Ile Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Ile Trp Ala Cys Gly Val Ile Leu Tyr Ile Leu Leu
        195                 200                 205
```

-continued

```
Val Gly Tyr Pro Pro Phe Trp Asp Glu Asp Gln His Lys Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala Asp Gln Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Arg Lys Phe Asn Ala Arg Arg Lys Leu Lys Gly Ala Ile
    290                 295                 300

Leu Thr Thr Met Leu Val Ser Arg Asn Phe Ser Ala Ala Lys Ser Leu
305                 310                 315                 320

Leu Asn Lys Lys Ser Asp Gly Gly Val Lys Pro Gln Ser Asn Asn Lys
                325                 330                 335

Asn Ser Leu Val Ser Pro Ala Gln Glu Pro Ala Pro Leu Gln Thr Ala
            340                 345                 350

Met Glu Pro Gln Thr Thr Val His Asn Ala Thr Asp Gly Ile Lys
        355                 360                 365

Gly Ser Thr Glu Ser Cys Asn Thr Thr Thr Glu Asp Glu Asp Leu Lys
    370                 375                 380

Val Arg Lys Gln Glu Ile Ile Lys Ile Thr Glu Gln Leu Ile Glu Ala
385                 390                 395                 400

Ile Asn Asn Gly Asp Phe Glu Ala Tyr Thr Lys Ile Cys Asp Pro Gly
                405                 410                 415

Leu Thr Ser Phe Glu Pro Glu Ala Leu Gly Asn Leu Val Glu Gly Met
            420                 425                 430

Asp Phe His Lys Phe Tyr Phe Glu Asn Leu Leu Ser Lys Asn Ser Lys
        435                 440                 445

Pro Ile His Thr Thr Ile Leu Asn Pro His Val His Val Ile Gly Glu
    450                 455                 460

Asp Ala Ala Cys Ile Ala Tyr Ile Arg Leu Thr Gln Tyr Ile Asp Gly
465                 470                 475                 480

Gln Gly Arg Pro Arg Thr Ser Gln Ser Glu Glu Thr Arg Val Trp His
                485                 490                 495

Arg Arg Asp Gly Lys Trp Leu Asn Val His Tyr His Cys Ser Gly Ala
            500                 505                 510

Pro Ala Ala Pro Leu Gln
            515

<210> SEQ ID NO 9
<211> LENGTH: 495
<212> TYPE: PRT
<213> ORGANISM: Homo sapiens

<400> SEQUENCE: 9

Met Ala Thr Thr Ala Thr Cys Thr Arg Phe Thr Asp Asp Tyr Gln Leu
1               5                   10                  15

Phe Glu Glu Leu Gly Lys Gly Ala Phe Ser Val Val Arg Arg Cys Val
                20                  25                  30

Lys Lys Thr Ser Thr Gln Glu Tyr Ala Ala Lys Ile Ile Asn Thr Lys
            35                  40                  45

Lys Leu Ser Ala Arg Asp His Gln Lys Leu Glu Arg Glu Ala Arg Ile
        50                  55                  60
```

```
Cys Arg Leu Leu Lys His Pro Asn Ile Val Arg Leu His Asp Ser Ile
 65                  70                  75                  80

Ser Glu Glu Gly Phe His Tyr Leu Val Phe Asp Leu Val Thr Gly Gly
                 85                  90                  95

Glu Leu Phe Glu Asp Ile Val Ala Arg Glu Tyr Tyr Ser Glu Ala Asp
            100                 105                 110

Ala Ser His Cys Ile His Gln Ile Leu Glu Ser Val Asn His Ile His
        115                 120                 125

Gln His Asp Ile Val His Arg Asp Leu Lys Pro Glu Asn Leu Leu Leu
130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala Asp Gln Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Arg Lys Phe Asn Ala Arg Arg Lys Leu Lys Gly Ala Ile
290                 295                 300

Leu Thr Thr Met Leu Val Ser Arg Asn Phe Ser Ala Ala Lys Ser Leu
305                 310                 315                 320

Leu Asn Lys Lys Ser Asp Gly Gly Val Lys Glu Pro Gln Thr Thr Val
                325                 330                 335

Val His Asn Ala Thr Asp Gly Ile Lys Gly Ser Thr Glu Ser Cys Asn
            340                 345                 350

Thr Thr Thr Glu Asp Glu Asp Leu Lys Val Arg Lys Gln Glu Ile Ile
        355                 360                 365

Lys Ile Thr Glu Gln Leu Ile Glu Ala Ile Asn Asn Gly Asp Phe Glu
370                 375                 380

Ala Tyr Thr Lys Ile Cys Asp Pro Gly Leu Thr Ser Phe Glu Pro Glu
385                 390                 395                 400

Ala Leu Gly Asn Leu Val Glu Gly Met Asp Phe His Lys Phe Tyr Phe
                405                 410                 415

Glu Asn Leu Leu Ser Lys Asn Ser Lys Pro Ile His Thr Thr Ile Leu
            420                 425                 430

Asn Pro His Val His Val Ile Gly Glu Asp Ala Ala Cys Ile Ala Tyr
        435                 440                 445

Ile Arg Leu Thr Gln Tyr Ile Asp Gly Gln Gly Arg Pro Arg Thr Ser
450                 455                 460

Gln Ser Glu Glu Thr Arg Val Trp His Arg Arg Asp Gly Lys Trp Leu
465                 470                 475                 480

Asn Val His Tyr His Cys Ser Gly Ala Pro Ala Ala Pro Leu Gln
```

```
                485                 490                 495
```

<210> SEQ ID NO 10
<211> LENGTH: 411
<212> TYPE: PRT
<213> ORGANISM: Homo sapiens
<400> SEQUENCE: 10

```
Met Ala Thr Thr Ala Thr Cys Thr Arg Phe Thr Asp Asp Tyr Gln Leu
1               5                   10                  15

Phe Glu Glu Leu Gly Lys Gly Ala Phe Ser Val Val Arg Arg Cys Val
            20                  25                  30

Lys Lys Thr Ser Thr Gln Glu Tyr Ala Ala Lys Ile Ile Asn Thr Lys
        35                  40                  45

Lys Leu Ser Ala Arg Asp His Gln Lys Leu Glu Arg Glu Ala Arg Ile
    50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
            100                 105                 110

Ala Ser His Cys Ile His Gln Ile Leu Glu Ser Val Asn His Ile His
        115                 120                 125

Gln His Asp Ile Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala Asp Gln Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Arg Lys Phe Asn Ala Arg Arg Lys Leu Lys Gly Ala Ile
    290                 295                 300

Leu Thr Thr Met Leu Val Ser Arg Asn Phe Ser Ala Ala Lys Ser Leu
305                 310                 315                 320

Leu Asn Lys Lys Ser Asp Gly Val Lys Pro Gln Ser Asn Asn Lys
                325                 330                 335

Asn Ser Leu Glu Pro Gln Thr Thr Val Val His Asn Ala Thr Asp Gly
            340                 345                 350

Ile Lys Gly Ser Thr Glu Ser Cys Asn Thr Thr Thr Glu Asp Glu Asp
        355                 360                 365

Leu Lys Ala Arg Cys Leu Lys Asp Gly Ala Pro Gly Thr Glu Gln Pro
```

```
                    370                 375                 380
Pro Leu Gln Ala Cys Ser Pro Ser Leu Leu Ser Ala Pro Gln Pro Cys
385                 390                 395                 400

Glu Asn Arg Arg Ser Leu Arg Leu Gln Asn Ser
                    405                 410

<210> SEQ ID NO 11
<211> LENGTH: 504
<212> TYPE: PRT
<213> ORGANISM: Homo sapiens

<400> SEQUENCE: 11

Met Ala Thr Thr Ala Thr Cys Thr Arg Phe Thr Asp Asp Tyr Gln Leu
1               5                   10                  15

Phe Glu Glu Leu Gly Lys Gly Ala Phe Ser Val Val Arg Arg Cys Val
                20                  25                  30

Lys Lys Thr Ser Thr Gln Glu Tyr Ala Ala Lys Ile Ile Asn Thr Lys
            35                  40                  45

Lys Leu Ser Ala Arg Asp His Gln Lys Leu Glu Arg Glu Ala Arg Ile
        50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
                100                 105                 110

Ala Ser His Cys Ile His Gln Ile Leu Glu Ser Val Asn His Ile His
            115                 120                 125

Gln His Asp Ile Val His Arg Asp Leu Lys Pro Glu Asn Leu Leu Leu
        130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
                180                 185                 190

Lys Pro Val Asp Ile Trp Ala Cys Gly Val Ile Leu Tyr Ile Leu Leu
            195                 200                 205

Val Gly Tyr Pro Pro Phe Trp Asp Glu Asp Gln His Lys Leu Tyr Gln
210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala Asp Gln Ala Leu Lys His Pro Trp Val
                260                 265                 270

Cys Gln Arg Ser Thr Val Ala Ser Met Met His Arg Gln Glu Thr Val
            275                 280                 285

Glu Cys Leu Arg Lys Phe Asn Ala Arg Arg Lys Leu Lys Gly Ala Ile
        290                 295                 300

Leu Thr Thr Met Leu Val Ser Arg Asn Phe Ser Ala Ala Lys Ser Leu
305                 310                 315                 320

Leu Asn Lys Lys Ser Asp Gly Gly Val Lys Pro Gln Ser Asn Asn Lys
                325                 330                 335

Asn Ser Leu Glu Pro Gln Thr Thr Val Val His Asn Ala Thr Asp Gly
```

```
                340                 345                 350
Ile Lys Gly Ser Thr Glu Ser Cys Asn Thr Thr Glu Asp Glu Asp
            355                 360                 365

Leu Lys Val Arg Lys Gln Glu Ile Ile Lys Ile Thr Glu Gln Leu Ile
        370                 375                 380

Glu Ala Ile Asn Asn Gly Asp Phe Glu Ala Tyr Thr Lys Ile Cys Asp
385                 390                 395                 400

Pro Gly Leu Thr Ser Phe Glu Pro Glu Ala Leu Gly Asn Leu Val Glu
                405                 410                 415

Gly Met Asp Phe His Lys Phe Tyr Phe Glu Asn Leu Leu Ser Lys Asn
            420                 425                 430

Ser Lys Pro Ile His Thr Thr Ile Leu Asn Pro His Val His Val Ile
        435                 440                 445

Gly Glu Asp Ala Ala Cys Ile Ala Tyr Ile Arg Leu Thr Gln Tyr Ile
    450                 455                 460

Asp Gly Gln Gly Arg Pro Arg Thr Ser Gln Ser Glu Glu Thr Arg Val
465                 470                 475                 480

Trp His Arg Arg Asp Gly Lys Trp Leu Asn Val His Tyr His Cys Ser
                485                 490                 495

Gly Ala Pro Ala Ala Pro Leu Gln
            500

<210> SEQ ID NO 12
<211> LENGTH: 195
<212> TYPE: PRT
<213> ORGANISM: Homo sapiens

<400> SEQUENCE: 12

Met Gly Ser Gln Ser Ser Lys Ala Pro Arg Gly Asp Val Thr Ala Glu
1               5                   10                  15

Glu Ala Ala Gly Ala Ser Pro Ala Lys Ala Asn Gly Gln Glu Asn Gly
            20                  25                  30

His Val Lys Ser Asn Gly Asp Leu Ser Pro Lys Gly Glu Gly Glu Ser
        35                  40                  45

Pro Pro Val Asn Gly Thr Asp Glu Ala Ala Gly Ala Thr Gly Asp Ala
    50                  55                  60

Ile Glu Pro Ala Pro Pro Ser Gln Gly Ala Glu Ala Lys Gly Glu Val
65                  70                  75                  80

Pro Pro Lys Glu Thr Pro Lys Lys Lys Lys Phe Ser Phe Lys Lys
                85                  90                  95

Pro Phe Lys Leu Ser Gly Leu Ser Phe Lys Arg Asn Arg Lys Glu Gly
            100                 105                 110

Gly Gly Asp Ser Ser Ala Ser Ser Pro Thr Glu Glu Glu Gln Glu Gln
        115                 120                 125

Gly Glu Ile Gly Ala Cys Ser Asp Glu Gly Thr Ala Gln Glu Gly Lys
    130                 135                 140

Ala Ala Ala Thr Pro Glu Ser Gln Glu Pro Gln Ala Lys Gly Ala Glu
145                 150                 155                 160

Ala Ser Ala Ala Ser Glu Glu Glu Ala Gly Pro Gln Ala Thr Glu Pro
                165                 170                 175

Ser Thr Pro Ser Gly Pro Glu Ser Gly Pro Thr Pro Ala Ser Ala Glu
            180                 185                 190

Gln Asn Glu
        195
```

-continued

```
<210> SEQ ID NO 13
<211> LENGTH: 1821
<212> TYPE: PRT
<213> ORGANISM: Homo sapiens

<400> SEQUENCE: 13
```

| | | | | | | | | | | | | | | | |
|---|---|---|---|---|---|---|---|---|---|---|---|---|---|---|---|
| Met | Arg | Pro | Arg | Thr | Lys | Ala | Arg | Ser | Pro | Gly | Arg | Ala | Leu | Arg | Asn |
| 1 | | | | 5 | | | | | 10 | | | | | 15 | |
| Pro | Trp | Arg | Gly | Phe | Leu | Pro | Leu | Thr | Leu | Ala | Leu | Phe | Val | Gly | Ala |
| | | | 20 | | | | | 25 | | | | | 30 | | |
| Gly | His | Ala | Gln | Arg | Asp | Pro | Val | Gly | Arg | Tyr | Glu | Pro | Ala | Gly | Gly |
| | | 35 | | | | | 40 | | | | | 45 | | | |
| Asp | Ala | Asn | Arg | Leu | Arg | Arg | Pro | Gly | Gly | Ser | Tyr | Pro | Ala | Ala | Ala |
| 50 | | | | | 55 | | | | | 60 | | | | | |
| Ala | Ala | Lys | Val | Tyr | Ser | Leu | Phe | Arg | Glu | Gln | Asp | Ala | Pro | Val | Ala |
| 65 | | | | | 70 | | | | | 75 | | | | | 80 |
| Gly | Leu | Gln | Pro | Val | Glu | Arg | Ala | Gln | Pro | Gly | Trp | Gly | Ser | Pro | Arg |
| | | | | 85 | | | | | 90 | | | | | 95 | |
| Arg | Pro | Thr | Glu | Ala | Glu | Ala | Arg | Arg | Pro | Ser | Arg | Ala | Gln | Gln | Ser |
| | | | 100 | | | | | 105 | | | | | 110 | | |
| Arg | Arg | Val | Gln | Pro | Pro | Ala | Gln | Thr | Arg | Arg | Ser | Thr | Pro | Leu | Gly |
| | | 115 | | | | | 120 | | | | | 125 | | | |
| Gln | Gln | Gln | Pro | Ala | Pro | Arg | Thr | Arg | Ala | Ala | Pro | Ala | Leu | Pro | Arg |
| 130 | | | | | 135 | | | | | 140 | | | | | |
| Leu | Gly | Thr | Pro | Gln | Arg | Ser | Gly | Ala | Ala | Pro | Pro | Thr | Pro | Pro | Arg |
| 145 | | | | | 150 | | | | | 155 | | | | | 160 |
| Gly | Arg | Leu | Thr | Gly | Arg | Asn | Val | Cys | Gly | Gly | Gln | Cys | Cys | Pro | Gly |
| | | | | 165 | | | | | 170 | | | | | 175 | |
| Trp | Thr | Thr | Ala | Asn | Ser | Thr | Asn | His | Cys | Ile | Lys | Pro | Val | Cys | Glu |
| | | | 180 | | | | | 185 | | | | | 190 | | |
| Pro | Pro | Cys | Gln | Asn | Arg | Gly | Ser | Cys | Ser | Arg | Pro | Gln | Leu | Cys | Val |
| | | 195 | | | | | 200 | | | | | 205 | | | |
| Cys | Arg | Ser | Gly | Phe | Arg | Gly | Ala | Arg | Cys | Glu | Glu | Val | Ile | Pro | Asp |
| | 210 | | | | | 215 | | | | | 220 | | | | |
| Glu | Glu | Phe | Asp | Pro | Gln | Asn | Ser | Arg | Leu | Ala | Pro | Arg | Arg | Trp | Ala |
| 225 | | | | | 230 | | | | | 235 | | | | | 240 |
| Glu | Arg | Ser | Pro | Asn | Leu | Arg | Arg | Ser | Ser | Ala | Ala | Gly | Glu | Gly | Thr |
| | | | | 245 | | | | | 250 | | | | | 255 | |
| Leu | Ala | Arg | Ala | Gln | Pro | Pro | Ala | Pro | Gln | Ser | Pro | Ala | Pro | Gln | |
| | | | 260 | | | | | 265 | | | | | 270 | | |
| Ser | Pro | Pro | Ala | Gly | Thr | Leu | Ser | Gly | Leu | Ser | Gln | Thr | His | Pro | Ser |
| | | 275 | | | | | 280 | | | | | 285 | | | |
| Gln | Gln | His | Val | Gly | Leu | Ser | Arg | Thr | Val | Arg | Leu | His | Pro | Thr | Ala |
| | 290 | | | | | 295 | | | | | 300 | | | | |
| Thr | Ala | Ser | Ser | Gln | Leu | Ser | Ser | Asn | Ala | Leu | Pro | Pro | Gly | Pro | Gly |
| 305 | | | | | 310 | | | | | 315 | | | | | 320 |
| Leu | Glu | Gln | Arg | Asp | Gly | Thr | Gln | Ala | Val | Pro | Leu | Glu | His | Pro | |
| | | | | 325 | | | | | 330 | | | | | 335 | |
| Ser | Ser | Pro | Trp | Gly | Leu | Asn | Leu | Thr | Glu | Lys | Ile | Lys | Lys | Ile | Lys |
| | | | 340 | | | | | 345 | | | | | 350 | | |
| Ile | Val | Phe | Thr | Pro | Thr | Ile | Cys | Lys | Gln | Thr | Cys | Ala | Arg | Gly | His |
| | | 355 | | | | | 360 | | | | | 365 | | | |
| Cys | Ala | Asn | Ser | Cys | Glu | Arg | Gly | Asp | Thr | Thr | Thr | Leu | Tyr | Ser | Gln |
| | 370 | | | | | 375 | | | | | 380 | | | | |
| Gly | Gly | His | Gly | His | Asp | Pro | Lys | Ser | Gly | Phe | Arg | Ile | Tyr | Phe | Cys |

-continued

```
                385                 390                 395                 400
Gln Ile Pro Cys Leu Asn Gly Gly Arg Cys Ile Gly Arg Asp Glu Cys
                405                 410                 415
Trp Cys Pro Ala Asn Ser Thr Gly Lys Phe Cys His Leu Pro Ile Pro
            420                 425                 430
Gln Pro Asp Arg Glu Pro Pro Gly Arg Gly Ser Arg Pro Arg Ala Leu
        435                 440                 445
Leu Glu Ala Pro Leu Lys Gln Ser Thr Phe Thr Leu Pro Leu Ser Asn
    450                 455                 460
Gln Leu Ala Ser Val Asn Pro Ser Leu Val Lys Val His Ile His His
465                 470                 475                 480
Pro Pro Glu Ala Ser Val Gln Ile His Gln Val Ala Gln Val Arg Gly
                485                 490                 495
Gly Val Glu Glu Ala Leu Val Glu Asn Ser Val Glu Thr Arg Pro Pro
                500                 505                 510
Pro Trp Leu Pro Ala Ser Pro Gly His Ser Leu Trp Asp Ser Asn Asn
            515                 520                 525
Ile Pro Ala Arg Ser Gly Glu Pro Pro Arg Pro Leu Pro Pro Ala Ala
        530                 535                 540
Pro Arg Pro Arg Gly Leu Leu Gly Arg Cys Tyr Leu Asn Thr Val Asn
545                 550                 555                 560
Gly Gln Cys Ala Asn Pro Leu Leu Glu Leu Thr Gln Glu Asp Cys
                565                 570                 575
Cys Gly Ser Val Gly Ala Phe Trp Gly Val Thr Leu Cys Ala Pro Cys
            580                 585                 590
Pro Pro Arg Pro Ala Ser Pro Val Ile Glu Asn Gly Gln Leu Glu Cys
        595                 600                 605
Pro Gln Gly Tyr Lys Arg Leu Asn Leu Thr His Cys Gln Asp Ile Asn
    610                 615                 620
Glu Cys Leu Thr Leu Gly Leu Cys Lys Asp Ala Glu Cys Val Asn Thr
625                 630                 635                 640
Arg Gly Ser Tyr Leu Cys Thr Cys Arg Pro Gly Leu Met Leu Asp Pro
                645                 650                 655
Ser Arg Ser Arg Cys Val Ser Asp Lys Ala Ile Ser Met Leu Gln Gly
                660                 665                 670
Leu Cys Tyr Arg Ser Leu Gly Pro Gly Thr Cys Thr Leu Pro Leu Ala
            675                 680                 685
Gln Arg Ile Thr Lys Gln Ile Cys Cys Ser Arg Val Gly Lys Ala
        690                 695                 700
Trp Gly Ser Glu Cys Glu Lys Cys Pro Leu Pro Gly Thr Glu Ala Phe
705                 710                 715                 720
Arg Glu Ile Cys Pro Ala Gly His Gly Tyr Thr Tyr Ala Ser Ser Asp
                725                 730                 735
Ile Arg Leu Ser Met Arg Lys Ala Glu Glu Glu Leu Ala Arg Pro
                740                 745                 750
Pro Arg Glu Gln Gly Gln Arg Ser Ser Gly Ala Leu Pro Gly Pro Ala
            755                 760                 765
Glu Arg Gln Pro Leu Arg Val Val Thr Asp Thr Trp Leu Glu Ala Gly
        770                 775                 780
Thr Ile Pro Asp Lys Gly Asp Ser Gln Ala Gly Gln Val Thr Thr Ser
785                 790                 795                 800
Val Thr His Ala Pro Ala Trp Val Thr Gly Asn Ala Thr Thr Pro Pro
                805                 810                 815
```

-continued

```
Met Pro Glu Gln Gly Ile Ala Glu Ile Gln Glu Gln Val Thr Pro
                820             825             830
Ser Thr Asp Val Leu Val Thr Leu Ser Thr Pro Gly Ile Asp Arg Cys
    835             840             845
Ala Ala Gly Ala Thr Asn Val Cys Gly Pro Thr Cys Val Asn Leu
850             855             860
Pro Asp Gly Tyr Arg Cys Val Cys Ser Pro Tyr Gln Leu His Pro
865             870             875             880
Ser Gln Ala Tyr Cys Thr Asp Asp Asn Glu Cys Leu Arg Asp Pro Cys
        885             890             895
Lys Gly Lys Gly Arg Cys Ile Asn Arg Val Gly Ser Tyr Ser Cys Phe
        900             905             910
Cys Tyr Pro Gly Tyr Thr Leu Ala Thr Ser Gly Ala Thr Gln Glu Cys
    915             920             925
Gln Asp Ile Asn Glu Cys Glu Gln Pro Gly Val Cys Ser Gly Gly Gln
    930             935             940
Cys Thr Asn Thr Glu Gly Ser Tyr His Cys Glu Cys Asp Gln Gly Tyr
945             950             955             960
Ile Met Val Arg Lys Gly His Cys Gln Asp Ile Asn Glu Cys Arg His
            965             970             975
Pro Gly Thr Cys Pro Asp Gly Arg Cys Val Asn Ser Pro Gly Ser Tyr
            980             985             990
Thr Cys Leu Ala Cys Glu Glu Gly  Tyr Arg Gly Gln Ser  Gly Ser Cys
        995             1000            1005
Val Asp Val Asn Glu Cys Leu  Thr Pro Gly Val Cys  Ala His Gly
    1010            1015            1020
Lys Cys Thr Asn Leu Glu Gly  Ser Phe Arg Cys Ser  Cys Glu Gln
    1025            1030            1035
Gly Tyr Glu Val Thr Ser Asp  Glu Lys Gly Cys Gln  Asp Val Asp
    1040            1045            1050
Glu Cys Ala Ser Arg Ala Ser  Cys Pro Thr Gly Leu  Cys Leu Asn
    1055            1060            1065
Thr Glu Gly Ser Phe Ala Cys  Ser Ala Cys Glu Asn  Gly Tyr Trp
    1070            1075            1080
Val Asn Glu Asp Gly Thr Ala  Cys Glu Asp Leu Asp  Glu Cys Ala
    1085            1090            1095
Phe Pro Gly Val Cys Pro Ser  Gly Val Cys Thr Asn  Thr Ala Gly
    1100            1105            1110
Ser Phe Ser Cys Lys Asp Cys  Asp Gly Gly Tyr Arg  Pro Ser Pro
    1115            1120            1125
Leu Gly Asp Ser Cys Glu Asp  Val Asp Glu Cys Glu  Asp Pro Gln
    1130            1135            1140
Ser Ser Cys Leu Gly Gly Glu  Cys Lys Asn Thr Val  Gly Ser Tyr
    1145            1150            1155
Gln Cys Leu Cys Pro Gln Gly  Phe Gln Leu Ala Asn  Gly Thr Val
    1160            1165            1170
Cys Glu Asp Val Asn Glu Cys  Met Gly Glu Glu His  Cys Ala Pro
    1175            1180            1185
His Gly Glu Cys Leu Asn Ser  His Gly Ser Phe Phe  Cys Leu Cys
    1190            1195            1200
Ala Pro Gly Phe Val Ser Ala  Glu Gly Gly Thr Ser  Cys Gln Asp
    1205            1210            1215
Val Asp Glu Cys Ala Thr Thr  Asp Pro Cys Val Gly  Gly His Cys
    1220            1225            1230
```

```
Val Asn Thr Glu Gly Ser Phe Asn Cys Leu Cys Glu Thr Gly Phe
1235                1240                1245
Gln Pro Ser Pro Glu Ser Gly Glu Cys Val Asp Ile Asp Glu Cys
1250                1255                1260
Glu Asp Tyr Gly Asp Pro Val Cys Gly Thr Trp Lys Cys Glu Asn
1265                1270                1275
Ser Pro Gly Ser Tyr Arg Cys Val Leu Gly Cys Gln Pro Gly Phe
1280                1285                1290
His Met Ala Pro Asn Gly Asp Cys Ile Asp Ile Asp Glu Cys Ala
1295                1300                1305
Asn Asp Thr Met Cys Gly Ser His Gly Phe Cys Asp Asn Thr Asp
1310                1315                1320
Gly Ser Phe Arg Cys Leu Cys Asp Gln Gly Phe Glu Ile Ser Pro
1325                1330                1335
Ser Gly Trp Asp Cys Val Asp Val Asn Glu Cys Glu Leu Met Leu
1340                1345                1350
Ala Val Cys Gly Ala Ala Leu Cys Glu Asn Val Glu Gly Ser Phe
1355                1360                1365
Leu Cys Leu Cys Ala Ser Asp Leu Glu Glu Tyr Asp Ala Gln Glu
1370                1375                1380
Gly His Cys Arg Pro Arg Gly Ala Gly Gly Gln Ser Met Ser Glu
1385                1390                1395
Ala Pro Thr Gly Asp His Ala Pro Ala Pro Thr Arg Met Asp Cys
1400                1405                1410
Tyr Ser Gly Gln Lys Gly His Ala Pro Cys Ser Ser Val Leu Gly
1415                1420                1425
Arg Asn Thr Thr Gln Ala Glu Cys Cys Cys Thr Gln Gly Ala Ser
1430                1435                1440
Trp Gly Asp Ala Cys Asp Leu Cys Pro Ser Glu Asp Ser Ala Glu
1445                1450                1455
Phe Ser Glu Ile Cys Pro Ser Gly Lys Gly Tyr Ile Pro Val Glu
1460                1465                1470
Gly Ala Trp Thr Phe Gly Gln Thr Met Tyr Thr Asp Ala Asp Glu
1475                1480                1485
Cys Val Ile Phe Gly Pro Gly Leu Cys Pro Asn Gly Arg Cys Leu
1490                1495                1500
Asn Thr Val Pro Gly Tyr Val Cys Leu Cys Asn Pro Gly Phe His
1505                1510                1515
Tyr Asp Ala Ser His Lys Lys Cys Glu Asp His Asp Glu Cys Gln
1520                1525                1530
Asp Leu Ala Cys Glu Asn Gly Glu Cys Val Asn Thr Glu Gly Ser
1535                1540                1545
Phe His Cys Phe Cys Ser Pro Pro Leu Thr Leu Asp Leu Ser Gln
1550                1555                1560
Gln Arg Cys Met Asn Ser Thr Ser Ser Thr Glu Asp Leu Pro Asp
1565                1570                1575
His Asp Ile His Met Asp Ile Cys Trp Lys Lys Val Thr Asn Asp
1580                1585                1590
Val Cys Ser Glu Pro Leu Arg Gly His Arg Thr Thr Tyr Thr Glu
1595                1600                1605
Cys Cys Cys Gln Asp Gly Glu Ala Trp Ser Gln Gln Cys Ala Leu
1610                1615                1620
Cys Pro Pro Arg Ser Ser Glu Val Tyr Ala Gln Leu Cys Asn Val
```

-continued

```
                 1625                1630                1635

Ala Arg  Ile Glu Ala Glu  Arg Glu Ala Gly  Val His Phe Arg Pro
         1640                1645                1650

Gly Tyr  Glu Tyr Gly Pro  Gly Pro Asp Asp  Leu His Tyr Ser Ile
         1655                1660                1665

Tyr Gly  Pro Asp Gly Ala  Pro Phe Tyr Asn  Tyr Leu Gly Pro Glu
         1670                1675                1680

Asp Thr  Val Pro Glu Pro  Ala Phe Pro Asn  Thr Ala Gly His Ser
         1685                1690                1695

Ala Asp  Arg Thr Pro Ile  Leu Glu Ser Pro  Leu Gln Pro Ser Glu
         1700                1705                1710

Leu Gln  Pro His Tyr Val  Ala Ser His Pro  Glu Pro Pro Ala Gly
         1715                1720                1725

Phe Glu  Gly Leu Gln Ala  Glu Glu Cys Gly  Ile Leu Asn Gly Cys
         1730                1735                1740

Glu Asn  Gly Arg Cys Val  Arg Val Arg Glu  Gly Tyr Thr Cys Asp
         1745                1750                1755

Cys Phe  Glu Gly Phe Gln  Leu Asp Ala Ala  His Met Ala Cys Val
         1760                1765                1770

Asp Val  Asn Glu Cys Asp  Asp Leu Asn Gly  Pro Ala Val Leu Cys
         1775                1780                1785

Val His  Gly Tyr Cys Glu  Asn Thr Glu Gly  Ser Tyr Arg Cys His
         1790                1795                1800

Cys Ser  Pro Gly Tyr Val  Ala Glu Ala Gly  Pro Pro His Cys Thr
         1805                1810                1815

Ala Lys  Glu
         1820

<210> SEQ ID NO 14
<211> LENGTH: 277
<212> TYPE: PRT
<213> ORGANISM: Homo sapiens

<400> SEQUENCE: 14

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
```

165                 170                 175
Phe Leu Asp Phe Asp Leu Glu Asp Asp Pro Gly Cys Leu Ala Asp Tyr
                180                 185                 190

Val Glu Ile Tyr Asp Ser Tyr Asp Val His Gly Phe Val Gly Arg
            195                 200                 205

Tyr Cys Gly Asp Glu Leu Pro Asp Ile Ile Ser Thr Gly Asn Val
        210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
                260                 265                 270

Arg Phe Ser His Leu
                275

<210> SEQ ID NO 15
<211> LENGTH: 232
<212> TYPE: PRT
<213> ORGANISM: Homo sapiens

<400> SEQUENCE: 15

Met Lys Glu Arg Arg Ala Pro Gln Pro Val Val Ala Arg Cys Lys Leu
1               5                   10                  15

Val Leu Val Gly Asp Val Gln Cys Gly Lys Thr Ala Met Leu Gln Val
                20                  25                  30

Leu Ala Lys Asp Cys Tyr Pro Glu Thr Tyr Val Pro Thr Val Phe Glu
            35                  40                  45

Asn Tyr Thr Ala Cys Leu Glu Thr Glu Glu Gln Arg Val Glu Leu Ser
        50                  55                  60

Leu Trp Asp Thr Ser Gly Ser Pro Tyr Tyr Asp Asn Val Arg Pro Leu
65                  70                  75                  80

Cys Tyr Ser Asp Ser Asp Ala Val Leu Leu Cys Phe Asp Ile Ser Arg
                85                  90                  95

Pro Glu Thr Val Asp Ser Ala Leu Lys Lys Trp Arg Thr Glu Ile Leu
                100                 105                 110

Asp Tyr Cys Pro Ser Thr Arg Val Leu Leu Ile Gly Cys Lys Thr Asp
            115                 120                 125

Leu Arg Thr Asp Leu Ser Thr Leu Met Glu Leu Ser His Gln Lys Gln
130                 135                 140

Ala Pro Ile Ser Tyr Glu Gln Gly Cys Ala Ile Ala Lys Gln Leu Gly
145                 150                 155                 160

Ala Glu Ile Tyr Leu Glu Gly Ser Ala Phe Thr Ser Glu Lys Ser Ile
                165                 170                 175

His Ser Ile Phe Arg Thr Ala Ser Met Leu Cys Leu Asn Lys Pro Ser
            180                 185                 190

Pro Leu Pro Gln Lys Ser Pro Val Arg Ser Leu Ser Lys Arg Leu Leu
        195                 200                 205

His Leu Pro Ser Arg Ser Glu Leu Ile Ser Ser Thr Phe Lys Lys Glu
    210                 215                 220

Lys Ala Lys Ser Cys Ser Ile Met
225                 230

<210> SEQ ID NO 16
<211> LENGTH: 283
<212> TYPE: PRT

-continued

<213> ORGANISM: Homo sapiens

<400> SEQUENCE: 16

Met Pro Glu Ser Leu Asp Ser Pro Thr Ser Gly Arg Pro Gly Val Thr
1               5                   10                  15

Thr His Ser Thr Arg Thr Pro Gly Thr Glu Ile Gln Thr Ile Ile Ser
            20                  25                  30

Asn Pro Val Pro Lys Met Glu Glu Ala Lys Ser Gln Ser Leu Glu Glu
        35                  40                  45

Asp Phe Glu Gly Gln Ala Thr His Thr Gly Pro Lys Gly Val Ile Asn
    50                  55                  60

Asp Trp Arg Lys Phe Lys Leu Glu Ser Gln Asp Ser Asp Ser Ile Pro
65                  70                  75                  80

Pro Ser Lys Lys Glu Ile Leu Arg Gln Met Ser Ser Pro Gln Ser Arg
                85                  90                  95

Asn Gly Lys Asp Ser Lys Glu Arg Val Ser Arg Lys Met Ser Ile Gln
            100                 105                 110

Glu Tyr Glu Leu Ile His Lys Glu Lys Glu Asp Glu Asn Cys Leu Arg
        115                 120                 125

Lys Tyr Arg Arg Gln Cys Met Gln Asp Met His Gln Lys Leu Ser Phe
    130                 135                 140

Gly Pro Arg Tyr Gly Phe Val Tyr Glu Leu Glu Thr Gly Lys Gln Phe
145                 150                 155                 160

Leu Glu Thr Ile Glu Lys Glu Leu Lys Ile Thr Thr Ile Val Val His
                165                 170                 175

Ile Tyr Glu Asp Gly Ile Lys Gly Cys Asp Ala Leu Asn Ser Ser Leu
            180                 185                 190

Thr Cys Leu Ala Ala Glu Tyr Pro Ile Val Lys Phe Cys Lys Ile Lys
        195                 200                 205

Ala Ser Asn Thr Gly Ala Gly Asp Arg Phe Ser Leu Asp Val Leu Pro
    210                 215                 220

Thr Leu Leu Ile Tyr Lys Gly Gly Glu Leu Ile Ser Asn Phe Ile Ser
225                 230                 235                 240

Val Ala Glu Gln Phe Ala Glu Phe Phe Ala Gly Asp Val Glu Ser
                245                 250                 255

Phe Leu Asn Glu Tyr Gly Leu Pro Glu Arg Glu Val His Val Leu
            260                 265                 270

Glu His Thr Lys Ile Glu Glu Glu Asp Val Glu
        275                 280

<210> SEQ ID NO 17
<211> LENGTH: 194
<212> TYPE: PRT
<213> ORGANISM: Homo sapiens

<400> SEQUENCE: 17

Met Ser Ser Pro Gln Ser Arg Asn Gly Lys Asp Ser Lys Glu Arg Val
1               5                   10                  15

Ser Arg Lys Met Ser Ile Gln Glu Tyr Glu Leu Ile His Lys Glu Lys
            20                  25                  30

Glu Asp Glu Asn Cys Leu Arg Lys Tyr Arg Arg Gln Cys Met Gln Asp
        35                  40                  45

Met His Gln Lys Leu Ser Phe Gly Pro Arg Tyr Gly Phe Val Tyr Glu
    50                  55                  60

Leu Glu Thr Gly Lys Gln Phe Leu Glu Thr Ile Glu Lys Glu Leu Lys
65                  70                  75                  80

```
Ile Thr Thr Ile Val Val His Ile Tyr Glu Asp Gly Ile Lys Gly Cys
                85                  90                  95

Asp Ala Leu Asn Ser Ser Leu Thr Cys Leu Ala Ala Glu Tyr Pro Ile
            100                 105                 110

Val Lys Phe Cys Lys Ile Lys Ala Ser Asn Thr Gly Ala Gly Asp Arg
        115                 120                 125

Phe Ser Leu Asp Val Leu Pro Thr Leu Leu Ile Tyr Lys Gly Gly Glu
    130                 135                 140

Leu Ile Ser Asn Phe Ile Ser Val Ala Glu Gln Phe Ala Glu Glu Phe
145                 150                 155                 160

Phe Ala Gly Asp Val Glu Ser Phe Leu Asn Glu Tyr Gly Leu Leu Pro
                165                 170                 175

Glu Arg Glu Val His Val Leu Glu His Thr Lys Ile Glu Glu Glu Asp
            180                 185                 190

Val Glu

<210> SEQ ID NO 18
<211> LENGTH: 417
<212> TYPE: PRT
<213> ORGANISM: Homo sapiens

<400> SEQUENCE: 18

Met Leu Leu Ser Val Pro Leu Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Lys Pro Glu
225                 230                 235                 240

His Ile Pro Asp Pro Asp Ala Lys Lys Pro Glu Asp Trp Asp Glu Glu
                245                 250                 255
```

```
Met Asp Gly Glu Trp Glu Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
    370                 375                 380

Lys Glu Asp Asp Glu Asp Lys Asp Glu Asp Glu Asp Glu Glu Asp
385                 390                 395                 400

Lys Glu Glu Asp Glu Glu Glu Asp Val Pro Gly Gln Ala Lys Asp Glu
                405                 410                 415

Leu

<210> SEQ ID NO 19
<211> LENGTH: 372
<212> TYPE: PRT
<213> ORGANISM: Homo sapiens

<400> SEQUENCE: 19

Met Arg Val Gly Pro Val Arg Ser Ala Met Ser Gly Ala Ser Gln Pro
1               5                   10                  15

Arg Gly Pro Ala Leu Leu Phe Pro Ala Thr Arg Gly Val Pro Ala Lys
            20                  25                  30

Arg Leu Leu Asp Ala Asp Asp Ala Ala Val Ala Ala Lys Cys Pro
        35                  40                  45

Arg Leu Ser Glu Cys Ser Ser Pro Pro Asp Tyr Leu Ser Pro Pro Gly
    50                  55                  60

Ser Pro Cys Ser Pro Gln Pro Pro Ala Ala Pro Gly Ala Gly Gly
65                  70                  75                  80

Gly Ser Gly Ser Ala Pro Gly Pro Ser Arg Ile Ala Asp Tyr Leu Leu
                85                  90                  95

Leu Pro Leu Ala Glu Arg Glu His Val Ser Arg Ala Leu Cys Ile His
            100                 105                 110

Thr Gly Arg Glu Leu Arg Cys Lys Val Phe Pro Ile Lys His Tyr Gln
        115                 120                 125

Asp Lys Ile Arg Pro Tyr Ile Gln Leu Pro Ser His Ser Asn Ile Thr
    130                 135                 140

Gly Ile Val Glu Val Ile Leu Gly Glu Thr Lys Ala Tyr Val Phe Phe
145                 150                 155                 160

Glu Lys Asp Phe Gly Asp Met His Ser Tyr Val Arg Ser Arg Lys Arg
                165                 170                 175

Leu Arg Glu Glu Glu Ala Ala Arg Leu Phe Lys Gln Ile Val Ser Ala
            180                 185                 190

Val Ala His Cys His Gln Ser Ala Ile Val Leu Gly Asp Leu Lys Leu
        195                 200                 205

Arg Lys Phe Val Phe Ser Thr Glu Glu Arg Thr Gln Leu Arg Leu Glu
```

```
            210                 215                 220
Ser Leu Glu Asp Thr His Ile Met Lys Gly Glu Asp Ala Leu Ser
225                 230                 235                 240

Asp Lys His Gly Cys Pro Ala Tyr Val Ser Pro Glu Ile Leu Asn Thr
                245                 250                 255

Thr Gly Thr Tyr Ser Gly Lys Ala Ala Asp Val Trp Ser Leu Gly Val
                260                 265                 270

Met Leu Tyr Thr Leu Leu Val Gly Arg Tyr Pro Phe His Asp Ser Asp
                275                 280                 285

Pro Ser Ala Leu Phe Ser Lys Ile Arg Arg Gly Gln Phe Cys Ile Pro
290                 295                 300

Glu His Ile Ser Pro Lys Ala Arg Cys Leu Ile Arg Ser Leu Leu Arg
305                 310                 315                 320

Arg Glu Pro Ser Glu Arg Leu Thr Ala Pro Glu Ile Leu Leu His Pro
                325                 330                 335

Trp Phe Glu Ser Val Leu Glu Pro Gly Tyr Ile Asp Ser Glu Ile Gly
                340                 345                 350

Thr Ser Asp Gln Ile Val Pro Glu Tyr Gln Glu Asp Ser Asp Ile Ser
                355                 360                 365

Ser Phe Phe Cys
    370

<210> SEQ ID NO 20
<211> LENGTH: 352
<212> TYPE: PRT
<213> ORGANISM: Homo sapiens

<400> SEQUENCE: 20

Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
                35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
                115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Val Phe Gln Phe Gln His Ile Met Val Gly Leu
                195                 200                 205

Ile Leu Pro Gly Ile Val Ile Leu Ser Cys Tyr Cys Ile Ile Ile Ser
```

```
                210                 215                 220
Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
                260                 265                 270

Gly Cys Glu Phe Glu Asn Thr Val His Lys Trp Ile Ser Ile Thr Glu
                275                 280                 285

Ala Leu Ala Phe Phe His Cys Cys Leu Asn Pro Ile Leu Tyr Ala Phe
                290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
                340                 345                 350

<210> SEQ ID NO 21
<211> LENGTH: 638
<212> TYPE: PRT
<213> ORGANISM: Homo sapiens

<400> SEQUENCE: 21

Met Asp Leu Trp Gln Leu Leu Leu Thr Leu Ala Leu Ala Gly Ser Ser
1               5                   10                  15

Asp Ala Phe Ser Gly Ser Glu Ala Thr Ala Ala Ile Leu Ser Arg Ala
                20                  25                  30

Pro Trp Ser Leu Gln Ser Val Asn Pro Gly Leu Lys Thr Asn Ser Ser
                35                  40                  45

Lys Glu Pro Lys Phe Thr Lys Cys Arg Ser Pro Glu Arg Glu Thr Phe
                50                  55                  60

Ser Cys His Trp Thr Asp Glu Val His His Gly Thr Lys Asn Leu Gly
65                  70                  75                  80

Pro Ile Gln Leu Phe Tyr Thr Arg Arg Asn Thr Gln Glu Trp Thr Gln
                85                  90                  95

Glu Trp Lys Glu Cys Pro Asp Tyr Val Ser Ala Gly Glu Asn Ser Cys
                100                 105                 110

Tyr Phe Asn Ser Ser Phe Thr Ser Ile Trp Ile Pro Tyr Cys Ile Lys
                115                 120                 125

Leu Thr Ser Asn Gly Gly Thr Val Asp Glu Lys Cys Phe Ser Val Asp
130                 135                 140

Glu Ile Val Gln Pro Asp Pro Pro Ile Ala Leu Asn Trp Thr Leu Leu
145                 150                 155                 160

Asn Val Ser Leu Thr Gly Ile His Ala Asp Ile Gln Val Arg Trp Glu
                165                 170                 175

Ala Pro Arg Asn Ala Asp Ile Gln Lys Gly Trp Met Val Leu Glu Tyr
                180                 185                 190

Glu Leu Gln Tyr Lys Glu Val Asn Glu Thr Lys Trp Lys Met Met Asp
                195                 200                 205

Pro Ile Leu Thr Thr Ser Val Pro Val Tyr Ser Leu Lys Val Asp Lys
                210                 215                 220

Glu Tyr Glu Val Arg Val Arg Ser Lys Gln Arg Asn Ser Gly Asn Tyr
225                 230                 235                 240

Gly Glu Phe Ser Glu Val Leu Tyr Val Thr Leu Pro Gln Met Ser Gln
```

```
                    245                 250                 255
Phe Thr Cys Glu Glu Asp Phe Tyr Phe Pro Trp Leu Leu Ile Ile Ile
                260                 265                 270

Phe Gly Ile Phe Gly Leu Thr Val Met Leu Phe Val Phe Leu Phe Ser
            275                 280                 285

Lys Gln Gln Arg Ile Lys Met Leu Ile Leu Pro Pro Val Pro Val Pro
        290                 295                 300

Lys Ile Lys Gly Ile Asp Pro Asp Leu Leu Lys Glu Gly Lys Leu Glu
305                 310                 315                 320

Glu Val Asn Thr Ile Leu Ala Ile His Asp Ser Tyr Lys Pro Glu Phe
                325                 330                 335

His Ser Asp Asp Ser Trp Val Glu Phe Ile Glu Leu Asp Ile Asp Glu
            340                 345                 350

Pro Asp Glu Lys Thr Glu Glu Ser Asp Thr Asp Arg Leu Leu Ser Ser
        355                 360                 365

Asp His Glu Lys Ser His Ser Asn Leu Gly Val Lys Asp Gly Asp Ser
    370                 375                 380

Gly Arg Thr Ser Cys Cys Glu Pro Asp Ile Leu Glu Thr Asp Phe Asn
385                 390                 395                 400

Ala Asn Asp Ile His Glu Gly Thr Ser Glu Val Ala Gln Pro Gln Arg
                405                 410                 415

Leu Lys Gly Glu Ala Asp Leu Leu Cys Leu Asp Gln Lys Asn Gln Asn
            420                 425                 430

Asn Ser Pro Tyr His Asp Ala Cys Pro Ala Thr Gln Gln Pro Ser Val
        435                 440                 445

Ile Gln Ala Glu Lys Asn Lys Pro Gln Pro Leu Pro Thr Glu Gly Ala
    450                 455                 460

Glu Ser Thr His Gln Ala Ala His Ile Gln Leu Ser Asn Pro Ser Ser
465                 470                 475                 480

Leu Ser Asn Ile Asp Phe Tyr Ala Gln Val Ser Asp Ile Thr Pro Ala
                485                 490                 495

Gly Ser Val Val Leu Ser Pro Gly Gln Lys Asn Lys Ala Gly Met Ser
            500                 505                 510

Gln Cys Asp Met His Pro Glu Met Val Ser Leu Cys Gln Glu Asn Phe
        515                 520                 525

Leu Met Asp Asn Ala Tyr Phe Cys Glu Ala Asp Ala Lys Lys Cys Ile
    530                 535                 540

Pro Val Ala Pro His Ile Lys Val Glu Ser His Ile Gln Pro Ser Leu
545                 550                 555                 560

Asn Gln Glu Asp Ile Tyr Ile Thr Thr Glu Ser Leu Thr Thr Ala Ala
                565                 570                 575

Gly Arg Pro Gly Thr Gly Glu His Val Pro Gly Ser Glu Met Pro Val
            580                 585                 590

Pro Asp Tyr Thr Ser Ile His Ile Val Gln Ser Pro Gln Gly Leu Ile
        595                 600                 605

Leu Asn Ala Thr Ala Leu Pro Leu Pro Asp Lys Glu Phe Leu Ser Ser
    610                 615                 620

Cys Gly Tyr Val Ser Thr Asp Gln Leu Asn Lys Ile Met Pro
625                 630                 635

<210> SEQ ID NO 22
<211> LENGTH: 208
<212> TYPE: PRT
<213> ORGANISM: Homo sapiens
```

-continued

```
<400> SEQUENCE: 22

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
        35                  40                  45

Gln Leu Leu Pro Leu Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205

<210> SEQ ID NO 23
<211> LENGTH: 441
<212> TYPE: PRT
<213> ORGANISM: Homo sapiens

<400> SEQUENCE: 23

Met Val Pro Pro Lys Leu His Val Leu Phe Cys Leu Cys Gly Cys Leu
1               5                   10                  15

Ala Val Val Tyr Pro Phe Asp Trp Gln Tyr Ile Asn Pro Val Ala His
            20                  25                  30

Met Lys Ser Ser Ala Trp Val Asn Lys Ile Gln Val Leu Met Ala Ala
        35                  40                  45

Ala Ser Phe Gly Gln Thr Lys Ile Pro Arg Gly Asn Gly Pro Tyr Ser
    50                  55                  60

Val Gly Cys Thr Asp Leu Met Phe Asp His Thr Asn Lys Gly Thr Phe
65                  70                  75                  80

Leu Arg Leu Tyr Tyr Pro Ser Gln Asp Asn Asp Arg Leu Asp Thr Leu
                85                  90                  95

Trp Ile Pro Asn Lys Glu Tyr Phe Trp Gly Leu Ser Lys Phe Leu Gly
            100                 105                 110

Thr His Trp Leu Met Gly Asn Ile Leu Arg Leu Leu Phe Gly Ser Met
        115                 120                 125

Thr Thr Pro Ala Asn Trp Asn Ser Pro Leu Arg Pro Gly Glu Lys Tyr
    130                 135                 140

Pro Leu Val Val Phe Ser His Gly Leu Gly Ala Phe Arg Thr Leu Tyr
145                 150                 155                 160

Ser Ala Ile Gly Ile Asp Leu Ala Ser His Gly Phe Ile Val Ala Ala
```

```
                    165                 170                 175
Val Glu His Arg Asp Arg Ser Ala Ser Ala Thr Tyr Tyr Phe Lys Asp
                180                 185                 190

Gln Ser Ala Ala Glu Ile Gly Asp Lys Ser Trp Leu Tyr Leu Arg Thr
            195                 200                 205

Leu Lys Gln Glu Glu Thr His Ile Arg Asn Glu Gln Val Arg Gln
        210                 215                 220

Arg Ala Lys Glu Cys Ser Gln Ala Leu Ser Leu Ile Leu Asp Ile Asp
225                 230                 235                 240

His Gly Lys Pro Val Lys Asn Ala Leu Asp Leu Lys Phe Asp Met Glu
                245                 250                 255

Gln Leu Lys Asp Ser Ile Asp Arg Glu Lys Ile Ala Val Ile Gly His
            260                 265                 270

Ser Phe Gly Gly Ala Thr Val Ile Gln Thr Leu Ser Glu Asp Gln Arg
        275                 280                 285

Phe Arg Cys Gly Ile Ala Leu Asp Ala Trp Met Phe Pro Leu Gly Asp
    290                 295                 300

Glu Val Tyr Ser Arg Ile Pro Gln Pro Leu Phe Ile Asn Ser Glu
305                 310                 315                 320

Tyr Phe Gln Tyr Pro Ala Asn Ile Ile Lys Met Lys Lys Cys Tyr Ser
                325                 330                 335

Pro Asp Lys Glu Arg Lys Met Ile Thr Ile Arg Gly Ser Val His Gln
            340                 345                 350

Asn Phe Ala Asp Phe Thr Phe Ala Thr Gly Lys Ile Ile Gly His Met
        355                 360                 365

Leu Lys Leu Lys Gly Asp Ile Asp Ser Asn Val Ala Ile Asp Leu Ser
    370                 375                 380

Asn Lys Ala Ser Leu Ala Phe Leu Gln Lys His Leu Gly Leu His Lys
385                 390                 395                 400

Asp Phe Asp Gln Trp Asp Cys Leu Ile Glu Gly Asp Asp Glu Asn Leu
                405                 410                 415

Ile Pro Gly Thr Asn Ile Asn Thr Thr Asn Gln His Ile Met Leu Gln
            420                 425                 430

Asn Ser Ser Gly Ile Glu Lys Tyr Asn
        435                 440

<210> SEQ ID NO 24
<211> LENGTH: 171
<212> TYPE: PRT
<213> ORGANISM: Homo sapiens

<400> SEQUENCE: 24

Met Ala Lys Phe Val Ile Arg Pro Ala Thr Ala Ala Asp Cys Ser Asp
1               5                   10                  15

Ile Leu Arg Leu Ile Lys Glu Leu Ala Lys Tyr Glu Tyr Met Glu Glu
            20                  25                  30

Gln Val Ile Leu Thr Glu Lys Asp Leu Leu Glu Asp Gly Phe Gly Glu
        35                  40                  45

His Pro Phe Tyr His Cys Leu Val Ala Glu Val Pro Lys Glu His Trp
    50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
```

```
              100                 105                 110
Leu Ser Gln Val Ala Met Arg Cys Arg Cys Ser Ser Met His Phe Leu
        115                 120                 125

Val Ala Glu Trp Asn Glu Pro Ser Ile Asn Phe Tyr Lys Arg Arg Gly
    130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Thr Glu Glu
                165                 170

<210> SEQ ID NO 25
<211> LENGTH: 394
<212> TYPE: PRT
<213> ORGANISM: Homo sapiens

<400> SEQUENCE: 25

Met Ala Leu Leu Asp Leu Ala Leu Glu Gly Met Ala Val Phe Gly Phe
1               5                   10                  15

Val Leu Phe Leu Val Leu Trp Leu Met His Phe Met Ala Ile Ile Tyr
                20                  25                  30

Thr Arg Leu His Leu Asn Lys Lys Ala Thr Asp Lys Gln Pro Tyr Ser
            35                  40                  45

Lys Leu Pro Gly Val Ser Leu Leu Lys Pro Leu Lys Gly Val Asp Pro
        50                  55                  60

Asn Leu Ile Asn Asn Leu Glu Thr Phe Phe Glu Leu Asp Tyr Pro Lys
65                  70                  75                  80

Tyr Glu Val Leu Leu Cys Val Gln Asp His Asp Asp Pro Ala Ile Asp
                85                  90                  95

Val Cys Lys Lys Leu Leu Gly Lys Tyr Pro Asn Val Asp Ala Arg Leu
            100                 105                 110

Phe Ile Gly Gly Lys Lys Val Gly Ile Asn Pro Lys Ile Asn Asn Leu
        115                 120                 125

Met Pro Gly Tyr Glu Val Ala Lys Tyr Asp Leu Ile Trp Ile Cys Asp
    130                 135                 140

Ser Gly Ile Arg Val Ile Pro Asp Thr Leu Thr Asp Met Val Asn Gln
145                 150                 155                 160

Met Thr Glu Lys Val Gly Leu Val His Gly Leu Pro Tyr Val Ala Asp
                165                 170                 175

Arg Gln Gly Phe Ala Ala Thr Leu Glu Gln Val Tyr Phe Gly Thr Ser
            180                 185                 190

His Pro Arg Tyr Tyr Ile Ser Ala Asn Val Thr Gly Phe Lys Cys Val
        195                 200                 205

Thr Gly Met Ser Cys Leu Met Arg Lys Asp Val Leu Asp Gln Ala Gly
    210                 215                 220

Gly Leu Ile Ala Phe Ala Gln Tyr Ile Ala Glu Asp Tyr Phe Met Ala
225                 230                 235                 240

Lys Ala Ile Ala Asp Arg Gly Trp Arg Phe Ala Met Ser Thr Gln Val
                245                 250                 255

Ala Met Gln Asn Ser Gly Ser Tyr Ser Ile Ser Gln Phe Gln Ser Arg
            260                 265                 270

Met Ile Arg Trp Thr Lys Leu Arg Ile Asn Met Leu Pro Ala Thr Ile
        275                 280                 285

Ile Cys Glu Pro Ile Ser Glu Cys Phe Val Ala Ser Leu Ile Ile Gly
    290                 295                 300

Trp Ala Ala His His Val Phe Arg Trp Asp Ile Met Val Phe Phe Met
```

```
                 305                 310                 315                 320
Cys His Cys Leu Ala Trp Phe Ile Phe Asp Tyr Ile Gln Leu Arg Gly
                325                 330                 335

Val Gln Gly Gly Thr Leu Cys Phe Ser Lys Leu Asp Tyr Ala Val Ala
                340                 345                 350

Trp Phe Ile Arg Glu Ser Met Thr Ile Tyr Ile Phe Leu Ser Ala Leu
                355                 360                 365

Trp Asp Pro Thr Ile Ser Trp Arg Thr Gly Arg Tyr Arg Leu Arg Cys
        370                 375                 380

Gly Gly Thr Ala Glu Glu Ile Leu Asp Val
385                 390

<210> SEQ ID NO 26
<211> LENGTH: 42
<212> TYPE: PRT
<213> ORGANISM: Mus musculus

<400> SEQUENCE: 26

Asp Pro Cys Leu Arg Lys Tyr Lys Asp Tyr Cys Ile His Gly Glu Cys
1               5                   10                  15

Arg Tyr Leu Gln Glu Phe Arg Thr Pro Ser Cys Lys Cys Leu Pro Gly
                20                  25                  30

Tyr His Gly His Arg Cys His Gly Leu Thr
            35                  40

<210> SEQ ID NO 27
<211> LENGTH: 42
<212> TYPE: PRT
<213> ORGANISM: Rattus norvegicus

<400> SEQUENCE: 27

Asp Pro Cys Leu Lys Lys Tyr Lys Asp Tyr Cys Ile His Gly Glu Cys
1               5                   10                  15

Arg Tyr Leu Lys Glu Leu Arg Ile Pro Ser Cys His Cys Leu Pro Gly
                20                  25                  30

Tyr His Gly Gln Arg Cys His Gly Leu Thr
            35                  40

<210> SEQ ID NO 28
<211> LENGTH: 42
<212> TYPE: PRT
<213> ORGANISM: Cricetulus griseus

<400> SEQUENCE: 28

Asp Pro Cys Leu Arg Lys Tyr Lys Asp Phe Cys Ile His Gly Glu Cys
1               5                   10                  15

Lys Tyr Leu Lys Asp Leu Arg Ala Pro Ser Cys Asn Cys His Pro Gly
                20                  25                  30

Tyr His Gly Glu Arg Cys His Gly Leu Thr
            35                  40

<210> SEQ ID NO 29
<211> LENGTH: 42
<212> TYPE: PRT
<213> ORGANISM: Oryctolagus cuniculus

<400> SEQUENCE: 29

Asp Pro Cys Leu Arg Lys Tyr Lys Asp Phe Cys Ile His Gly Glu Cys
1               5                   10                  15

Lys Tyr Leu Lys Glu Leu Arg Ala Pro Ser Cys Ile Cys His Pro Gly
```

```
                     20                  25                  30

Tyr His Gly Glu Arg Cys His Gly Leu Ser
            35                  40

<210> SEQ ID NO 30
<211> LENGTH: 42
<212> TYPE: PRT
<213> ORGANISM: Sus scrofa

<400> SEQUENCE: 30

Asp Pro Cys Leu Arg Lys Tyr Lys Asp Phe Cys Ile His Gly Glu Cys
1               5                   10                  15

Lys Tyr Val Lys Glu Leu Arg Ala Pro Ser Cys Ile Cys His Pro Gly
            20                  25                  30

Tyr His Gly Glu Arg Cys His Gly Leu Ser
            35                  40

<210> SEQ ID NO 31
<211> LENGTH: 42
<212> TYPE: PRT
<213> ORGANISM: monkey

<400> SEQUENCE: 31

Asp Pro Cys Leu Arg Lys Tyr Lys Asp Phe Cys Ile His Gly Glu Cys
1               5                   10                  15

Lys Tyr Val Lys Glu Leu Arg Ala Pro Ser Cys Ile Cys His Pro Gly
            20                  25                  30

Tyr His Gly Glu Arg Cys His Gly Leu Ser
            35                  40

<210> SEQ ID NO 32
<211> LENGTH: 42
<212> TYPE: PRT
<213> ORGANISM: Homo sapiens

<400> SEQUENCE: 32

Asp Pro Cys Leu Arg Lys Tyr Lys Asp Phe Cys Ile His Gly Glu Cys
1               5                   10                  15

Lys Tyr Val Lys Glu Leu Arg Ala Pro Ser Cys Ile Cys His Pro Gly
            20                  25                  30

Tyr His Gly Glu Arg Cys His Gly Leu Ser
            35                  40

<210> SEQ ID NO 33
<211> LENGTH: 42
<212> TYPE: PRT
<213> ORGANISM: Gallus gallus

<400> SEQUENCE: 33

Asp Pro Cys Leu Arg Lys Tyr Lys Asp Phe Cys Ile His Gly Glu Cys
1               5                   10                  15

Lys Tyr Ile Arg Glu Leu Gly Ala Pro Ser Cys Ile Cys Gln Pro Gly
            20                  25                  30

Tyr His Gly Glu Arg Cys His Gly Leu Leu
            35                  40
```